(12) United States Patent
Rader et al.

(10) Patent No.: US 12,286,487 B2
(45) Date of Patent: Apr. 29, 2025

(54) ANTIBODY COMPOUNDS WITH REACTIVE ARGININE AND RELATED ANTIBODY DRUG CONJUGATES

(71) Applicant: University of Florida Research Foundation, Incorporated, Gainesville, FL (US)

(72) Inventors: Christoph Rader, Jupiter, FL (US); Dobeen Hwang, Palm Beach Gardens, FL (US); Napon Nilchan, Jupiter, FL (US)

(73) Assignee: University Of Florida Research Foundation, Incorporated, Gainesville, FL (US)

( * ) Notice: Subject to any disclaimer, the term of this patent is extended or adjusted under 35 U.S.C. 154(b) by 64 days.

(21) Appl. No.: 17/284,192

(22) PCT Filed: Oct. 8, 2019

(86) PCT No.: PCT/US2019/055224
§ 371 (c)(1),
(2) Date: Apr. 9, 2021

(87) PCT Pub. No.: WO2020/076849
PCT Pub. Date: Apr. 16, 2020

(65) Prior Publication Data
US 2021/0340277 A1 Nov. 4, 2021

Related U.S. Application Data

(60) Provisional application No. 62/744,339, filed on Oct. 11, 2018.

(51) Int. Cl.
| | |
|---|---|
| C07K 16/44 | (2006.01) |
| A61K 47/54 | (2017.01) |
| A61K 47/68 | (2017.01) |
| C07K 16/32 | (2006.01) |

(52) U.S. Cl.
CPC ............ *C07K 16/44* (2013.01); *A61K 47/542* (2017.08); *A61K 47/68031* (2023.08); *A61K 47/6851* (2017.08); *C07K 16/32* (2013.01); *C07K 2317/24* (2013.01); *C07K 2317/31* (2013.01); *C07K 2317/55* (2013.01)

(58) Field of Classification Search
None
See application file for complete search history.

(56) References Cited

U.S. PATENT DOCUMENTS 5,733,757 A 3/1998 Barbas, III
2012/0282279 A1 11/2012 Das et al.

FOREIGN PATENT DOCUMENTS

| AR | 106453 A1 | 1/2018 |
|---|---|---|
| CN | 1968712 A | 5/2007 |
| CN | 101965406 A | 2/2011 |
| CN | 108025071 A | 5/2018 |
| WO | WO-97/21803 A1 | 6/1997 |
| WO | WO-2017/049139 A2 | 3/2017 |

OTHER PUBLICATIONS

Nanna et al. Harnessing a catalytic lysine residue for the one-step preparation of homogeneous antibody-drug conjugates. Nat Commun, 2017;8(1):1112 (Year: 2017).*
Barbas et al., Immune Versus Natural Selection: Antibody Aldolases with Enzymic Rates But Broader Scope. Science 1997; 278: 2085 (Year: 1997).*
Rader et al., A Humanized Aldolase Antibody for Selective Chemotherapy and Adaptor Immunotherapy JMB 2003; 332:889 (Year: 2003).*
Office Action for Chinese Application No. 201980081369.0, dated Jan. 18, 2024, 8 pages.
International Search Report and Written Opinion for International Application No. PCT/US2019/055224, dated Jan. 27, 2020, (11 pages), U.S. Patent and Trademark Office, US.
Extended European Search Report for European Patent Application No. 19871937.9, dated May 30, 2022, (11 pages), European Patent Office, Munich, Germany.
Bjelic, Sinisa et al. "Exploration of Alternate Catalytic Mechanisms and Optimization Strategies For Retroaldolase Design," *Journal of Molecular Biology*, vol. 426, No. 1, Jan. 9, 2014, (Epub: Oct. 23, 2013), pp. 256-271, DOI: 10.1016/j.jmb.2013.10.012.
Chaubet, Guilhem et al. "Recent, Non-Classical, Aproaches To Antibody Lysine Modification," *Drug Discovery Today: Technologies*, vol. 30, Sep. 27, 2018, pp. 21-26, DOI: 10.1016/j.ddtec.2018.09.002.
Hwang, Dobeen et al. "Site-Selective Antibody Functionalization Via Orthogonally Reactive Arginine and Lysine Residues," *Cell Chemical Biology*, vol. 26, Issue 9, Sep. 19, 2019, pp. 1229-1239.e9, DOI: 10.1016/j.chembiol.2019.05.010.
Nanna, Alex R. et al. "Harnessing A Catalytic Lysine Residue For The One-Step Preparation Of Homogeneous Antibody-Drug Conjugates," *Nature Communications*, vol. 8, No. 1112, Oct. 24, 2017, pp. 1-9, DOI: 10.1038/s41467-017-01257-1.

* cited by examiner

*Primary Examiner* — Daniel E Kolker
*Assistant Examiner* — Maureen Varina Driscoll
(74) *Attorney, Agent, or Firm* — Alston & Bird LLP

(57) ABSTRACT

The present invention provides antibody compounds that contain a substitution of arginine for the reactive lysine residue (Lys99) in the hydrophobic cleft (38C2_Arg). The invention also provides antibody drug conjugate compounds (ADCs) that contain cargo moieties that are site-specifically conjugated to the engineered arginine residue in the 38C2_Arg variant antibody. Further provided in the invention are therapeutic applications of the compounds.

34 Claims, 18 Drawing Sheets
Specification includes a Sequence Listing.

*Fig. 3 (Cont'd)*
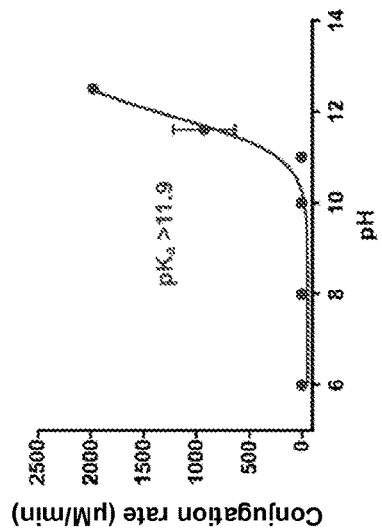
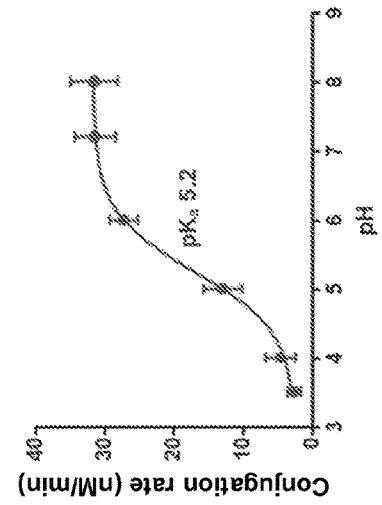
b

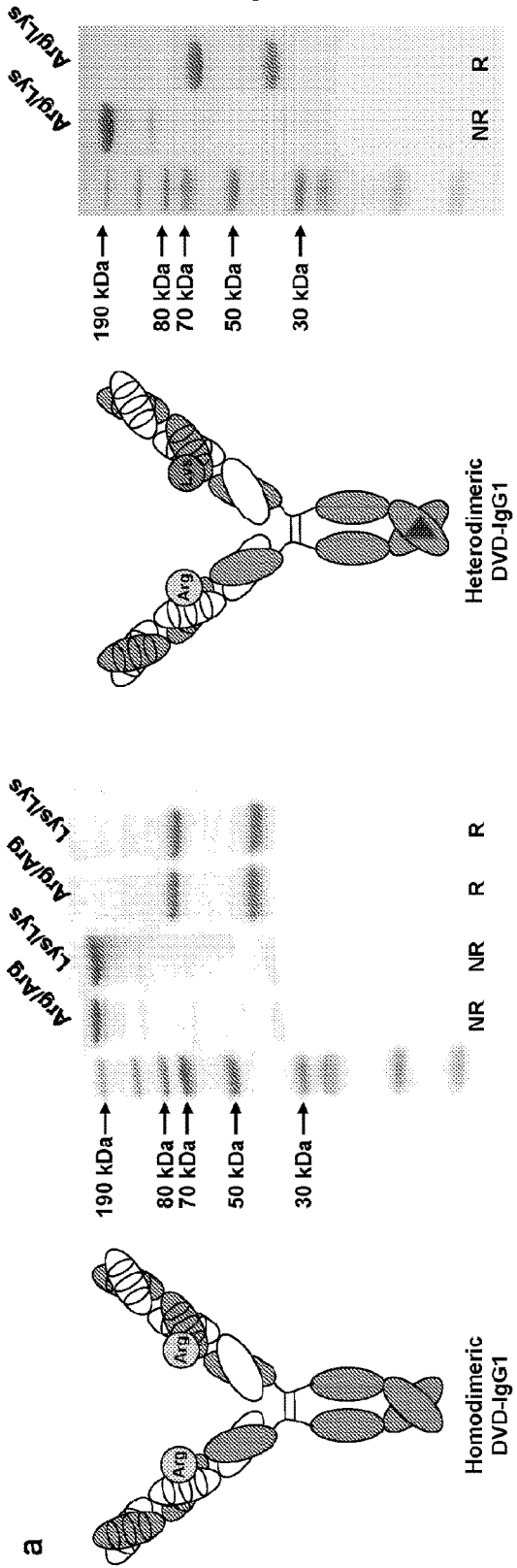
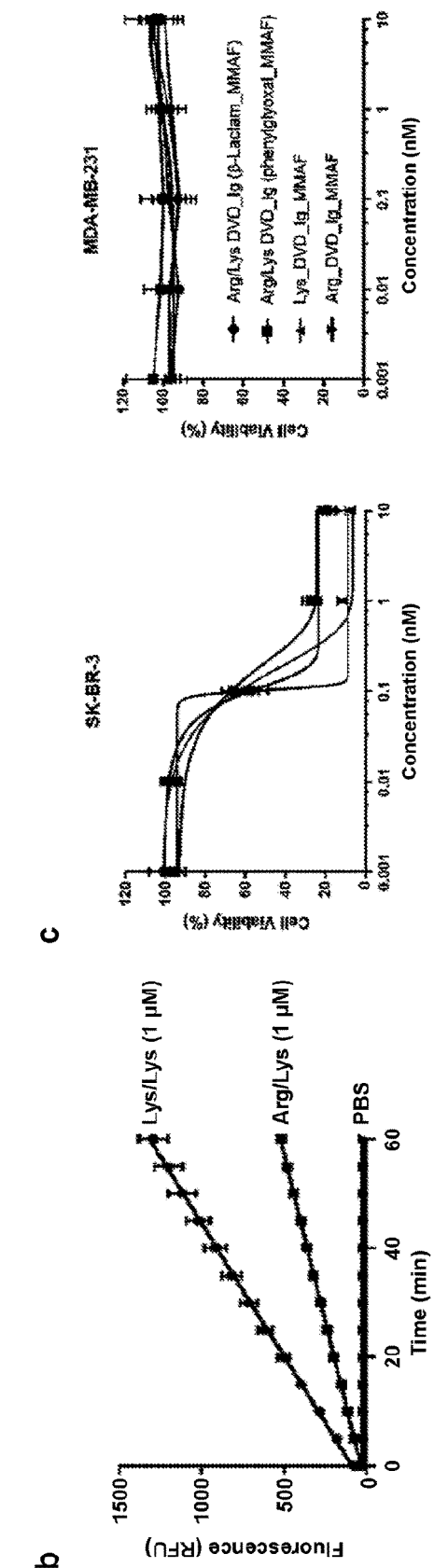
Fig. 10

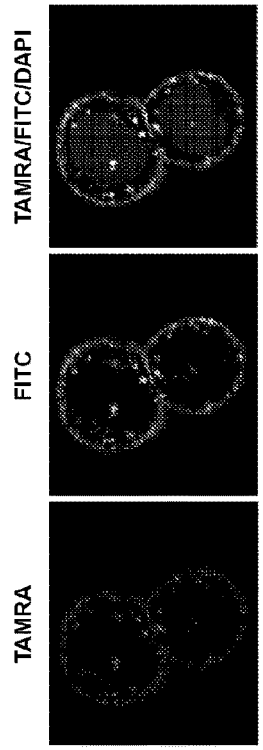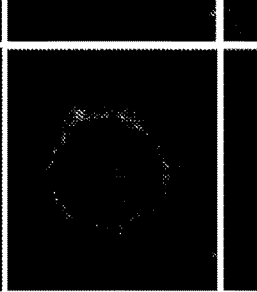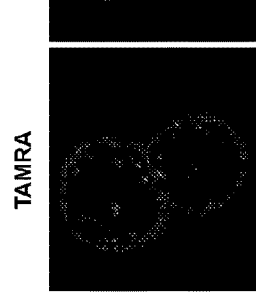
Fig. 14

ANTIBODY COMPOUNDS WITH REACTIVE ARGININE AND RELATED ANTIBODY DRUG CONJUGATES

CROSS-REFERENCE TO RELATED APPLICATIONS

This application is a national stage entry of PCT/US2019/055224 filed Oct. 8, 2019, which claims the benefit of priority to U.S. Provisional Patent Application No. 62/744,339 (filed Oct. 11, 2018). The full disclosure of the priority application is incorporated herein by reference in its entirety and for all purposes.

REFERENCE TO A SEQUENCE LISTING

The contents of the electronic sequence listing (580008SEQLST.TXT; Size: 13.9 KB, and Date of Creation: Jun. 3, 2024) is herein incorporated by reference in its entirety.

BACKGROUND OF THE INVENTION

Antibody drug conjugates (ADCs) consist of monoclonal antibodies connected to a potent cytotoxic payload via a linker. The concept of ADCs is the targeted delivery of a highly cytotoxic drug for selective (as opposed to systemic) chemotherapy, resulting in higher activity against malignant cells and lower toxicity toward healthy cells and tissues. The field has made great progress with the Food and Drug Administration (FDA) approvals of brentuximab vedotin (Adcetris®) for treating Hodgkin lymphoma and anaplastic large cell lymphoma, trastuzumab emtansine (Kadcyla®) for HER2 positive breast cancer, inotuzumab ozogamicin (Besponsa®) for acute lymphoblastic leukemia, and gemtuzumab ozogamicin (Mylotarg®) for acute myeloid leukemia. In addition to these four FDA-approved ADCs, more than 60 ADCs are currently investigated in clinical trials. The growing pipeline of ADCs also faces challenges. While the therapeutic index, i.e. the ratio of maximum tolerated dose and minimum effective dose, is generally higher for ADCs compared to chemotherapy (Panowski et al., *MAbs* 6:34-45, 2014), ADCs have also encountered on-target and off-target toxicities (Donaghy, MAbs 8:659-671, 2016). The four FDA-approved ADCs and the vast majority of ADCs in the clinical and preclinical pipeline randomly conjugate the drug to either surface lysine (Lys) or hinge cysteine (Cys) residues of the antibody, yielding complex mixtures of molecular species with varying drug-to-antibody ratios (DARs), pharmacokinetics, and pharmacodynamics.

The ADC field is moving toward homogeneous ADCs that, ideally, consist of a single molecular species with defined pharmacological properties. Homogeneous ADCs are highly defined compositions of mAb, linker, and drug, and typically have DARs of 2 or 4. Among various site-specific conjugation strategies including engineering cysteine residues (e.g., Junutula et al., Nat. Biotechnol. 26:925, 2008), unnatural amino acids (e.g., Axup et al., Proc. Natl. Acad. Sci. U.S.A. 109:16101, 2012), and enzymatic conjugation (e.g., Strop et al., Chem. Biol. 20:161, 2013), chemically programmable antibody (h38C2) have been utilized to generate a site-specific ADC in one-step conjugation as reported in Nanna et al., Nat. Commun. 8:1112, 2017. h38C2 is a humanized anti-hapten antibody binding to 1,3-diketone or β-lactam at a uniquely reactive lysine at the bottom of a hydrophobic pocket. The amino acid residues lining the hydrophobic pocket surround the reactive lysine residue and contribute to its unusual low $pK_a$ of 6.3 (Barbas et al., Science 278:2085, 1997).

Nevertheless, there is still a need in the art for a more efficient generation of ADCs with single and multiple payloads in a chemically defined manner. The instant invention is directed to this and other unmet needs.

SUMMARY OF THE INVENTION

In one aspect, the invention provides antibody compounds which contain a variant of catalytic antibody 38C2 (38C2 Arg) or antigen binding fragment thereof. Relative to antibody 38C2, the 38C2_Arg variant antibody contains a substitution of arginine for the reactive lysine residue (Lys99) in the hydrophobic cleft. In some antibody compounds of the invention, the catalytic antibody is a variant of humanized 38C2 (h38C2).

In some embodiments, the 38C2_Arg variant antibody or antigen binding fragment thereof contains heavy chain and light chain variable domain sequences respectively shown in SEQ ID NOs:1 and 2. Some antibody compounds of the invention are dual variable domain (DVD) antibody compounds or antigen-binding fragments thereof that contain (i) the 38C2_Arg variant or antigen binding fragment thereof, and (ii) a second antibody variable domain recognizing a target of interest. In some of these embodiments, the 38C2_Arg variant is positioned closer to the C-terminus in the antibody compound than the second variable domain. Some of these DVD antibody compounds are homodimeric molecules that contain Lys99Arg substitution in both antibody arms. Some other Some of these DVD antibody compounds of the invention are heterodimeric molecules that contain Lys99Arg substitution in only one antibody arm. In some embodiments, the DVD antibody compound contains a bispecific immunoglobulin molecule. Some DVD antibody compounds of the invention contain an antigen-binding fragment of a dual variable domain (DVD) compound that is a Fab, Fab', $F(ab')_2$, Fv or scFv. Some of these DVD antibody compounds are DVD-Fabs.

In some embodiments, the DVD antibody compound contains a chimeric immunoglobulin sequence or a humanized immunoglobulin sequence. In some DVD antibody compounds, the target of interest recognized by the second antibody variable domain is a tumor cell surface antigen. In some of these embodiments, the tumor cell surface antigen can be HER2, FOLR1, FCMR, CD138, CD79B, PSMA, BCMA, CD38, SLAMF7, Siglec-6, CD70, ROR1 or ROR2.

In another aspect, the invention provides antibody drug conjugates (ADCs) that contain at least one drug moiety conjugated to an antibody compound via a reactive arginine residue in the antibody compound. In these ADCs, the antibody compound contains a variant of catalytic antibody 38C2 (38C2 Arg) or antigen binding fragment thereof having a substitution of arginine for the reactive lysine residue in the hydrophobic cleft. In some embodiments, the catalytic antibody in the ADC is a variant of humanized 38C2 (h38C2). In some ADCs of the invention, the antibody compound is a dual variable domain (DVD) compound or an antigen-binding fragment thereof containing (i) the 38C2_Arg or antigen binding fragment thereof, and (ii) a second antibody variable domain recognizing a target of interest. In some ADCs of the invention, the drug moiety is conjugated to the antibody compound via a linker moiety. In some of these embodiments, the drug moiety is derivatized with the linker moiety prior to conjugation with the antibody compound. Some ADCs of the invention can utilize a cleavable linker to derivatize the drug moiety. In some specific embodiments, the employed linker can be phenylglyoxal (PGO), glyoxal (GO), or methylglyoxal (MGO).

In some ADCs of the invention, the DVD compound or an antigen-binding fragment thereof is a homodimeric molecule containing Lys99Arg substitution in both antibody arms. In some other embodiments, the DVD compound or an antigen-binding fragment thereof is a heterodimeric molecule containing Lys99Arg substitution in only one antibody arm. In some ADCs, the employed antibody compound is an antigen-binding fragment of a dual variable domain (DVD) antibody compound that is a Fab, Fab', F(ab')2, Fv or scFv. In some of these embodiments, the employed antibody compound is a DVD-Fab. In some embodiments, the target of interest recognized by the second antibody variable domain of the DVD antibody compound is a tumor cell surface antigen. In various embodiments, the tumor cell surface antigen can be HER2, FOLR1, FCMR, CD138, CD79B, PSMA, BCMA, CD38, SLAMF7, Siglec-6, CD70, ROR1 or ROR2.

In some ADCs of the invention, the conjugated drug moiety includes a cytotoxic agent or an siRNA. In some of these embodiments, the employed cytotoxic agent can be one selected from a toxin, a chemotherapeutic agent, a photoabsorber, an antibiotic, a radioactive isotope, a chelated radioactive isotope and a nucleolytic enzyme. In various embodiments, the conjugated drug moiety can include an auristatin, a dolastatin, a cemadotin, a camptothecin, an amanitin, a maytansinoid, a pyrrolobenzodiazepine, an indolinobenzodiazepine, a duocarmycin, an enediyne, a doxorubicin or a Fleximer. In some embodiments, at least one conjugated drug moiety is monomethyl auristatin F (MMAF).

In some ADCs of the invention, the 38C2_Arg or antigen binding fragment thereof contains heavy chain and light chain variable domain sequences respectively shown in SEQ ID NOs:1 and 2, and the target of interest is HER2. In some ADCs of the invention, the antibody compound is a DVD-Fab containing heavy chain and light chain sequences shown in SEQ ID NOs:5 and 7, respectively. In some ADCs of the invention, the antibody compound is a DVD-IgG1 containing heavy chain and light chain sequences shown in SEQ ID NOs:6 and 7, respectively. In some embodiments, the DVD-IgG1 compound in the ADC is a homodimeric molecule containing Lys99Arg substitution in both antibody arms. In some other embodiments, the DVD-IgG1 is a heterodimeric molecule containing Lys99Arg substitution in only one antibody arm. In some of these ADCs, two different drug moieties are conjugated to the two antibody arms of the heterodimeric DVD-IgG1 molecule.

In another aspect, the invention provides pharmaceutical compositions that contain an effective amount of the antibody drug conjugate described herein and optionally a pharmaceutically acceptable carrier. In another aspect, the invention provides methods for treating cancer in a subject. The methods entail administering to the subject in need of treatment a pharmaceutical composition disclosed herein.

A further understanding of the nature and advantages of the present invention may be realized by reference to the remaining portions of the specification and claims.

DESCRIPTION OF THE DRAWINGS

FIG. 5) and analyzed by SDS-PAGE followed by fluorescent imaging and Coomassie staining. (d) DVD-Fabs with h38C2 Arg or h38C2_Lys were pre-incubated with 10 equivalents of a β-lactam-hapten-azide (compound 3; FIG. 5) followed by incubation with 1 and 5 equivalents of compound 1.

FIG. 5. Phenylglyoxal and β-lactam derivatives. Compounds 1 and 2 are phenylglyoxal and β-lactam-hapten derivatives, respectively, of the red fluorescent dye TAMRA. Compound 3 is a β-lactam-hapten-azide derivative. Compounds 4 and 5 are phenylglyoxal and β-lactam-hapten derivatives, respectively, of the cytotoxic drug MMAF. Compound 6 is a β-lactam-hapten derivative of the near infrared fluorescent dye Cy7.

FIG. 14. Internalization and trafficking of heterodimeric DVD-IgG1 with two different payloads. HER2-positive SK-BR-3 cells (a) and HER2-negative MDA-MB-231 cells (b) were incubated with the MMAF (via Lys) and TAMRA (via Arg)-labeled HER2-targeting heterodimeric DVD-IgG1 for 4 h at 37° C. in the absence (top panel) and presence (middle panel) of endocytosis inhibitor phenylarsine oxide (PAO). The isotype control (lower panel) is a ROR2-targeting homodimeric DVD-IgG1 conjugated to TAMRA (via Lys). After the incubation, the cells were washed, fixed, blocked, permeabilized, incubated with FITC-conjugated goat anti-human IgG F(ab')₂ polyclonal antibodies, washed, stained with DAPI, and washed again before their analysis by confocal fluorescence microscopy.

DETAILED DESCRIPTION

I. Overview

Figure 1:
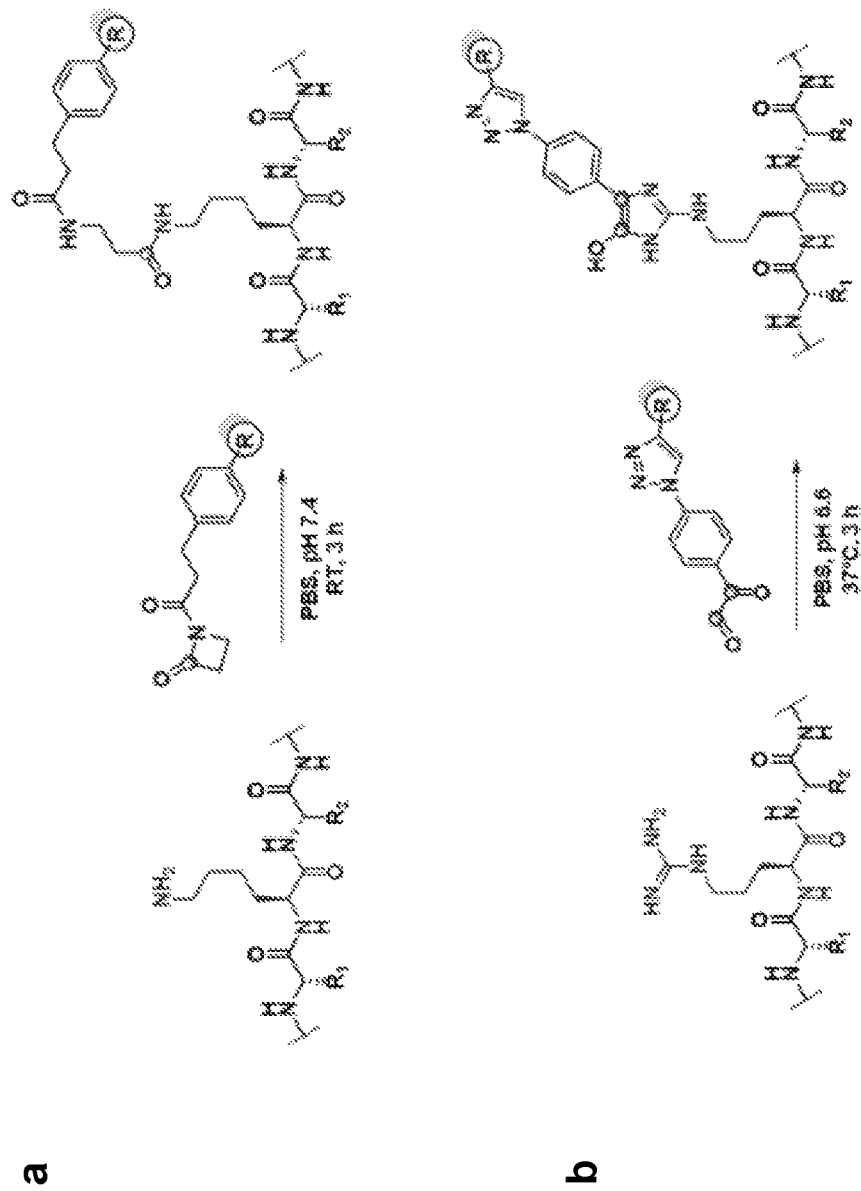
FIG. 1. Covalent conjugation of Lys and Arg. (a) Hapten-driven covalent conjugation of a β-lactam-hapten derivative to the reactive Lys residue of mAb h38C2_Lys. The side chains of the flanking Cys and Thr residues are shown as $R_1$ and $R_2$, respectively. (b) Hapten-driven covalent conjugation of a phenylglyoxal-triazole derivative to the reactive Arg residue of mAb 38C2_Arg.

The present invention is directed to ADCs that involve site-specific arginine conjugation of drug moieties to an antibody compound that contains a variant of catalytic antibody 38C2. It has been known in the art that arginine conjugation is not suitable for uses in site-specific bioconjugation due to a number of limitations. For example, arginine is a polar and charged amino acid which preferentially exists on the surface of the molecule to form hydrogen bonds with solvent. Also, the guanidine group of arginine represents a high $pK_a$ (~12.5), and it shows low nucleophilicity at physiological pH (deGruyter et al., Biochem. 56:3863-3873, 2017).

The present invention is predicated in part on the studies undertaken by the inventors to generate a distinctive environment for site-specific conjugation to an arginine residue inside the hydrophobic pocket of h38C2. These studies demonstrated for the first time that site-specific arginine conjugation can be utilized for the development of novel chemically programmed antibodies and novel antibody-drug conjugates. By way of exemplification, the inventors mutated the reactive lysine residue of h38C2 to an arginine residue and confirmed the structural integrity of the resulting monoclonal antibody h38C2_Arg by X-ray crystallography. It was shown that the introduced arginine residue in h38C2_Arg has unique reactivity that permits its selective and stable conjugation to phenylglyoxal derivatives. In addition, a phenylglyoxal derivative of MMAF was selectively conjugated to a HER2-targeting DVD that contained h38C2_Arg. This ADC compound demonstrated equal potency to the corresponding HER2-targeting DVD-ADC that was based on selective conjugation of a beta-lactam derivative of MMAF to the reactive lysine of wild-type h38C2. Furthermore, by combining a buried Lys residue with a buried Arg residue, the inventors generated a DVD-IgG1 with a wild-type h38C2 arm and an h38C2_Arg arm, providing an orthogonal one-pot assembly of highly homogeneous ADCs with two different payloads.

In accordance with these exemplified studies, the present invention provides novel site-specific arginine conjugated antibody drugs and related uses. As described herein, the ADCs of the invention contain at least one drug moiety that is conjugated to an antibody compound via a reactive arginine residue in the antibody compound. Preferably, the antibody compound in the ADCs of the invention contains a variant of catalytic antibody 38C2, or antigen binding fragment thereof, that contains a substitution of arginine for the reactive lysine residue in the hydrophobic cleft (38C2_Arg). In various embodiments, the antibody compound of the ADCs is a dual variable domain (DVD) compound or an antigen-binding fragment thereof that contains (i) the 38C2_Arg or antigen binding fragment thereof, and (ii) a second antibody variable domain recognizing a target of interest.

Before the present invention is described in greater detail, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The practice of the present invention can employ, unless otherwise indicated, conventional techniques of molecular biology (including recombinant techniques), microbiology, cell biology, biochemistry, and immunology, which are within the skill of the art. Such techniques are explained fully in the literature. See, e.g., Methods in Enzymology, Volume 289: Solid-Phase Peptide Synthesis, J. N. Abelson, M. I. Simon, G. B. Fields (Editors), Academic Press; $1^{st}$ edition (1997) (ISBN-13: 978-0121821906); U.S. Pat. Nos. 4,965,343, and 5,849,954; Sambrook et al., *Molecular Cloning: A Laboratory Manual*, Cold Spring Harbor Press, N.Y., ($3^{rd}$ ed., 2000); Brent et al., *Current Protocols in Molecular Biology*, John Wiley & Sons, Inc. (ringbou ed., 2003); Barbas et al., *Phage Display: A Laboratory Manual*, CSHL Press (2004); Davis et al., *Basic Methods in Molecular Biology*, Elsevier Science Publishing, Inc., New York, USA (1986); *Methods in Enzymology: Guide to Molecular Cloning Techniques*, Vol. 152, S. L. Berger and A. R. Kimmerl Eds., Academic Press Inc., San Diego, USA (1987); *Current Protocols in Protein Science* (CPPS) (John E. Coligan, et. al., ed., John Wiley and Sons, Inc.); *Current Protocols in Cell Biology* (CPCB) (Juan S. Bonifacino et. al. ed., John Wiley and Sons, Inc.); *Culture of Animal Cells: A Manual of Basic Technique and Specialized Applications*, R. Ian Freshney, Wiley Blackwell (7th edition, 2015); and *Animal Cell Culture Methods*, Jennie P. Mather and David Barnes editors, Academic Press ($1^{st}$ edition, 1998). The following sections provide additional guidance for practicing the compositions and methods of the present invention.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible. Although any methods and materials similar or equivalent to those described herein can also be used in the practice or testing of the present invention, representative illustrative methods and materials are now described.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "immunoglobulin" or "antibody" as used interchangeably herein refers to a basic 4-chain heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain has an N-terminus and a C-terminus, and also has regularly spaced intrachain disulfide bridges. Each H chain has at the N-terminus a variable domain ($V_H$) followed by three constant domains ($C_H1$, $C_H2$ and $C_H3$). Each L chain has at the N-terminus a variable domain ($V_L$) followed by one constant domain ($C_L$). The $V_L$ is aligned with the $V_H$ and the $C_L$ is aligned with the first constant domain of the heavy chain ($C_H1$). Particular amino acid residues are believed to form an interface between the L chain and H chain variable domains. The pairing of a $V_H$ and $V_L$ together forms a single antigen-binding site.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an immunoglobulin refers to the N-terminal domains of the H or L chain of the immunoglobulin. The variable domain of the H chain can be referred to as "$V_H$." The variable domain of the light chain can be referred to as "$V_L$." These domains are generally the most variable parts of an immunoglobulin and contain the antigen-binding sites.

The term "variable" refers to the fact that certain segments of the variable domains differ extensively in sequence among immunoglobulins. The V domain mediates antigen binding and defines specificity of a particular immunoglobulin for its particular antigen. However, the variability is not evenly distributed across the 110-amino acid span of most variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native H and L chains each comprise four FRs, largely adopting a n-sheet configuration, connected by three hypervariable regions, which form loops connecting, and in some cases forming part of, the n-sheet structure. The hypervariable regions in each chain are held together in close proximity by the FRs and, with the hypervariable regions from the other chain, contribute to the formation of the antigen-binding site of immunoglobulins (see Kabat et al., Sequences of Proteins of Immunological Interest, 5th Ed. Public Health Service, National Institutes of Health, Bethesda, MD. (1991)). The constant domains are not involved directly in binding an immunoglobulin to an antigen, but exhibit various effector functions, such as participation of the immunoglobulin in antibody dependent cellular cytotoxicity (ADCC), antibody-dependent cellular phagocytosis (ADCP), and complement-dependent cytotoxicity (CDC).

An "intact" immunoglobulin is one that comprises an antigen-binding site as well as a $C_L$ and at least H chain constant domains, $C_H1$, $C_H2$ and $C_H3$. The constant domains can be native sequence constant domains (e.g., human native sequence constant domains) or amino acid sequence variants thereof. An intact immunoglobulin can have one or more effector functions.

A "naked immunoglobulin" for the purposes herein is an immunoglobulin that is not conjugated to a drug moiety.

"Immunoglobulin fragments" comprise a portion of an intact immunoglobulin, preferably the antigen binding or variable region of the intact immunoglobulin. Examples of immunoglobulin fragments include, but are not limited to, Fab, Fab', F(ab')$_2$, and Fv fragments; diabodies; linear immunoglobulins (see U.S. Pat. No. 5,641,870, Example 2; Zapata et al., Protein Eng. 8(10): 1057-1062 [1995]); single-chain immunoglobulin molecules; and multispecific immunoglobulins formed from immunoglobulin fragments. In some embodiments, the immunoglobulin fragments include all possible alternate fragment formats. In some embodiments, the immunoglobulin fragments may be bispecific. In some embodiments, the immunoglobulin fragments may be bi-paratropic. In some embodiments, the immunoglobulin fragments may be trispecific. In some embodiments, the immunoglobulin fragments may be multimeric. In some embodiments, an immunoglobulin fragment comprises an antigen binding site of the intact immunoglobulin and thus retains the ability to bind antigen. In some embodiments, the immunoglobulin fragment contains single variable domains which have the ability to bind antigen. In some embodiments, the immunoglobulin fragments are further modified (not limited to peptide addition, pegylation, hesylation, glycosylation) to modulate activity, properties, pharmacokinetic behavior and in vivo efficacy.

Papain digestion of immunoglobulins produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain (CHI). Each Fab fragment is monovalent with respect to antigen binding, i.e., it has a single antigen-binding site. Pepsin treatment of an immunoglobulin yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the immunoglobulin hinge region. Fab'-SH is the designation herein for Fab' in which the cysteine residue(s) of the constant domains bear a free thiol group. F(ab')$_2$ immunoglobulin fragments originally were produced as pairs of Fab' fragments which have hinge cysteines between them. Other chemical couplings of immunoglobulin fragments are also known.

The Fc fragment comprises the carboxy-terminal portions of both H chains held together by disulfides. The effector functions of immunoglobulins are determined by sequences in the Fc region, which region is also the part recognized by Fc receptors (FcR) found on certain types of cells.

"Fv" is the minimum immunoglobulin fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the immunoglobulin. However, even a single variable domain (or half of an Fv comprising only three CDRs specific for an antigen) has the ability to recognize and bind antigen, although typically at a lower affinity than the entire binding site. When used herein in reference to a DVD immunoglobulin molecule, the term "Fv" refers to a binding fragment that includes both the first and the second variable domains of the heavy chain and the light chain.

"Single-chain Fv" also abbreviated as "sFv" or "scFv" are immunoglobulin fragments that comprise the $V_H$ and $V_L$ immunoglobulin domains connected into a single polypeptide chain. Preferably, the sFv polypeptide further comprises a polypeptide linker between the $V_H$ and $V_L$ domains which enables the sFv to form the desired structure for antigen binding. For a review of sFv, see Plückthun in *The Pharmacology of Monoclonal Antibodies*, vol. 113, Rosenburg and Moore eds., Springer-Verlag, New York, pp. 269-315 (1994); and *Antibody Engineering*, Borrebaeck ed., Oxford University Press (1995). When used herein in reference to a DVD immunoglobulin molecule, the term "scFv" refers to a binding fragment that includes both the first and the second variable domains of the heavy chain and the light chain.

As used herein, a "dual variable domain (DVD) compound" or a "dual variable domain (DVD) immunoconjugate" refers to compound that has a first and a second variable domain of immunoglobulins (include antigen-binding fragments of Ig such as Fab), and a drug moiety that is covalently conjugated to the second variable domain via a linker. The term "dual variable domain immunoglobulin" or "DVD-Ig" as used herein refers to an immunoglobulin molecule the H and L chains of which both include a second variable domain located adjacent to the first variable domain. The L chain of a DVD-Ig therefore includes, from N-terminus to C-terminus, the following domains: $V_L1$-$V_L2$-$C_L$. The H chain of a DVD-Ig therefore includes, from N-terminus to C-terminus, the following domains: $V_H1$-$V_H2$-$C_H1$-$C_H2$-$C_H3$. The pairing of a $V_L1$ and $V_H1$ together forms a first antigen-binding site. The pairing of a $V_L2$ and $V_H2$ together forms a second antigen binding site. In some embodiments, the DVD compound of the invention is DVD-Fab, which contains an immunoglobulin component that is an antigen binding fragment of Ig such as an Fab fragment as exemplified herein. General methods of making various DVD compounds of the invention are described in the art, e.g., Nanna et al., Nat. Commun. 8:1112, 2017.

Unless stated otherwise, the term "immunoglobulin" or "antibody" specifically includes native human and non-human IgG1, IgG2, IgG3, IgG4, IgE, IgA1, IgA2, IgD and IgM antibodies, including naturally occurring variants.

The term "native" with reference to a polypeptide (e.g., an antibody or immunoglobulin) is used herein to refer to a polypeptide having a sequence that occurs in nature, regardless of its mode of preparation. The term "non-native" with reference to a polypeptide (e.g., an antibody or immunoglobulin) is used herein to refer to a polypeptide having a sequence that does not occur in nature.

The term "polypeptide" is used herein in the broadest sense and includes peptide sequences. The term "peptide" generally describes linear molecular chains of amino acids containing up to about 30, preferably up to about 60 amino acids covalently linked by peptide bonds.

The term "monoclonal" as used herein refers to an antibody or immunoglobulin molecule (e.g., a DVD Ig molecule) obtained from a population of substantially homogeneous immunoglobulins, i.e., the individual immunoglobulins comprising the population are identical except for possible naturally occurring mutations that can be present in minor amounts. Monoclonal immunoglobulins are highly specific, being directed against a single antigenic site. Furthermore, in contrast to conventional (polyclonal) antibody preparations which typically include different antibodies directed against different determinants (epitopes), each monoclonal immunoglobulin is directed against a single determinant on the antigen. The modifier "monoclonal" indicates the character of the immunoglobulin as being obtained from a substantially homogeneous population of immunoglobulins, and is not to be construed as requiring production of the antibody by any particular method. For example, the monoclonal immunoglobulins in accordance with the present invention can be made by the hybridoma method first described by Kohler and Milstein (1975) Nature 256:495, or can be made by recombinant DNA methods (see, e.g., U.S. Pat. No. 4,816,567).

The monoclonal immunoglobulins herein specifically include "chimeric" immunoglobulins in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., rodent, e.g., murine or rabbit) immunoglobulins are immunoglobulins which contain minimal sequences derived from non-human immunoglobulin. For the most part, humanized immunoglobulins are human immunoglobulins (recipient antibody) in which residues from a hypervariable region of the recipient are replaced by residues from a hypervariable region of a non-human species (donor antibody) such as mouse, rat, hamster, rabbit, chicken, bovine or non-human primate having the desired specificity, affinity, and capacity. In some instances, Fv framework region (FR) residues of the human immunoglobulin are also replaced by corresponding non-human residues. Furthermore, humanized antibodies can comprise residues which are not found in the recipient antibody or in the donor antibody. These modifications are made to further refine antibody performance. In general, the humanized immunoglobulin will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized immunoglobulin optionally also will comprise at least a portion of an immunoglobulin constant region (Fc), typically that of a human immunoglobulin. For further details, see Jones et al. (1986) Nature 321:522-525; Riechmann et al. (1988) Nature 332:323-329; and Presta (1992) Curr. Op. Struct. Biol. 2:593-596.

The term "human immunoglobulin", as used herein, is intended to include immunoglobulins having variable and constant regions derived from human germline immunoglobulin sequences. The human immunoglobulins of the invention can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human immunoglobulin", as used herein, is not intended to include immunoglobulins in which CDR sequences derived from the germline of another mammalian species, such as a mouse, have been grafted onto human framework sequences.

An "isolated" immunoglobulin herein is one which has been identified and separated and/or recovered from a component of its natural environment in a recombinant host cell. Contaminant components of its natural environment are materials which would interfere with diagnostic or therapeutic uses for the immunoglobulin, and can include enzymes, hormones, and other proteinaceous or nonproteinaceous solutes, as well as undesired byproducts of the production. In some embodiments, an isolated immunoglobulin herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or non-reducing conditions using Coomassie blue or, preferably, silver stain. Ordinarily, an isolated immunoglobulin will be prepared by at least one purification step.

The term "specific binding" or "specifically binds to" or is "specific for" refers to the binding of a binding moiety to a binding target, such as the binding of an immunoglobulin to a target antigen, e.g., an epitope on a particular polypeptide, peptide, or other target (e.g. a glycoprotein target), and means binding that is measurably different from a non-specific interaction (e.g., a non-specific interaction can be binding to bovine serum albumin or casein). Specific binding can be measured, for example, by determining binding of a binding moiety, or an immunoglobulin, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_d$ for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an immunoglobulin) and its binding partner (e.g., an antigen). Unless indicated otherwise, as used herein, "binding affinity" refers to intrinsic binding affinity which reflects a 1:1 interaction between members of a binding pair (e.g., immunoglobulin and antigen). The affinity of a molecule X for its partner Y can generally be represented by the dissociation constant ($K_d$). For example, the $K_d$ can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "$K_d$" or "$K_d$ value" refers to a dissociation constant measured by a technique appropriate for the immunoglobulin and target pair, for example using surface plasmon resonance assays, for example, using a Biacore X100 or a Biacore T200 (GE Healthcare, Piscataway, N.J.) at 25° C. with immobilized antigen CM5 chips.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin.

The term "epitope" includes any molecular determinant capable of specific binding to an immunoglobulin. In certain aspects, epitope determinants include chemically active surface groupings of molecules such as amino acids, sugar side chains, phosphoryl, or sulfonyl, and, in certain aspects, can have specific three dimensional structural characteristics, and/or specific charge characteristics. An epitope is a region of an antigen that is bound by an immunoglobulin. A "binding region" is a region on a binding target bound by a binding molecule.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an immunoglobulin or trigger a cellular immune response. An immunogen refers to an antigen, which can elicit an immune response in an organism, particularly an animal, more particularly a mammal including a human. The term antigen includes regions known as antigenic determinants or epitopes, as defined above.

An "antigen-binding site" or "antigen-binding region" of an immunoglobulin of the present invention typically contains six complementarity determining regions (CDRs) within each variable domain, and which contribute in varying degrees to the affinity of the binding site for antigen. In each variable domain there are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs can be sufficient for binding to some binding targets. Thus, in some instances, the CDRs of a $V_H$ or a $V_L$ domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the immunoglobulins according to the current invention. In one aspect, Chinese hamster ovary (CHO) cells are used as host cells. In some embodiments, E. coli can be used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to a peptide or polypeptide sequence, i.e., the h38C2 antibody polypeptide sequences identified herein, is defined as the percentage of amino acid residues in a candidate sequence that are identical with the amino acid residues in the specific peptide or polypeptide sequence after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Treating" or "treatment" refers to both therapeutic treatment and prophylactic or preventative measures, wherein the object is to prevent or slow down (lessen) a targeted pathologic condition or disorder. Those in need of treatment include those already with the disorder, as well as those prone to have the disorder, or those in whom the disorder is to be prevented. For example, a subject or mammal is successfully "treated" for cancer, if, after receiving a therapeutic amount of a subject immunoconjugate according to the methods of the present invention, the subject shows observable and/or measurable reduction in or absence of one or more of the following: reduction in the number of cancer cells or absence of the cancer cells; reduction in the tumor size; inhibition (i.e., slowing to some extent and preferably stopping) of cancer cell infiltration into peripheral organs, including the spread of cancer into soft tissue and bone; inhibition (i.e., slowing to some extent and preferably stopping) of tumor metastasis; inhibition, to some extent, of tumor growth; and/or relief to some extent of one or more of the symptoms associated with the specific cancer; reduced morbidity and/or mortality, and improvement in quality of life issues.

III. Antibody Compounds with Reactive Arg Residue(s)

The invention provides antibody compounds that contain a variant of catalytic antibody 38C2 or antigen-binding fragments thereof. The 38C2 catalytic antibody is well known in the art and has been well characterized in, e.g., U.S. Pat. No. 8,252,902. The heavy chain variable region of the 38C2 antibody includes a single, uniquely reactive lysine residue (Lys99) that can react with a linker, thereby providing an attachment point for conjugation with a drug moiety. As such, immunoglobulin molecules that include a variable domain of the 38C2 antibody contain two such attachment points (one on each heavy chain) that can be used for conjugation with a drug moiety. Once a reactive lysine residue has been conjugated to a linker, the binding functionality of the 38C2 variable domain is lost, meaning that the variable domain no longer exhibits catalytic activity.

The 38C2 variant antibodies of the invention contain an arginine substitution for this reactive lysine residue in the hydrophobic cleft, which provides an attachment point for drug conjugation that is different from the reactive lysine residue. For full length antibodies (e.g., IgG) or dimeric antibody fragments (e.g., F(ab')$_2$), the substitution can be present in one or both antibody arms or antigen-binding sites. With an appropriate linker moiety, the engineered Arg residue in the 38C2 variant (38C2_Arg) is able to react with the drug moiety to form an ADC. Thus, in some embodiments, both variant domains of the antibody have the reactive Lys residue replaced with Arg. In some embodiments, the 38C2_Arg variant antibody can contain a reactive Arg residue in one of its two binding arms and a reactive Lys residue in the other binding arm. In some embodiments, the 38C2_Arg variant employed in the ADCs of the invention is a chimeric antibody. In some other embodiments, the 38C2_Arg variant used in the invention is a humanized antibody (h38C2_Arg). In various embodiments, the 38C2_Arg variant can contain a humanized light sequence, a humanized heavy chain sequence or both. The ADCs of the invention are homogeneous due to site-specific conjugation to the reactive Arg and Lys residues.

Antibody compounds containing a variant 38C2 antibody with the reactive Lys residue replaced by Arg can be readily produced via routinely practiced methods, e.g., recombinant expression as exemplified herein. As specific exemplification, the heavy and light chain variant domain sequences of a humanized 38C2_Arg variant (h38C2_Arg) suitable for the invention are shown in SEQ ID NOs:1 and 2, respectively. The substituted Arg residue at position 99 is underlined in the heavy chain sequence (SEQ ID NO:1). It is noted that the light chain variable domain sequence of this variant is identical to the light chain variable domain sequence of humanized 38C2 antibody (h38C2) known in the art.

V$_H$ of h38C2_Arg (SEQ ID NO: 1)
EVQLVESGGGLVQPGGSLRLSCAASGFTFSNYWMSWVRQSPEKGLEWVSE

IRLRSDNYATHYAESVKGRFTISRDNSKNTLYLQMNSLRAEDTGIYYCRT

YFYSFSYWGQGTLVTVSS

V$_K$ of h38C2_Arg (SEQ ID NO: 2)
ELQMTQSPSSLSASVGDRVTITCRSSQSLLHTYGSPYLNWYLQKPGQSPK

LLIYKVSNRFSGVPSRFSGSGSGTDFTLTISSLQPEDFAVYFCSQGTHLP

YTFGGGTKVEIK

In various embodiments, the antibody compounds of the invention can contain one or two reactive Arg residues noted above, and with a heavy chain and/or light chain sequences that are substantially identical to the exemplified sequences. For example, other than the presence of the reactive Arg residue(s), the heavy chain and light chain variable domain amino acid sequences of the antibody compounds of the invention can be of at least about 80% identical, alternatively at least about 81%, 82%, 83%, 84%, 85%, 86%, 87%, 88%, 89%, 90%, 91%, 92%, 93%, 94%, 95%, 96%, 97%, 98%, or 99% identical to SEQ ID NOs:1 and 2, respectively.

IV. Antibody Conjugated Drugs with Site-Specific Arg Conjugation

The invention also provides antibody conjugated drugs (ADCs) that contain at least one drug moiety that is site-specifically conjugated to an antibody compound via an engineered arginine residue. Preferably, the antibody compound is a variant derived from catalytic antibody 38C2 noted above. In some embodiments, the antibody compound is a homodimeric molecule that contains the Lys99Arg substitution in both antibody arms. In these embodiments, the ADCs can contain the same drug moiety that is conjugated to the engineered Arg residue in both arms of the antibody compound. In some embodiments, the antibody compound is a heterodimeric molecule that contains the Lys99Arg substitution in just one antibody arm. Heavy chain heterodimerization for such molecules can be accomplished, e.g., via knobs-into-holes mutations as exemplified herein. In these embodiments, the ADCs can contain a first drug moiety that is conjugated to the engineered Arg residue in one antibody arm and a second drug moiety that is conjugated to the reactive Lys residue in the other antibody arm. In some embodiments, the antibody compound in the ADCs is a humanized 38C2_Arg antibody (h38C2_Arg) or antigen-binding fragment thereof alone. In some other embodiments, the antibody compound is a dual variable domain (DVD) compound (DVD-Fab or DVD-Ig as exemplified herein) or a bispecific antibody that harbors 38C2_Arg. Thus, the antibody compound in some ADCs of the invention is a DVD-Ig that contains a first variable domain that binds to a target antigen (e.g., a tumor cell surface antigen or receptor) and a second variable domain (38C2_Arg) that allows site-specific attachment of a linker molecule or linker-derivatized drug moiety.

Once the variant 38C2 antibody containing reactive Arg is generated, DVD-Ig antibody compounds containing the 38C2_Arg antibody can be produced in accordance with methods that have been reported in the literature. See, e.g., Nanna et al., Nat. Commun. 8:1112, 2017; and WO2017/049139. The DVD-Ig to which drug moieties are conjugated contains a first variable domain, the 38C2 variant, for attachment of drug moieties, and a second variable domain for binding to a target of interest. When the antibody component of the ADCs has an intact antibody structure, the DVD-Ig typically contains two arms, each consisting of a light chain and a heavy chain. Each light chain and each heavy chain includes an N-terminus and a C-terminus. In some embodiments, the two arms of the DVD-Ig are identical, i.e., with the light chains being identical and the heavy chains being identical. For example, some of these embodiments are directed to homodimeric DVD compounds (e.g., homodimeric HER2 targeting DVD-Ig molecules as exemplified herein) that harbor a variant 38C2 antibody containing two h38C2_Arg arms. In some other embodiments, the two arms of the DVD-Ig can be different. For example, some of the DVD compounds (e.g., heterodimeric HER2 targeting DVD-Ig as exemplified herein) can be heterodimeric in that the variant 38C2 antibody component of the DVD compounds contains one h38C2_Lys arm and one h38C2_Arg arm. In some embodiments, the 38C2 variant domain can be positioned closer to the C-terminus of the DVD-Ig than the second variable domain. In some other embodiments, the 38C2 variant domain can be positioned closer to the N-terminus of the DVD-Ig than the second variable domain.

In some embodiments, the DVD-Ig contains 38C2_Arg as the first variable domain for conjugating the drug moieties and a second variable domain that binds to a target of interest (e.g., a target antigen or receptor). In some of these ADCs, the reactive Arg is present in both arms of the 38C2-Arg variant and identical drug moieties are conjugated to the two arms of the antibody compound. In some other ADCs, the reactive lysine residue in only one arm of the 38C2 variant antibody is replaced with an arginine residue. These ADCs contain both a reactive Arg and a reactive Lys in the two arms, to which 2 different drug moieties are respectively conjugated via appropriate linkers, as exemplified herein.

Immunoglobulins of variant types or subtypes can be used in the constructions of the DVD-Ig antibody compounds of the invention. For example, the light chain can be a kappa light chain or a lambda light chain. Depending on the Fc domain, the heavy chain can be that from an IgG (such as an IgG1, IgG2, IgG3 or IgG4), IgA (such as an IgA1 or IgA2), IgM, IgE or IgD antibody. For example, in some aspects, an immunoglobulin belongs to the IgG class, and the heavy chain comprises a γ heavy chain. In some embodiments, an immunoglobulin belongs to the IgG1 class, and the heavy chain comprises a γ1 heavy chain. In some embodiments, an immunoglobulin belongs to the IgG2 class, and the heavy chain comprises a γ2 heavy chain. In some embodiments, an immunoglobulin belongs to the IgG3 class, and the heavy chain comprises a γ3 heavy chain. In some embodiments, an immunoglobulin belongs to the IgG4 class, and the heavy chain comprises a γ4 heavy chain. In some embodiments, an immunoglobulin belongs to the IgA class, and a heavy chain comprises an a heavy chain. In some embodiments, an immunoglobulin belongs to the IgA1 class, and a heavy chain comprises a a1 heavy chain. In some embodiments, an immunoglobulin belongs to the IgA2 class, and a heavy chain comprises a α2 heavy chain. In some embodiments, an immunoglobulin belongs to the IgD class, and a heavy chain comprises a δ heavy chain. In some embodiments, an immunoglobulin belongs to the IgE class, and a heavy chain comprises an E heavy chain. In some embodiments, an immunoglobulin belongs to the IgM class, and a heavy chain comprises a μ heavy chain.

In various embodiments, the first and second variable domains of the DVD-Ig antibody compounds are linked along their light chain or heavy chain by a peptide linker sequence. A peptide linker sequence can be a single amino acid or a polypeptide sequence. A number of linkers that can be employed in the present invention are described in the art, e.g., WO2017/049139 and U.S. Pat. No. 7,612,181. Some specific examples of suitable linkers include ASTKGP (SEQ ID NO:3) and TVAAPSVFIFPP (SEQ ID NO:4).

The second variable domain of the DVD-Ig in the ADCs of the invention can be any antibody or antigen-binding fragment that specifically recognizes a target polypeptide or target antigen of interest. For example, it can be an antibody, antibody domain or antigen-binding fragment that recognizes an antigen on a tumor cell. Immunoglobulins can exert antitumor effects by inducing apoptosis, redirected cytotoxicity, interfering with ligand-receptor interactions, or preventing the expression of proteins that are critical to a neoplastic phenotype. In addition, immunoglobulins can target components of the tumor microenvironment, perturbing vital structures such as the formation of tumor-associated vasculature. Immunoglobulins can also target receptors whose ligands are growth factors, such as the epidermal growth factor receptor, thus inhibiting binding of natural ligands that stimulate cell to targeted tumor cells. Alternatively, immunoglobulins can induce ADCC, ADCP or CDC.

One of skill in the art will realize that tumor-associated antigens are known for virtually any type of cancer. Specific tumor-associated binding targets that can be targeted by the second variable domain of a subject DVD immunoglobulin molecule include HER2 (ERBB2) as exemplified herein. Other examples include, but are not limited to, FOLR1, FOLR2, CD138, CD19, CD79A, CD79B, ROR1, ROR2, FCMR, CS1, GPA33, MSLN, CD52, CD20, CD3, CD4, CD5, CD8, CD20, CD21, CD22, CD23, CD30, CD33, CD38, CD44, CD56, CD70, BCMA, Siglec-1, Siglec-4, Siglec-5, Siglec-6, Siglec-7, Siglec-8, Siglec-9. PSMA, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR (ERBB1), HER3 (ERBB3), HER4 (ERBB4), ENO1, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NROB1, NROB2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB21P, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAI1, COL4A3, IL8, LAMA5, NRP1, NRP2, STAB1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MK167 (Ki-67), NGFB (NGF), NGFR, NME1 (NM23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MAC-MARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94).

The amino acid sequences of the second variable domain of the DVD-Ig in the ADCs of the invention can include chimeric, humanized, or human amino acid sequences. Any suitable combination of such sequences can be incorporated into the second variable domain of the DVD-Ig antibody compounds of the invention.

Antigen-binding variable region sequences can be selected from various monoclonal antibodies capable of binding specific targets and well known in the art. These include, but are not limited to anti-TNF antibody (U.S. Pat. No. 6,258,562), anti-IL-12 and or anti-IL-12p40 antibody (U.S. Pat. No. 6,914,128); anti-IL-18 antibody (US 2005/0147610 A1), anti-C5, anti-CBL, anti-CD147, anti-gp120, anti-VLA4, anti-CD11a, anti-CD18, anti-VEGF, anti-CD40L, anti-Id, anti-ICAM-1, anti-CXCL13, anti-CD2, anti-EGFR, anti-TGF-beta 2, anti-E-selectin, anti-Fact VII, anti-Her2/neu, anti-F gp, anti-CD11/18, anti-CD14, anti-ICAM-3, anti-CD80, anti-CD4, anti-CD3, anti-CD23, anti-beta2 integrin, anti-alpha4beta7 integrin, anti-alpha4beta1 integrin, anti-alphavbeta3 integrin, anti-alphavbeta5 integrin, anti-CD52, anti-HLA DR, anti-CD22, anti-Siglec-1, anti-Siglec-4, anti-Siglec-5, anti-Siglec-6, anti-Siglec-7, anti-Siglec-8, anti-Siglec-9, anti-PSMA, anti-BCMA, anti-ROR1, anti-ROR2, anti-DLL3, anti-FOLR1, anti-FOLR2, anti-CD5, anti-SLAMF7, anti-FCMR, anti-CD20, anti-MIF, anti-CD64 (FcµR1), anti-TCR alpha beta, anti-CD2, anti-Hep B, anti-CA 125, anti-EpCAM, anti-gp120, anti-CMV, anti-gpIIbIIIa, anti-IgE, anti-CD25, anti-CD33, anti-HLA, anti-VNRintegrin, anti-IL-1alpha, anti-IL-1beta, anti-IL-1 receptor, anti-IL-2 receptor, anti-IL-4, anti-IL4 receptor, anti-IL5, anti-IL-5 receptor, anti-IL-6, anti-IL-8, anti-IL-9, anti-IL-13, anti-IL-13 receptor, anti-IL-17, and anti-IL-23. See, e.g., Beck et al., Nat Rev Drug Discov. 2017, 16:315-337; Carter and Lazar, Nat Rev Drug Discov. 2018, 17:197-223; Kaplon and Reichert, MAbs. 2018, 10:183-203; Reichert, MAbs. 2017, 9:167-181; Reichert, MAbs. 2016, 8:197-204; and Presta L G., J. Allergy Clin. Immunol. 2005, 116:731-6.

Antigen-binding variable region sequences can also be selected from various therapeutic antibodies approved for use, in clinical trials, or in development for clinical use. Such therapeutic antibodies include, but are not limited to, RITUXAN®, IDEC/Genentech/Roche) (see for example U.S. Pat. No. 5,736,137), a chimeric anti-CD20 antibody approved to treat non-Hodgkin's lymphoma; HUMAX-CD20®, an anti-CD20 developed by Genmab, an anti-CD20 antibody described in U.S. Pat. No. 5,500,362, AME-133 (Applied Molecular Evolution), hA20 (Immunomedics, Inc.), HumaLYM (Intracel), and PR070769 (PCT/US2003/040426, entitled "Immunoglobulin Variants and Uses Thereof"), trastuzumab (HERCEPTIN®, Genentech) (see for example U.S. Pat. No. 5,677,171), a humanized anti-HER2 antibody approved to treat breast cancer; pertuzumab (rhuMab-2C4, OMNITARG®), developed by Genentech; an anti-HER2 antibody described in U.S. Pat. No. 4,753,894; cetuximab (ERBITUX®, Imclone) (U.S. Pat. No. 4,943,533; PCT WO 96/40210), a chimeric anti-EGFR antibody; ABX-EGF (U.S. Pat. No. 6,235,883), developed by Abgenix-Immunex-Amgen; HUMAX-EGFR™ (U.S. Ser. No. 10/172,317), developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. Nos. 5,891,996; 6,506,883; Mateo et al, 1997, Immunotechnology, 3(1):71-81); mAb-806 (Ludwig Institute for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Scancell) (PCT WO 01/88138); alemtuzumab (CAMPATH®, Millennium), a humanized monoclonal antibody previously approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (ZEVALIN®), an anti-CD20 antibody developed by IDEC/Schering AG, gemtuzumab ozogamicin (MYLOTARG®), an anti-CD33 (p67 protein) antibody developed by Celltech/Wyeth, alefacept (AMEVIVE®), an anti-LFA-3 Fc fusion developed by Biogen), abciximab (REOPRO®), developed by Centocor/Lilly, basiliximab (SIMULECT®), developed by Novartis, palivizumab (SYNAGIS®), developed by Medimmune, infliximab (REMICADE®), an anti-TNFalpha antibody developed by Centocor, adalimumab (HUMIRA®), an anti-TNFalpha antibody developed by Abbott, HUMICADE®, an anti-TNFalpha antibody developed by Celltech, etanercept (ENBREL®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, ANTEGREN® (natalizumab), an anti-alpha-4-beta-1 (VLA4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-02 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LYMPHOSTAT-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., AVASTIN® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, XOLAIR® (Omalizumab), an anti-IgE antibody being developed by Genentech, RAPTIVA® (Efalizumab), an anti-CD11a antibody being developed by Genentech and Xoma, MLN-02 Antibody (formerly LDP-02), being developed by Genentech and Millennium Pharmaceuticals, HUMAX CD4®, an anti-CD4 antibody being developed by Genmab, HUMAX™-IL15, an anti-IL15 antibody being developed by Genmab and Amgen, HUMAX™-Inflam, being developed by Genmab and Medarex, HUMAX™-Cancer, an anti-Heparanase I antibody being developed by Genmab and Medarex and Oxford GlycoSciences, HUMAX™-Lymphoma, being developed by Genmab and Amgen, HUMAX™-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-CIDE® (labetuzumab), an anti-carcinoembryonic antigen (CEA) antibody being developed by Immunomedics, LYMPHOCIDE® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, OSIDEM® (IDM-1), and anti-Her2 antibody being developed by Medarex and Immuno-Designed Molecules, HUMAX®-CD4, an anti-CD4 antibody being developed by Medarex and Genmab, HuMax-IL15, an anti-IL15 antibody being developed by Medarex and Genmab, CNTO 148, an anti-TNFa antibody being developed by Medarex and Centocor/J & J, CNTO 1275, an anti-cytokine antibody being developed by Centocor/J & J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, NUVION® (visilizumab), an anti-CD3 antibody being developed by Protein Design Labs, HUZAF®, an anti-gamma interferon antibody being developed by Protein Design Labs, Anti-a 5β1 Integrin, being developed by Protein Design Labs, anti-IL-12, being developed by Protein Design Labs, ING-1, an anti-Ep-CAM antibody being developed by Xoma, XOLAIR® (Omalizumab) a humanized anti-IgE antibody developed by Genentech and Novartis, and MLN01, an anti-Beta2 integrin antibody being developed by Xoma. In some embodiments, the antigen-binding variable region sequences can be derived from any of the antibody drugs that have been approved in various therapies as shown in Table 1.

TABLE 1

FDA-approved and marketed antibody-based cancer therapy

| Name | Format | Payload | Target | Cancer | FDA approval |
|---|---|---|---|---|---|
| rituximab (Rituxan ®) | chimeric mouse/human IgG1κ | none | CD20 | B-NHL, CLL | 1997, 2010 |
| trastuzumab (Herceptin ®) | humanized IgG1κ | none | HER2 | breast, stomach | 1998, 2010 |
| ibritumomab tiuxetan (Zevalin ®) | mouse IgG1κ | $^{90}Y$ | CD20 | B-NHL | 2002 |
| cetuximab (Erbitux ®) | chimeric mouse/human IgG1κ | none | EGFR | colorectal, h & n | 2004, 2006 |
| bevacizumab (Avastin ®) | humanized IgG1κ | none | VEGF | colorectal, lung, brain, kidney, cervical, ovarian, fallopian tube, peritoneal | 2004-2014, 2018 |
| panitumumab (Vectibix ®) | human IgG2κ | none | EGFR | colorectal | 2006 |
| ofatumumab (Arzerra ®) | human IgG1κ | none | CD20 | CLL | 2009 |
| ipilimumab (Yervoy ®) | human IgG1κ | none | CTLA4 | melanoma, kidney, MSI-H/dMMR colorectal | 2011, 2018 |

TABLE 1-continued

FDA-approved and marketed antibody-based cancer therapy

| Name | Format | Payload | Target | Cancer | FDA approval |
|---|---|---|---|---|---|
| brentuximab vedotin (Adcetris ®) | chimeric mouse/human IgG1κ | MMAE | CD30 | HL, T-NHL | 2011 |
| pertuzumab (Perjeta ®) | humanized IgG1κ | none | HER2 | breast | 2012 |
| ado-trastuzumab emtansine (Kadcyla ®) | humanized IgG1κ | DM1 | HER2 | breast | 2013 |
| obinutuzumab (Gazyva ®) | humanized IgG1κ (glycoengineered Fc) | none | CD20 | CLL, B-NHL | 2013, 2017 |
| ramucirumab (Cyramza ®) | human IgG1κ | none | VEGFR2 | stomach, colorectal | 2014, 2015 |
| pembrolizumab (Keytruda ®) | humanized IgG4κ | none | PD1 | melanoma, lung, h & n, bladder, HL, MSI-H/dMMR cancers, stomach, cervical, B-NHL | 2014-2018 |
| blinatumomab (Blincyto ®) | mouse (scFv)$_2$ (BiTE) | none | CD19 × CD3 | ALL | 2014 |
| nivolumab (Opdivo ®) | human IgG4κ | none | PD1 | melanoma, lung, kidney, HL, h & n, bladder, MSI-H/dMMR colorectal, liver | 2014-2018 |
| dinutuximab (Unituxin ®) | chimeric mouse/human IgG1κ | none | GD2 | neuroblastoma | 2015 |
| daratumumab (Darzalex ®) | human IgG1κ | none | CD38 | multiple myeloma | 2015 |
| necitumumab (Portrazza ®) | human IgG1κ | none | EGFR | lung | 2015 |
| elotuzumab (Empliciti ®) | humanized IgG1κ | none | SLAMF7 | multiple myeloma | 2015 |
| atezolizumab (Tecentriq ®) | humanized IgG1κ (aglycosylated Fc) | none | PDL1 | bladder, lung | 2016 |
| olaratumab (Lartruvo ®) | human IgG1κ | none | PDGFRA | sarcoma | 2016 |
| avelumab (Bavencio ®) | human IgG1λ | none | PDL1 | Merkel cell carcinoma, bladder | 2017 |
| durvalumab (Imfinzi ®) | human IgG1κ (engineered Fc) | none | PDL1 | bladder, lung | 2017, 2018 |
| inotuzumab ozogamicin (Besponsa ®) | humanized IgG4κ | calicheamicin | CD22 | ALL | 2017 |
| tisagenlecleucel (Kymriah ®) | mouse scFv-based CAR-T | T cell | CD19 | ALL, B-NHL | 2017, 2018 |
| gemtuzumab ozogamicin (Mylotarg ®) | humanized IgG4κ | calicheamicin | CD33 | AML | 2017 |
| bevacizumab-awwb (Mvasi ®) | humanized IgG1κ | none | VEGF | colorectal, lung, brain, kidney, cervical | 2017 |
| axicabtagene ciloleucel (Yescarta ®) | mouse scFv-based CAR-T | T cell | CD19 | B-NHL | 2017 |
| trastuzumab-dkst (Ogivri ®) | humanized IgG1κ | none | HER2 | breast, stomach | 2017 |
| mogamulizumab-kpkc (Poteligeoi ®) | humanized IgG1κ (afucosylated Fc) | none | CCR4 | T-NHL | 2018 |
| moxetumomab pasudotox-tdfk (Lumoxiti ®) | mouse dsFv | bacterial toxin | CD22 | B-NHL | 2018 |
| cemiplimab-rwlc (Libtayo ®) | human IgG4κ (S228P hinge) | none | PD1 | cutaneous squamous cell carcinoma | 2018 |

The DVD-Ig antibody compound in the ADCs of the can encompass chimeric, humanized and human immunoglobulin sequences, and in some aspects, can contain any mixture thereof. In some embodiments, it can be modified with respect to effector function, e.g., so as to enhance ADCC, ADCP or CDC of the immunoglobulin. This can be achieved by introducing one or more amino acid substitutions in an Fc region of an immunoglobulin. Alternatively or additionally, cysteine residue(s) can be introduced in the Fc region, thereby allowing inter-chain disulfide bond formation in this region. An immunoglobulin thus generated can have improved internalization capability and/or increased ADCC, ADCP or CDC. See Caron et al., J. Exp Med. 176:1191-1195 (1992) and Shopes, B. J. Immunol. 148:2918-2922 (1992). To increase a serum half-life of an immunoglobulin, a salvage receptor binding epitope can be incorporated into an immunoglobulin (especially an immunoglobulin fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

As exemplification, the invention provides DVD-Ig and DVD-Fab containing 38C2_Arg for specifically targeting tumor antigen HER2. These DVD compounds contain a variable domain that binds to HER2 and a humanized 38C2_Arg variable domain as the second variable domain. The variable domains can be connected on each light and heavy chain with a peptide linker sequence, e.g., ASTKGP (SEQ ID NO: 3). To facilitate recombinant protein production, a signal peptide sequence, e.g., MDWTWRILFLVAAATGAHS (SEQ ID NO:8), can be placed at the N-terminus of the heavy and light chain sequences. The light chain amino acid sequence of the DVD-Ig and DVD-Fab molecules (trastuzumab V./ASTKGP/h38C2_Arg Vκ/$C_κ$) exemplified herein, minus the signal peptide, is shown in SEQ ID NO:7. The heavy chain amino acid sequence of the DVD-Fab molecule (trastuzumab $V_H$/ASTKGP/h38C2_Arg $V_H$/$C_{γ1}$1), minus the signal peptide, is shown in SEQ ID NO:5. The heavy chain amino acid sequence of the exemplified DVD-Ig molecule (trastuzumab $V_H$/ASTKGP/ h38C2_Arg $V_H$/$C_{γ1}$1-hinge$_{γ1}$-$C_{γ1}$2-$C_{γ1}$3), minus the signal peptide, is shown in SEQ ID NO:6. The linker sequence separating the two variable domains is underlined in these sequences. Constant region sequences are italicized in the sequences.

```
Heavy chain of HER2 targeting DVD-Fab
                                    (SEQ ID NO: 5)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPEVQLVESGGGLVQPGGSLRLSCAA

SGFTFSNYWMSWVRQSPEKGLEWVSEIRLRSDNYATHYAESVKGRFTISR

DNSKNTLYLQMNSLRAEDTGIYYCRTYFYSFSYWGQGTLVTVSSASTKGP

SVFPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSC

Heavy chain of HER2 targeting DVD-IgG1
                                    (SEQ ID NO: 6)
EVQLVESGGGLVQPGGSLRLSCAASGFNIKDTVIHWVRQAPGKGLEWVAR

IVPTNGYTRYADSVKGRFTISADTSKNTAYLQMNSLRAEDTAVYYCSRWG
```

```
-continued
GDGFYAMDYWGQGTLVTVSSASTKGPEVQLVESGGGLVQPGGSLRLSCAA

SGFTFSNYWMSWVRQSPEKGLEWVSEIRLRSDNYATHYAESVKGRFTISR

DNSKNTLYLQMNSLRAEDTGIYYCRTYFYSFSYWGQGTLVTVSSASTKGP

SVFPLAPSSKSTSGGTAALGCLVKDYFPEPVTVSWNSGALTSGVHTFPAV

LQSSGLYSLSSVVTVPSSSLGTQTYICNVNHKPSNTKVDKRVEPKSCDKT

HTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVF

SCSVMHEALHNHYTQKSLSLSPGA

Light chain of HER2 targeting DVD-Fab and DVD-IgG1
                                    (SEQ ID NO: 7)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKASTKGPELQMTQSPSSLSASVGDRVTITCRSSQSLLHTYGSPY

LNWYLQKPGQSPKLLIYKVSNRFSGVPSRFSGSGSGTDFTLTISSLQPED

FAVYFCSQGTHLPYTFGGGTKVEIKRTVAAPSVFIFPPSDEQLKSGTASV

VCLLNNEYPREAKVQWKVDNALQSGNSQESVTEQDSKDSTYSLSSTLTLS

KADYEKHKVYACEVTHQGLSSPVTKSENRGEC
```

In various embodiments, in addition to having Arg substitution for the reactive Lys residue in one or both arms of the 38C2 component, the HER2-targeting DVD compounds of the invention can contain a light chain amino acid sequence that is substantially similar to SEQ ID NO: 7, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:7. Alternatively or additionally, the HER2-targeting DVD compounds can contain a heavy chain amino acid sequence that is substantially similar to SEQ ID NO:6 or 7, for example, has at least about 80% amino acid sequence identity, alternatively has at least about 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:6 or 7.

V. Linker Moieties for Conjugating Drugs

The drug moieties in the antibody conjugate drugs (ADCs) of the invention are typically conjugated in a site-specific manner to the 38C2_Arg antibody via an appropriate linker sequence or linker moiety. The linkers serve to attach the cargo moiety (e.g., a drug moiety) to the DVD-Ig, and can employ any suitable chemistry. Various types of linker functionality can be included in the ADCs of the invention, including but not limited to cleavable linkers, and non-cleavable linkers, as well as reversible linkers and irreversible linkers.

Cleavable linkers are those that rely on processes inside a target cell to liberate a drug moiety, such as reduction in the cytoplasm, exposure to acidic conditions in a lysosome or endosome, or cleavage by specific enzymes (e.g. proteases) within the cell. As such, cleavable linkers allow an attached drug moiety to be released in its original form after an immunoconjugate has been internalized and processed inside a target cell. Cleavable linkers include, but are not limited to, those whose bonds can be cleaved by enzymes (e.g., peptide linkers); reducing conditions (e.g., disulfide linkers); or acidic conditions (e.g., hydrazones and carbonates). Non-cleavable linkers utilize catabolic degradation of an immunoconjugate for the release of the drug moiety. A released drug moiety generally retains the linker as well as the amino acid residue of the immunoglobulin to which the linker was conjugated. Non-cleavable linkers include, but are not limited to, PEG linkers, hydrocarbon linkers, and thioether linkers.

Reversible linkers utilize chemical bonds that can readily be broken, or reversed, using suitable reagents. As such, after the formation of a reversible linker, the linker can be broken in a desired position by treatment with a reagent, thereby releasing the immunoglobulin molecule from the linker. Irreversible linkers utilize chemical bonds that cannot readily be broken or reversed after their formation. As such, after the formation of an irreversible linker, an immunoglobulin molecule cannot readily be released.

For site-specific conjugation to the reactive Arg residue in the ADCs of the invention, any chemical moieties known in the art that are reactive with the residues may be employed. For example, non-limiting examples of suitable linkers include, e.g., of phenylglyoxal (PGO), glyoxal (GO), and methylglyoxal (MGO). See, e.g., Takahashi, J. Biochem. 81: 395-402, 1977. As noted above, some ADCs of the invention also contain drug moieties that are conjugated to the reactive lysine residue in 38C2 in addition to the engineered arginine residues. Various other linker moieties can be used for the site-specific Lys conjugation. See, e.g., WO2017/049139. For example, non-limiting examples of reversible linkers for site-specific lysine conjugation include, for example, diketone moieties. Non-limiting examples of irreversible linkers for site-specific lysine conjugation include, for example, β-lactam moieties.

In some embodiments, the linker for attaching the drug moieties can contain an amino acid unit. The amino acid unit allows for cleavage of the linker by a protease, thereby facilitating release of the drug from the immunoconjugate upon exposure to intracellular proteases, such as lysosomal enzymes. See, e.g., Doronina et al. (2003) *Nat. Biotechnol.* 21:778-784. Non-limiting examples of amino acid units include, but are not limited to, a dipeptide, a tripeptide, a tetrapeptide, and a pentapeptide. Non-limiting examples of dipeptides include: valine-citrulline (vc or val-cit), alanine-phenylalanine (af or ala-phe); phenylalanine-lysine (fk or phe-lys); or N-methyl-valine-citrulline (Me-val-cit). Non-limiting examples of tripeptides include: glycine-valine-citrulline (gly-val-cit) and glycine-glycine-glycine (gly-gly-gly). An amino acid unit can comprise amino acid residues that occur naturally, as well as minor amino acids and non-naturally occurring amino acid analogs, such as citrulline. Amino acid units can be designed and optimized in their selectivity for enzymatic cleavage by a particular enzyme, for example, a tumor-associated protease, cathepsin B, C and D, or a plasmin protease.

In some embodiments, the linker can be a branched or dendritic type linker moiety for covalent attachment of more than one drug moiety through a branching, multifunctional linker moiety to an immunoglobulin (Sun et al (2002) Bioorganic & Medicinal Chemistry Letters 12:2213-2215; Sun et al (2003) Bioorganic & Medicinal Chemistry 11:1761-1768). Non-limiting examples of branched, dendritic linkers include 2,6-bis(hydroxymethyl)-p-cresol and 2,4,6-tris(hydroxymethyl)-phenol dendrimer units (WO 2004/01993; Szalai et al (2003) J. Amer. Chem. Soc. 125: 15688-15689; Shamis et al (2004) J. Amer. Chem. Soc. 126:1726-1731; Amir et al (2003) Angew. Chem. Int. Ed. 42:4494-4499). Branched linkers can increase the molar ratio of drug to immunoglobulin, i.e., loading, which is related to the potency of the ADC. Thus, for example, where an immunoglobulin bears only one reactive amino acid residue for conjugation, a multitude of drug moieties can be attached through a branched linker.

The linkers suitable for use in the ADCs of the invention, including stretcher, spacer, and amino acid units, can be synthesized by methods known in the art, such as those described in US Patent Publication No. 2005/0238649 A1.

VI. Payloads or Cargo Moieties

The ADCs of the invention are intended to deliver a payload or cargo moiety (e.g., a drug) to the specific target of interest. The payload broadly includes, but are not limited to, biologically active moieties, such as drug moieties and expression modifying moieties, as well as non-biologically active moieties, such as detectable moieties (e.g., detectable labels). Non-limiting examples of drug moieties include cytotoxic and cytostatic agents that are capable of killing a target cell, or arresting the growth of a target cell. In some embodiments, the employed drug moieties are toxins, chemotherapeutic agents, antibiotics, radioactive isotopes, chelated radioactive isotopes, and nucleolytic enzymes. In some embodiments, the drug moieties for the ADCs of the invention can be polymerized drugs that consist of a polymer drugs. For example, the payload in the ADCs can be polymerized drugs generated via the Fleximer technology developed by Mersana Therapeutics (Cambridge, MA). See, e.g., Yurkovetskiy et al., Cancer Res. 2015, 75:3365-72.

In some embodiments, the payload in the ADCs of the invention is a drug moiety selected from the group consisting of auristatin; dolastatin; cemadotin; amanitin (including but not limited to α-amanitin); monomethyl auristatin F (MMAF); Monomethyl auristatin E (MMAE); maytansinoids (including, but not limited to DM1, DM3 and DM4); pyrrolobenzodiazepines (PBDs, including, but not limited to monomeric and dimeric PBDs); indolinobenzodiazepine (including, but not limited to dimeric indolinobenzodiazepines); enediynes (including but not limited to calicheamicins and tiancimycins); camptothecins (including but not limited to SN-38); doxorubicin (including but not limited to MMDX or bioactivation products thereof, such as, e.g., PNU-159682); a duocarmycin. In some embodiments, the drug moiety in the ADCs of the invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, a proteasome inhibitor, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In some embodiments, the ADCs of the invention can contain a drug moiety that modifies a given biological response. Drug moieties are not to be construed as limited to classical chemical therapeutic agents. For example, a drug moiety can be a protein, peptide, or polypeptide possessing a desired biological activity. Such proteins can include, for example, a toxin such as abrin, ricin A, *pseudomonas* exotoxin, cholera toxin, or diphtheria toxin, a protein such as tumor necrosis factor, α-interferon, (3-interferon, nerve growth factor, platelet derived growth factor, tissue plasminogen activator, a cytokine, an apoptotic agent, an anti-angiogenic agent, or a biological response modifier such as, for example, a lymphokine. In some embodiments, the drug moiety can be a cytotoxin, a drug (e.g., an immunosuppressant) or a radiotoxin. Examples of cytotoxins include but are not limited to, taxanes, DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety, taxon, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Drug moieties can also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). See, e.g., US Patent Publication No. 20090304721, which is incorporated herein by reference in its entirety. Other non-limiting examples of cytotoxins that can be conjugated to the antibodies, antibody fragments (antigen binding fragments) or functional equivalents of the invention include duocarmycins, calicheamicins, maytansines and auristatins, and derivatives thereof.

The cargo moieties in the ADCs of the invention can also be a radioactive isotope or a chelated radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, lutetium-177, bismuth-213 and astatine-211. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In some embodiments, the macrocyclic chelator is 1,4,7,10-tetraazacyclododecane-N,N',N'',N'''-tetraacetic acid (DOTA) which can be attached to an immunoglobulin via a linker molecule.

In some embodiments, the payload of the ADCs of the invention can be a photoabsorber for near infrared (NIR) photoimmunotherapy (PIT). PIT is a new tumor-targeted anticancer platform that can induce a rapid and specific destruction of the tumor. The treatments consist of a drug (a cancer-targeting photoactivatable antibody conjugate) and a device system to apply light at the tumor site. PIT is unique in that it combines molecular targeting of the cancer cells to achieve high tumor specificity, together with a biophysical mechanism of cancer cell destruction that results in broad spectrum anticancer activity regardless of the tumorigenic mechanism of the patients' tumor. See, e.g., Mitsunaga et al., Nat. Med. 17:1685-92, 2011. For example, the DVD compounds of the invention can include a NIR PIT photoabsorber (e.g., IR700) and an antigen-binding variable domain region targeting tumor cells.

In various embodiments, the payload of the ADCs of the invention can be a single drug unit or a plurality of identical drug units, such as 2, 3, 4, 5, 6, 7, 8, 9, or 10 drug units on the same drug moiety. In some embodiments, the drug moiety includes two different drug units on the same drug moiety. For example, in some aspects, a single drug moiety can include both an MMAF drug unit and a PBD monomer drug unit. Furthermore, in certain aspects, a subject immunoconjugate can include a first drug moiety conjugated to a first arm of the immunoconjugate, and a second drug moiety conjugated to the second arm of the immunoconjugate. As such, any of a variety of combinations of drug moieties can be conjugated to a subject DVD-Ig via a linker. As exemplification, the ADCs can contain a site-specific Arg conjugated carboxytetramethylrhodamine (TAMRA) and a site-specific Lys conjugated MMAF on its two arms.

In some embodiments, the cargo moieties in the ADCs of the invention are expression modifying moieties. Expression modifying moieties include, but are not limited to, non-protein-coding RNA ("npcRNA"). In some embodiments, the npcRNA can be, e.g., a microRNA (miRNA), a miRNA precursor, a small interfering RNA (siRNA), a small RNA and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA).

In some embodiments, the cargo moieties in the ADCs of the invention are detectable moieties. Detectable moieties include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives including carboxytetramethylrhodamine (TAMRA), dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

VII. Production of Site-Specific Arg Conjugated ADCs

The site-specific arginine conjugated antibody conjugate drugs (ADCs) of the invention can be produced with any methods known in the art and the specific techniques exemplified herein. For example, expression from host cells, wherein expression vector(s) encoding the DVD heavy and/or DVD light chains is transfected into a host cell by standard techniques. Various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the DVD immunoglobulins of the invention in either prokaryotic or eukaryotic host cells, expression of DVD immunoglobulins in eukaryotic cells is preferable, and most preferable in mammalian host cells, because such eukaryotic cells (and in particular mammalian cells) are more likely than prokaryotic cells to assemble and secrete a properly folded and immunologically active DVD immunoglobulin.

Preferred mammalian host cells for expressing the recombinant immunoglobulins of the invention include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), Human Embryonic Kidney (HEK) cells, NSO myeloma cells, COS cells and SP2 cells. When recombinant expression vectors encoding DVD immunoglobulins are introduced into mammalian host cells, the DVD immunoglobulins are produced by culturing the host cells for a period of time sufficient to allow for expression of the DVD immunoglobulins in the host cells or, more preferably, secretion of the DVD immunoglobulins into the culture medium in which the host cells are grown. DVD immunoglobulins can be recovered from the culture medium using standard protein purification methods.

In a preferred system for recombinant expression of DVD immunoglobulins of the invention, a recombinant expression vector encoding both the DVD heavy chain and the DVD light chain is introduced into dhfr-CHO cells by calcium phosphate-mediated transfection. Within the recombinant expression vector, the DVD heavy and light chain genes are each operatively linked to CMV enhancer/AdMLP promoter regulatory elements to drive high levels of transcription of the genes. A recombinant expression vector also carries a DHFR gene, which allows for selection of CHO cells that have been transfected with the vector using methotrexate selection/amplification. Selected transformant host cells are cultured to allow for expression of the DVD heavy and light chains and intact DVD immunoglobulin is recovered from the culture medium. Standard molecular biology and tissue culture techniques are used to prepare the recombinant expression vector, transfect the host cells, select for transformants, culture the host cells and recover the DVD immunoglobulin from the culture medium. In addition, aspects of the invention include a method of synthesizing a DVD immunoglobulin of the invention by culturing a host cell of the invention in a suitable culture medium until a DVD immunoglobulin of the invention is synthesized. A method can further comprise isolating the DVD immunoglobulin from the culture medium to yield an isolated immunoglobulin.

A feature of the subject DVD immunoglobulins is that they can be produced and purified in ways that are similar to conventional antibodies. Production of DVD immunoglobulins can result in a homogeneous, single major product with desired activity, without any sequence modification of the constant region or chemical modifications of any kind.

VIII. Therapeutic Applications and Pharmaceutical Combinations

The site-specific Arg conjugated ADCs of the invention can be used in a variety of prophylactic, therapeutic and diagnostic applications. The specific application of an ADC of the invention will depend on the payload or drug moiety conjugated to the antibody compound. When a DVD based ADC is used, the specific application is also depending on the target molecule that is recognized by the second variable domain in the DVD. Thus, the antibody compounds and ADCs described herein can be employed in the treatment of various tumors. The compounds of the invention can be readily applied in many specific cancer therapies. Such therapeutic applications include, e.g., delivery of drug moieties to tumors via a known tumor targeting antibody or antigen-binding variable domain as exemplified herein. They also include treatments not directly targeting tumor cells, e.g., antibody-siRNA conjugates for targeting T cells, other immune cells, and tumor-supporting cells. They further include other non-conventional cancer therapies, e.g., the use of near infrared (NIR) photoimmunotherapy (PIT) for treating tumors (as well as non-tumor cells). The compounds of the invention (e.g., DVD based ADCs) can also be used in treating non-oncology indications such as infectious diseases, autoimmune diseases, cardiovascular diseases, metabolic diseases. See, e.g., Beck et al., Nat Rev Drug Discov. 2017, 16:315-337.

As exemplification, some ADCs of the invention including ADCs containing the HER2-targeting DVD compounds exemplified herein, can be used in the treatment of various cancers and other diseases by targeting and killing cells that express a particular tumor antigen. Suitable types of cancers include, without limitation, hematologic cancers, carcinomas, sarcomas, melanoma, and central nervous system cancers. Non-limiting examples of hematologic cancers that can be treated with the ADCs of the invention include leukemia, acute myeloid leukemia, acute lymphoblastic leukemia, chronic myelogenous leukemia, chronic lymphocytic leukemia, lymphoma, Hodgkin's lymphoma, non-Hodgkin's lymphoma, myeloma and myelodysplastic syndrome. Non-limiting examples of carcinomas that can be treated with the ADCs of the invention include skin cancer, head and neck, thyroid, lung, nasopharyngeal, colorectal, liver, urinary bladder, ovarian, cervical, endometrial, prostate, gastric, esophageal, pancreatic, renal, and breast cancer. Non-limiting examples of sarcomas that can be treated with the ADCs of the invention include angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, Kaposi's sarcoma and synovial sarcoma. Non-limiting examples of central nervous system cancers that can be treated with the ADCs of the invention include glioma, meningioma and neuroma. Non-limiting examples of other cancers that can be treated with the ADCs of the invention include melanoma.

In some embodiments, the ADCs of the invention can be used in conjunction with one or more additional therapies to treat a particular cancer. For example, the ADCs of the invention can be used in combination with or as an adjunct to conventional treatment with other medications such as an anti-neoplastic agent, a cytotoxic agent, an anti-angiogenic agent, or an immunosuppressive agent. Non-limiting examples of additional therapeutic agents include cisplatin, carboplatin, oxaliplatin, mechlorethamine, cyclophosphamide, chlorambucil, ifosfamide, doxorubicin, daunorubicin, valrubicin, idarubicin, epirubicin, actinomycin, bleomycin, plicamycin, mitomycin, bevacizumab, imatinib, erlotinib, gefitinib, ibrutinib, idelalisib, lenalidomide, vincristine, vinblastine, vinorelbine, vindesine, paclitaxel, and docetaxel. Any anti-neoplastic agents can be used in such a combination therapy. These include conventional and/or experimental chemotherapeutic agents, radiation treatments, and the like.

For therapeutic uses, the ADCs of the invention can be formulated into pharmaceutical compositions. The pharmaceutical compositions typically contain an effective amount of an immunoconjugate and a pharmaceutically acceptable carrier. The pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it can be necessary to coat the compound with, or co-administer the compound with, a material to prevent its inactivation. For example, a compound can be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

Pharmaceutical compositions of the invention can also contain adjuvants such as preservatives, wetting agents, emulsifying agents and/or dispersing agents. Prevention of the presence of microorganisms can be ensured both by sterilization procedures and by the inclusion of various antibacterial and antifungal agents, for example, paraben, chlorobutanol, phenol, sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption, such as aluminum monostearate and gelatin.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. A selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical fields. The pharmaceutical compositions must be sterile and fluid to the extent that the composition is deliverable by syringe. In addition to water, the carrier preferably is an isotonic buffered saline solution.

Pharmaceutical compositions of the invention can further contain an effective amount of a second therapeutic agent. In some embodiments, the second therapeutic agent is an antibody, an anti-neoplastic agent, a cytotoxic agent, an anti-angiogenic agent, or an immunosuppressive agent. In some embodiments, the second therapeutic agent is selected from the group consisting of: cisplatin, carboplatin, oxaliplatin, mechlorethamine, cyclophosphamide, chlorambucil, ifosfamide, doxorubicin, daunorubicin, valrubicin, idarubicin, epirubicin, actinomycin, bleomycin, plicamycin, mitomycin, bevacizumab, imatinib, erlotinib, gefitinib, ibrutinib, idelalisib, lenalidomide, vincristine, vinblastine, vinorelbine, vindesine, paclitaxel, and docetaxel.

The following examples, sequences and figures are provided to aid the understanding of the present invention, the true scope of which is set forth in the appended claims. It is understood that modifications can be made in the procedures set forth without departing from the spirit of the invention.

EXAMPLES

The following examples are offered to illustrate, but not to limit the present invention.

Example 1 Generation and Crystallization of h38C2_Arg Fab

Figure 2:
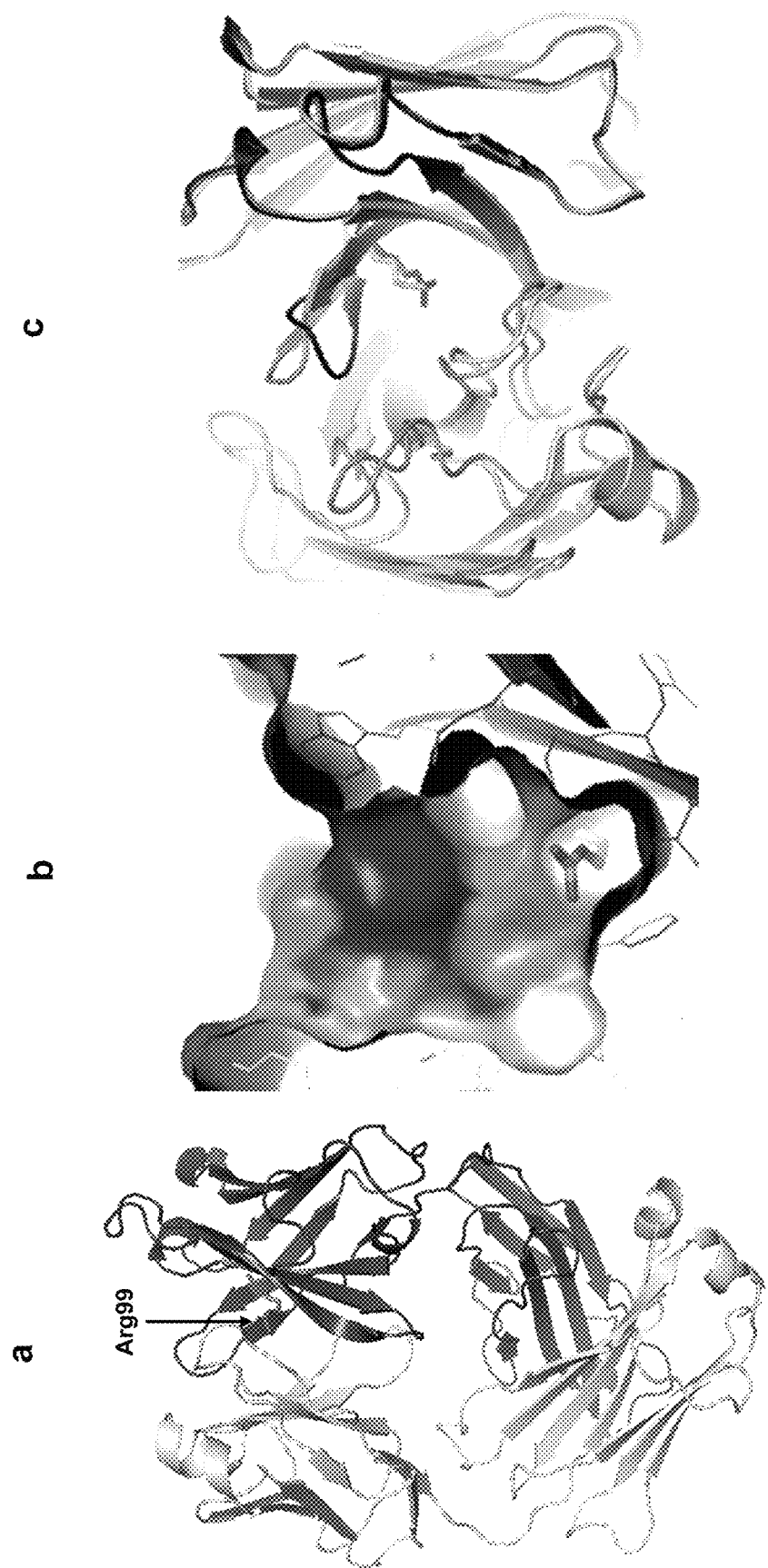
FIG. 2. Crystal structure of h38C2 Arg Fab. (a) The three-dimensional structure of the Lys99Arg mutant of h38C2 in Fab format was determined by X-ray crystallography at 2.4-Å resolution. In this ribbon diagram, the variable domains of light ($V_\kappa$) and heavy chain ($V_H$) are shown in light and dark gray, respectively, and the constant domains ($C_\kappa$ and $C_H1$) in gray. $V_H$'s Arg99 (arrow) is located at the bottom of a deep pocket between $V_\kappa$ and $V_H$. (b) Surface rendering model of the pocket of h38C2_Arg Fab. The side chain of Arg99 with its guanidino group is shown at the bottom. (c) Top view overlay of the ribbon diagrams of h38C2_Arg (PDB:6DZR) and 33F12 Fab (gray; PDB ID 1AXT). The presence of the sulfate ion in the pocket (FIG. 3a) pulls β-strand G' of h38C2 Arg Fab's $V_H$ toward the pocket. This structural change reduces the cavity volume to ~300 Å$^3$ compared to ~450 Å$^3$ for 33F12.
Figure 3:
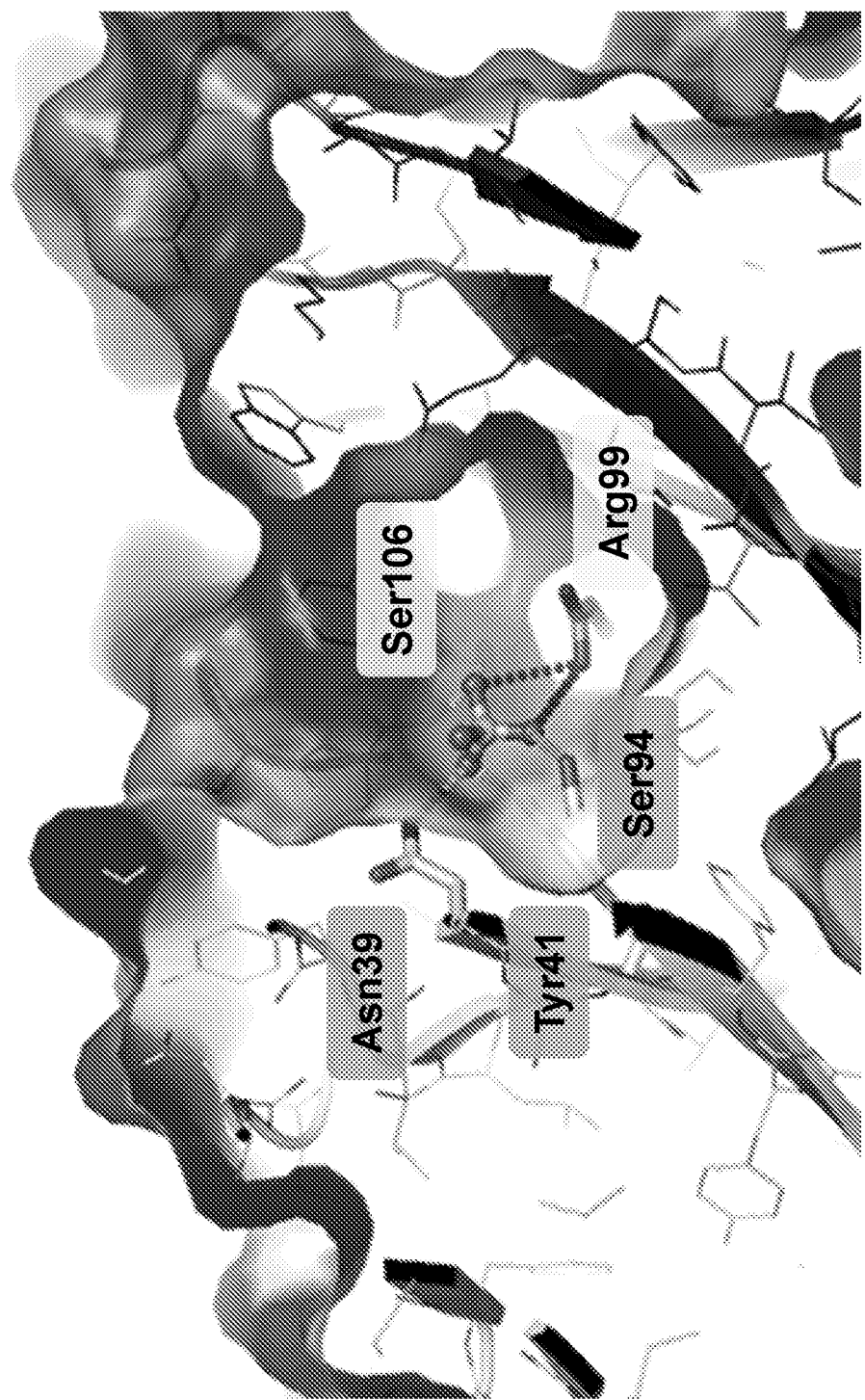
FIG. 3. Crystal structure of h38C2 Arg Fab and pH conjugation rate profile. (a) Crystal structure of h38C2 Arg Fab. Surface rendering model of h38C2_Arg Fab showing the deep pocket between $V_\kappa$ (light gray) and $V_H$ (dark gray) and the guanidinium (protonated guanidino) group of Arg99 at the bottom of the pocket forming a salt bridge (magenta) with a free sulfate ion. Pocket-lining residues of $V_\kappa$ (Asn39, Tyr41, and Ser94) and $V_H$ (Ser106) form hydrogen bonds (light blue) with the sulfate ion. In addition to the sulfate ion, the pocket is filled with eight water molecules (not shown). (b) Left: pH-conjugation rate (apparent $pK_a$) plot for Arg99 on h38C2_Arg shows an inflection point at pH 5.2 ($pK_a$). Right: pH-conjugation rate (apparent $pK_a$) plot of Arg99 on a hexapeptide (Ac-Tyr-Cys(S-acetamide)-Arg99-Thr-Tyr-Phe-OH) indicates that the inflection point is higher than 11.9 ($pK_a$>11.9).

Catalytic antibody 38C2, which was generated by reactive immunization of mice using an aromatic hapten with β-diketone functionality, and its humanized version h38C2 contain a highly reactive buried lysine residue at position 99 (which is position 93 by Kabat numbering) in the variable heavy chain domain ($V_H$) (Karlstrom et al., Proc Natl Acad Sci USA 97, 3878-3883, 2000). Due to its location at the bottom of a deep hydrophobic pocket, protonation of the ε-amino group of Lys99 is disfavored, thereby reducing its $pK_a$ and increasing its nucleophilicity. The unique reactivity of Lys99 is essential for the aldolase activity of mAbs 38C2 and h38C2 and has been utilized for reversible and irreversible covalent conjugation to β-diketone hapten and β-lactam hapten derivatives, respectively, to afford highly homogeneous chemically programmed antibodies and ADCs (FIG. 1a). Hypothesizing that substituting Lys99 with other nucleophilic amino acid residues would afford an orthogonal conjugation chemistry, we cloned, expressed, and purified a Lys99Arg mutant of h38C2 (termed h38C2_Arg) in Fab format and determined its three-dimensional structure by X-ray crystallography at 2.4-Å resolution (FIG. 2a and Table 2). Similar to Lys99 in the parental antibody, Arg99 was positioned at the bottom of a deep pocket filled with one sulfate ion and eight water molecules (FIG. 2b and FIG. 3a). An overlay with the crystal structure of catalytic antibody 33F12, which is closely related to 38C2, confirmed that the three-dimensional structures were highly conserved with disparities confined to the Lys99Arg mutation and a slight tilt of Tyr101 at the rim of the pocket (FIG. 2c).

We next determined the $pK_a$ of Arg99 to test our hypothesis that the unusual reactivity of Arg99 stems from a substantially perturbed $pK_a$ of the conjugate acid. We employed the kinetic method (pH-rate profile) to determine the apparent $pK_a$ of Arg99 (Reijenga et al., *Anal Chem Insights* 8, ACLS12304, 2013). h38C2_Arg was treated with MMAF-TPG at different pH levels and the reaction rates were determined by RP-HPLC. The rates were then plotted as a function of reaction pH. The pH-conjugation rate profile is shown in FIG. 3b-left and shows an inflection point at around 5.2, indicating the apparent $pK_a$ of Arg99. A commonly referred $pK_a$ value of a conjugate acid of Arg is around 12 to 12.5, even though a value as high as 13.8 has also been reported (Fitch et al., Protein Sci 24, 752-761, 2015). Despite the high $pK_a$ of the guanidinium side chain, a perturbed $pK_a$ as low as 8.0 or 9.1 has been reported (Niemeyer et al., Proc Natl Acad Sci 104, 666-671, 2007 and Wells et al., Biochemistry 33, 5777-5782, 1994). However, the exceptionally low $pK_a$ of 5.2, ~7 orders of magnitude lower than the normally referenced value, has, to our knowledge, never been reported. To confirm the observed $pK_a$ of 5.2 for Arg99 is due to the h38C2 hydrophobic pocket, we synthesized and assessed the $pK_a$ of a hexapeptide, Ac-Tyr-Cys(S-acetamide)-Arg99-Thr-Tyr-Phe-OH, mimicking the amino acids surrounding the Arg99 (FIG. 3b-right). The hexapeptide was treated with phenylglyoxal to determine the apparent $pK_a$ of an Arg residue outside the h38C2 hydrophobic pocket. Due to the instability of the peptide at pH>12.5, we were not able to obtain a definite $pK_a$ value for the arginine residue on the hexapeptide In addition, the reaction rate between the peptide and phenylglyoxal becomes very fast at pH≥11.6, thus preventing us from determining the $pK_a$ of the Arg residue within an HPLC timescale. However, monitoring of the reaction rate at pH≥11.6 gives the pH-conjugation rate plot shown in FIG. 3b-right which suggests the apparent $pK_a$ of the peptide-based Arg residue is >11.9. Even thought the $pK_a$ obtained is a rough estimate, these data confirms that the $pK_a$ of Arg99 outside the h38C2 pocket is several orders of magnitude higher than 5.2. The $pK_a$ determinations both on-protein and off-protein validate our hypothesis that the microenvironment of the hydrophobic pocket in h38C2 perturbs the $pK_a$ of Arg99. The extremely low $pK_a$ of 5.2 for Arg99 of h38C2 makes this residue unusually nucleophilic towards a electrophilic phenylglyoxal. Under slightly acidic conditions (pH of 6.6), Arg99 can be expected to have approximately 25 times more unprotonated guanidinyl group than surface arginines with average $pK_a$ values around 12.

Example 2 Orthogonal Conjugation Chemistry of h38C2_Arg

Figure 4:
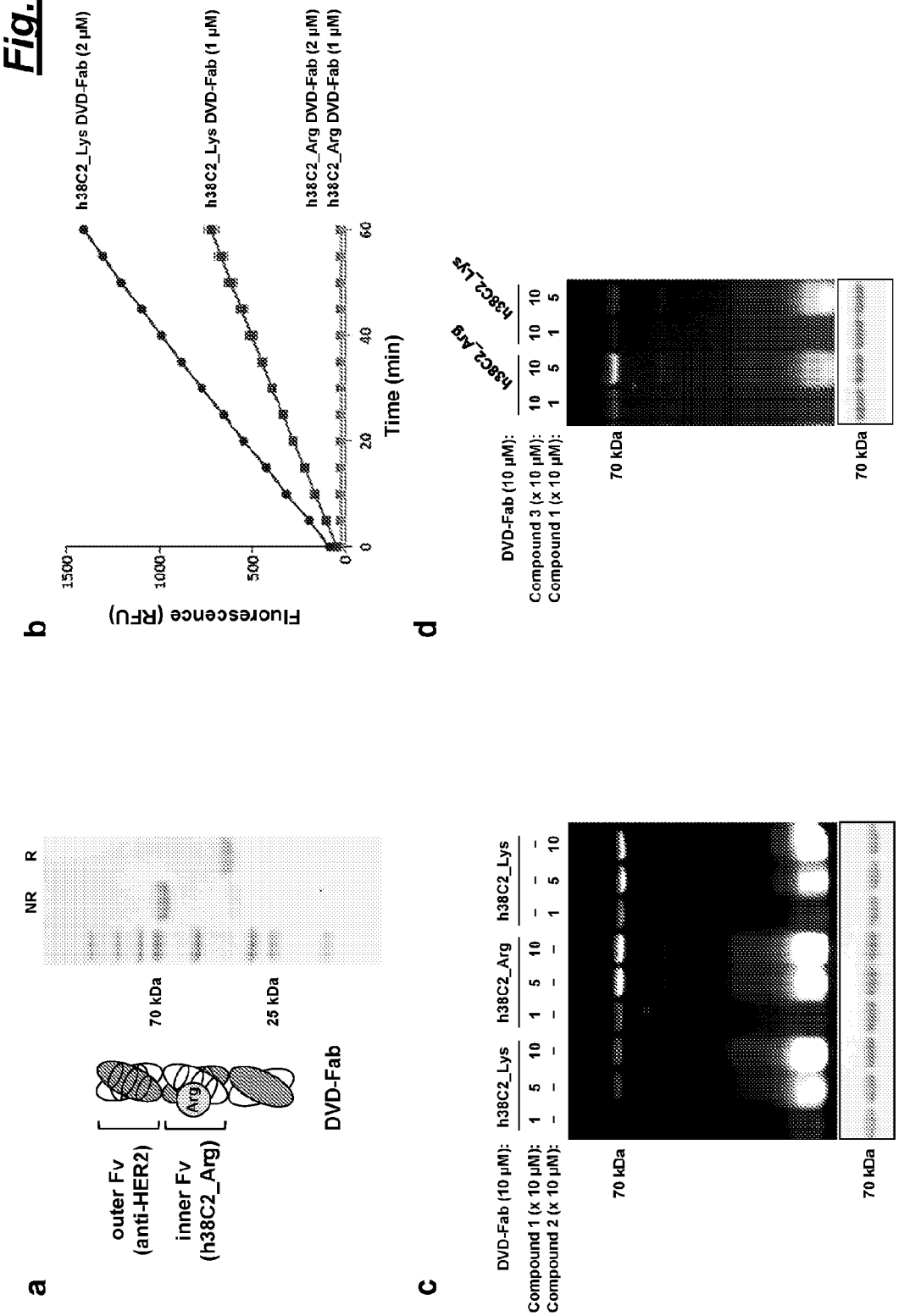
FIG. 4. Generation and characterization of an h38C2 Arg-based DVD-Fab. (a) The DVD-Fab is composed of variable domains of trastuzumab (outer Fv) and h38C2 mutant Lys99Arg (inner Fv with light gray circle) and constant domains. Inner and outer variable domains of both light chain (white) and heavy chain fragment (gray) are connected by a short spacer (ASTKGP) (SEQ ID NO:3). Following purification from the supernatant of transiently transfected Expi293F cells by Protein A affinity chromatography, the DVD-Fab revealed the expected ~70-kDa band by nonreducing (NR) and the expected ~35-kDa bands by reducing (R) SDS-PAGE and Coomassie staining. (b) The catalytic activity of parental (h38C2_Lys) and mutated (h38C2_Arg) DVD-Fab at 1 µM and 2 µM was measured using the retro-aldol conversion of methadol to a detectable fluorescent aldehyde (RFU, relative fluorescent units) and acetone. Mean (±) SD values of triplicates were plotted. (c) DVD-Fabs with h38C2_Arg or h38C2 Lys were incubated with 1, 5, and 10 equivalents of a phenylglyoxal derivative of TAMRA (compound 1.
Figure 5:
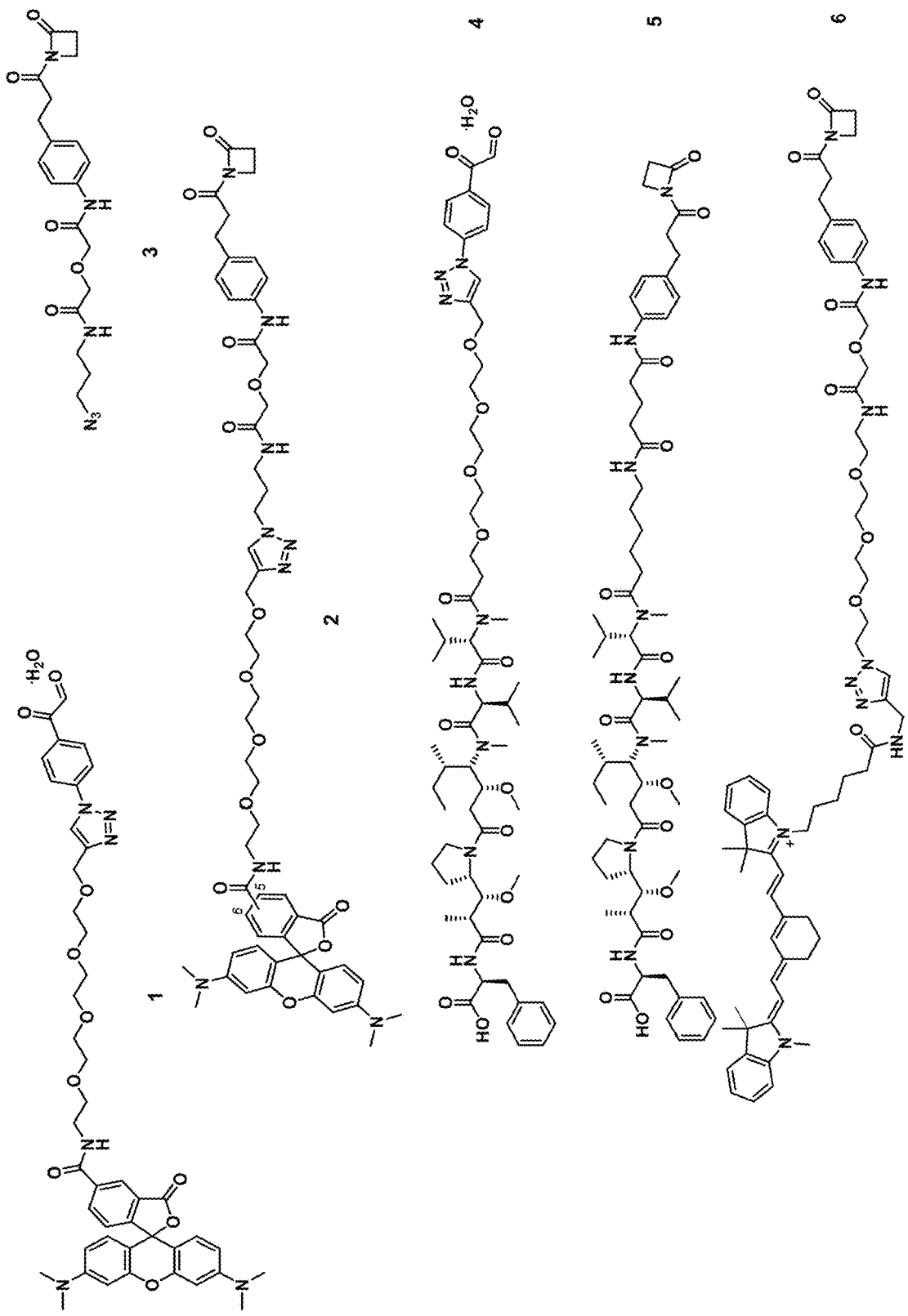
FIG. 5) or a β-lactam-hapten derivative of TAMRA (compound 2.

The preservation of the deep pocket suggested that similar to buried Lys99, buried Arg99 would have unique reactivity that could be utilized for site-specific conjugation. To test this, we first cloned, expressed, and purified a DVD-Fab with the outer Fv derived from humanized anti-human HER2 mAb trastuzumab (Herceptin®) and the inner Fv derived from h38C2_Arg (FIG. 4a). A corresponding DVD-Fab with the inner Fv derived from parental h38C2, i.e. the Fab fragment of our previously reported DVD-IgG1 (Nanna et al., Nat Commun, 8:1112, 2017), was generated for comparison. Whereas the two DVD-Fabs were indistinguishable with respect to yield and purity, they revealed the expected dramatic difference in catalytic activity. The DVD-Fab based on h38C2_Arg had entirely lost the retro-aldol activity that typifies aldolase antibodies 33F12, 38C2, and h38C2 and is mediated by Lys99 (FIG. 4b). To probe Arg99 for site-specific conjugation, we synthesized a phenylglyoxal derivative of tetramethylrhodamine (TAMRA) (compound 1; FIG. 5). Phenylglyoxal is known to react with the guanidino group of Arg residues under mild conditions, resulting in the formation of a stable hydroxyimidazole ring (FIG. 1b). Recently, this reaction has been utilized for click chemistry bioconjugations using commercially available 4-azido-phenylglyoxal. Covalent conjugation of compound 1 to h38C2_Arg DVD-Fab following incubation for 3 h at 37° C. in 50 mM HEPES, 50 mM NaHCO$_3$ (pH 6.0) at different molar ratios was analyzed by SDS-PAGE followed by blue light visualization (FIG. 4c). At 5- and 10-fold molar excess of compound 1, a strong fluorescent band at 70 kDa was detected whereas an equimolar amount only resulted in weak staining. Although parental h38C2_Lys DVD-Fab was only weakly stained under the same conditions, suggesting preferential covalent conjugation of compound 1 to Arg99, it revealed a strong fluorescent band at 70 kDa following incubation with 5- and 10-fold molar excess of a β-lactam hapten derivative of TAMRA (compound 2; FIG. 5). Furthermore, pre-incubation of h38C2_Arg DVD-Fab with a non-fluorescent β-lactam hapten (compound 3; FIG. 5) at 10-fold molar excess did not block covalent conjugation of compound 1, demonstrating orthogonal conjugation chemistry of Arg99 and Lys99 (FIG. 4d).

TABLE 2

Data collection and refinement statistics for crystallization of h38C2_Arg Fab

| Data | |
| --- | --- |
| Space group | P6$_5$ |
| Cell dimensions a, b, c (Å) | 91.69, 91.69, 109.01 |
| Cell dimensions α, β, γ (°) | 90, 90, 120 |
| Resolution (Å)[1] | 36.34-2.4 (2.49-2.4) |
| Unique reflections[1] | 20412 (2148) |
| Mean I/σI[1] | 16.4 (5.6) |
| Completeness (%)[1] | 100.0 (100.0) |
| Wilson B-factor | 37.07 |
| R$_{merge}$[1] | 9.3 (46.5) |
| R$_{meas}$[1] | 9.8 (49.1) |
| R$_{pim}$[1] | 3.1 (15.9) |
| Refinement | |
| Resolution (Å)[1] | 35.09-2.4 (2.53-2.4) |
| Reflections in refinement[1] | 20368 (2759) |
| Reflections in R$_{free}$[1] | 994 (150) |
| R$_{free}$[1,2] | 22.77 (33.42) |
| R$_{work}$[1] | 18.16 (26.55) |
| R.m.s. bond length (Å) | 0.012 |
| R.m.s. bond angle (°) | 1.48 |
| B-factor, average (Å$^2$) | 57.75 |
| Number of atoms | |
| Protein | 3356 |
| Water | 153 |
| Model quality | |
| Ramachandran favored (%) | 95.16 |
| Ramachandran allowed (%) | 4.84 |
| Ramachandran outliers (%) | 0 |
| Rotamer outliers (%) | 1.84 |
| Clashscore | 5.13 |

[1]Values in parentheses refer to statistics for the highest resolution shell.
[2]R$_{free}$ is calculated with removal of 5% of the data as the test set before the refinement.

Figure 6:
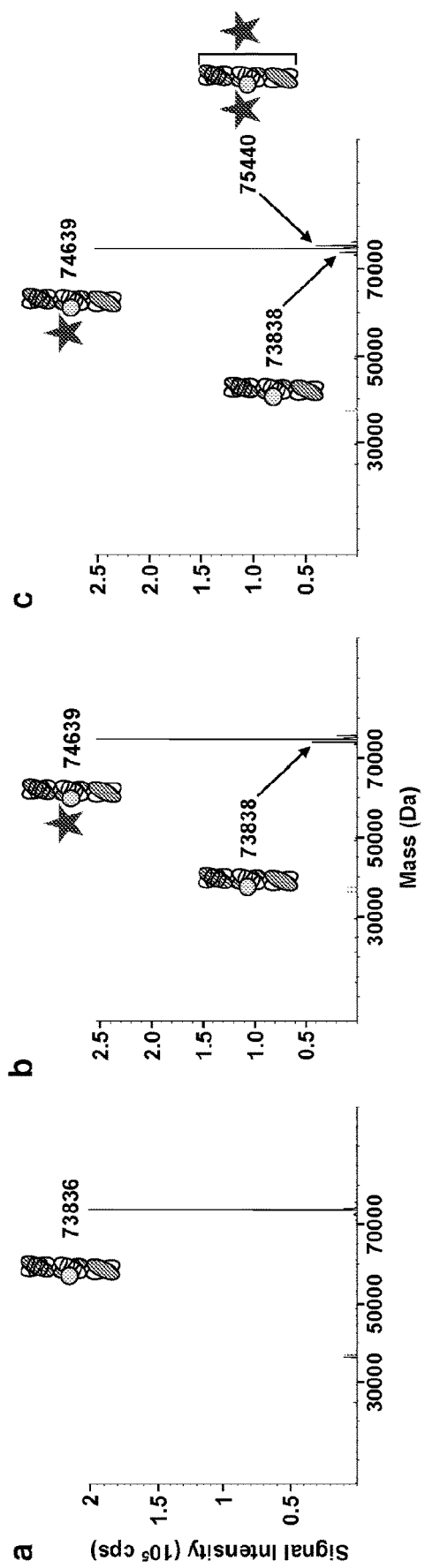
FIG. 6. Mass spectrometry of h38C2_Arg-based DVD-Fab before and after conjugation. (a) Analysis of DVD-Fab with h38C2_Arg by ESI-TOF. The expected mass for the unconjugated DVD-Fab is 73820 Da. For (b) and (c), 5 and 10 equivalents, respectively, of phenylglyoxal-TAMRA (compound 1; ★) were conjugated to the DVD-Fab. The expected mass for the DVD-Fab with one and two conjugated compounds is 74623 Da and 75426 Da, respectively.

Next, we analyzed h38C2_Arg DVD-Fab by mass spectrometry (MS). The unconjugated antibody revealed an observed molecular weight (MW) of 73,836 Da compared to an expected MW of 73,820 Da (FIG. 6). Following incubation with a 5-fold molar excess of compound 1, the observed MW increased by 803 Da, which corresponds to the expected MW increase from the formation of a stable hydroxyimidazole ring at Arg99. The ratio of conjugated to unconjugated antibody was ~8.5:1.5. The signal of the unconjugated antibody decreased when the molar excess of compound 1 was increased to 10-fold. However, a new signal corresponding to an antibody conjugate with two modified Arg residues appeared at a ~8.3:1.7 ratio of single to double conjugated antibody.

Figure 16:
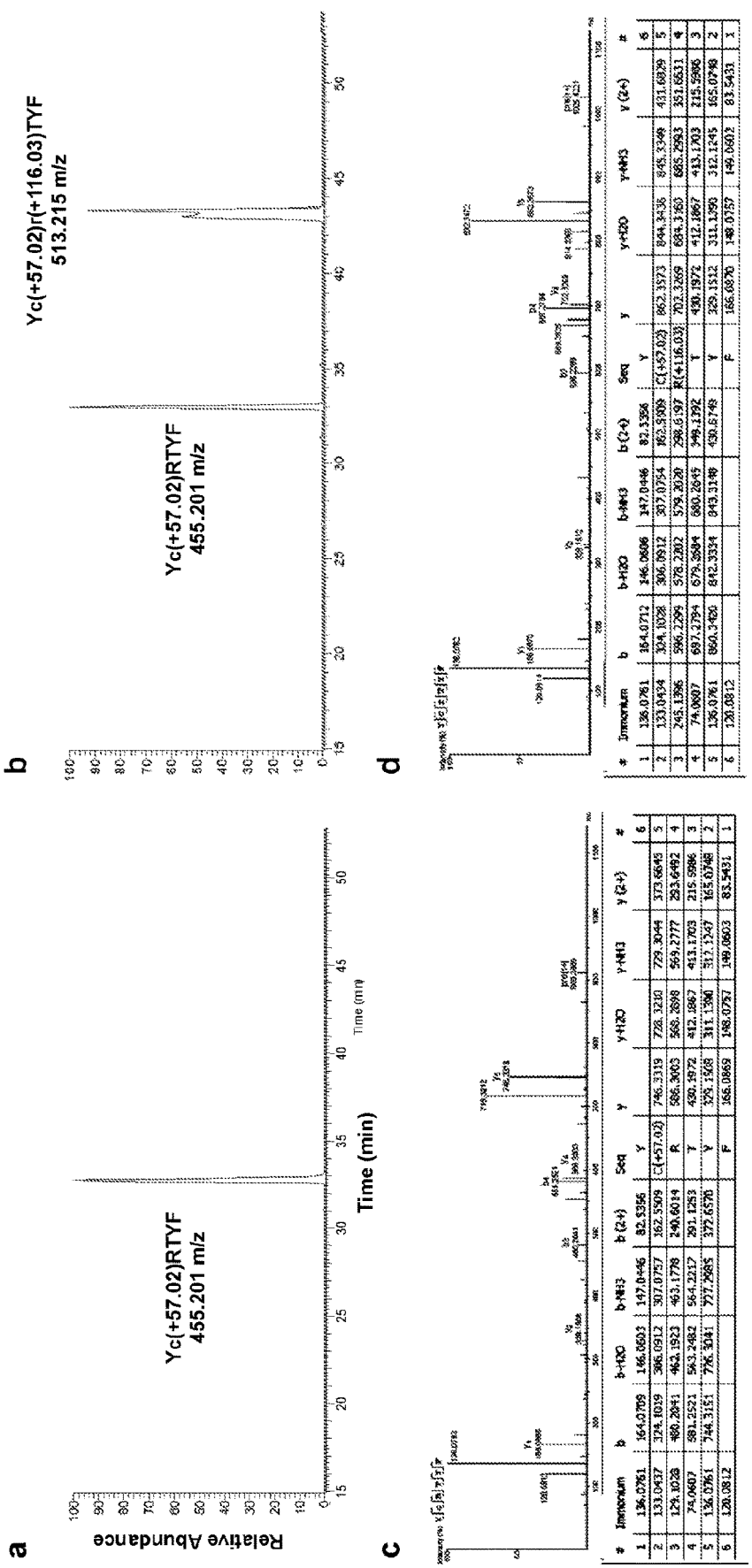
FIG. 16. Mass spectrometry analysis of pepsin-digested h38C2_Arg Fab before and after conjugation to phenylglyoxal. To map the conjugation site, untreated (a, c) and phenylglyoxal-treated (b, d) h38C2_Arg Fab was digested with pepsin and analyzed by LC-MS/MS. One major phenylglyoxal-modified peptide (YCRTYFT) was detected in the phenylglyoxal-treated sample (b). The detected MS/MS spectra along with the predicted b and γ ions are presented for both the unlabeled peptide (c) and the phenylglyoxal-modified peptide (d). The +116-Da modification on the Arg residue, r(+116.03), suggests the formation of a hydroxy-imidazole ring as shown in Supplementary FIG. 1b. The +57-Da modification on the Cys residue, c(+57.02), is a carbamidomethyl group due to the use of iodoacetamide to block disulfide bond formation in the denatured and reduced protein prior to pepsin digestion.

To confirm Arg99 as the conjugation site, untreated and phenylglyoxal-treated h38C2_Arg Fab was digested with pepsin and analyzed by LC-MS/MS. We achieved >90% amino acid sequence coverage of both light and heavy chain sequences. A hexapeptide, Tyr-Cys-Arg-Thr-Tyr-Phe, with a 116-Da modification on the Arg was detected for conjugated but not unconjugated h38C2_Arg Fab (FIG. 16). This hexapeptide matched the amino acid sequence surrounding Arg99 and was the only detectable modified peptide with a higher relative abundance than the corresponding unmodified peptide, thus validating site-specific Arg99 modification. The 116-Da mass-to-charge ratio (m/z) shift on the Arg residue is in agreement with the formation of a hydroxy-imidazole ring between the guanidino group of Arg and phenylglyoxal (FIG. 1b). Although additional modified heavy and light chain peptides were detectable in this experiment, they had a much lower relative abundance than the corresponding unmodified peptides.

Figure 7:
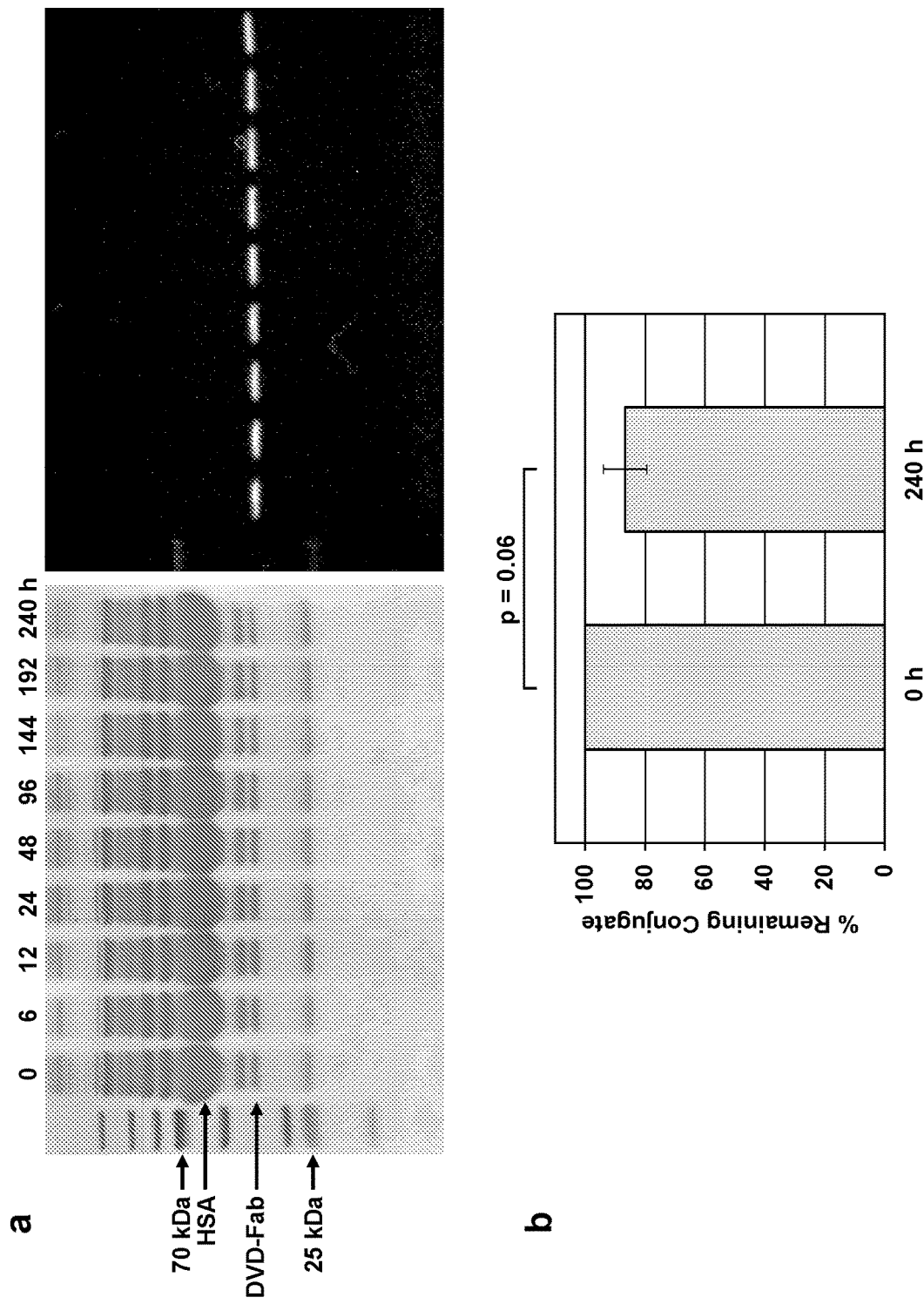
FIG. 7. Human plasma stability of h38C2 Arg-based DVD-Fab conjugate. (a) The h38C2_Arg-based DVD-Fab conjugated to phenylglyoxal-TAMRA (compound 1) was incubated with human plasma at 37° C. for the indicated time and analyzed by SDS-PAGE followed by Coomassie staining (left) and fluorescent imaging (right). (b) Band intensities from fluorescent imaging at time points "0 h" and "240 h" were quantified by NIH ImageJ software and mean±SD values of three independent experiments were plotted by defining the band intensity at time point "0 h" as 100% for each independent experiment. A t-test was used to calculate p.

To assess the stability of the Arg:phenylglyoxal adduct, h38C2_Arg DVD-Fab was conjugated to compound 1 and incubated with human plasma for up to 10 days at 37° C. Analysis after 0, 6, 12, 24, 48, 96, 144, 192, and 240 h revealed high stability of the conjugate with ~15% accumulated decay after 10 days (FIG. 7).

Example 3 Generation and Characterization of ADCs Based on h38C2_Arg

Figure 8:
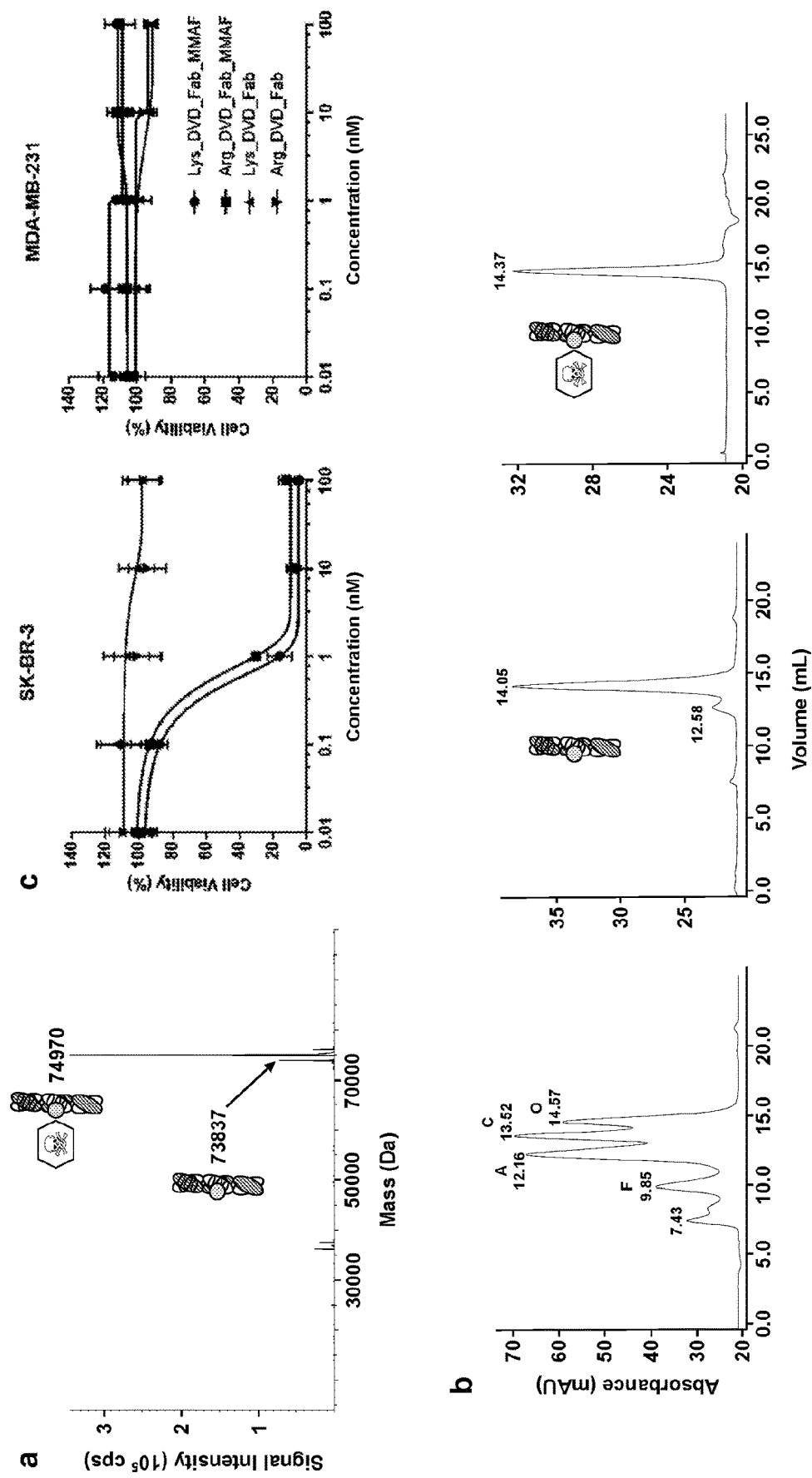
FIG. 8. Characterization of h38C2 Arg-based anti-HER2 DVD-Fab ADC. (a) Analysis of h38C2_Arg-based DVD-Fab conjugated to phenylglyoxal-MMAF (compound 4) by ESI-TOF. The expected masses for the unconjugated and conjugated DVD-Fab are 73820 and 74950 Da, respectively. (b) SEC profiles of standard (left; F: 440 kDa; A: 158 kDa; C: 75 kDa; O: 44 kDa), h38C2_Arg-based DVD-Fab (center), and h38C2 Arg-based DVD-Fab conjugated to phenylglyoxal-MMAF (compound 4) (right). (c) Cytotoxicity of h38C2_Lys-based DVD-Fab conjugated to β-lactam-hapten-MMAF (compound 5) (●), h38C2_Arg-based DVD-Fab conjugated to phenylglyoxal-MMAF (compound 4) (■), and the corresponding unconjugated DVD-Fabs (▲ and ▼, respectively) following incubation with HER2+SK-BR-3 and HER2-MDA-MB-231 cells for 72 h at 37° C.

With conjugation efficiency, selectivity, and stability established, we next investigated the suitability of Arg:phenylglyoxal adducts for the assembly of homogeneous ADCs. For this, we synthesized a phenylglyoxal derivative of MMAF (compound 4; FIG. 5) analogous to the β-lactam hapten derivative of MMAF (compound 5; FIG. 5) we used for assembling homogeneous ADCs that were based on parental h38C2_Lys. Employing the same conditions as for compound 1, the h38C2_Arg DVD-Fab was reacted with compound 4 and the conjugate was confirmed by MS, revealing an observed mass of 74,970 Da and 73,837 Da for the conjugated and unconjugated antibody, respectively, at ~8.5:1.5 ratio and close to the expected mass for a DAR of 1 (FIG. 8a). Size exclusion chromatography (SEC) further showed that the MMAF-conjugated h38C2_Lys99Arg DVD-Fab was free of aggregates (FIG. 8b).

Figure 9:
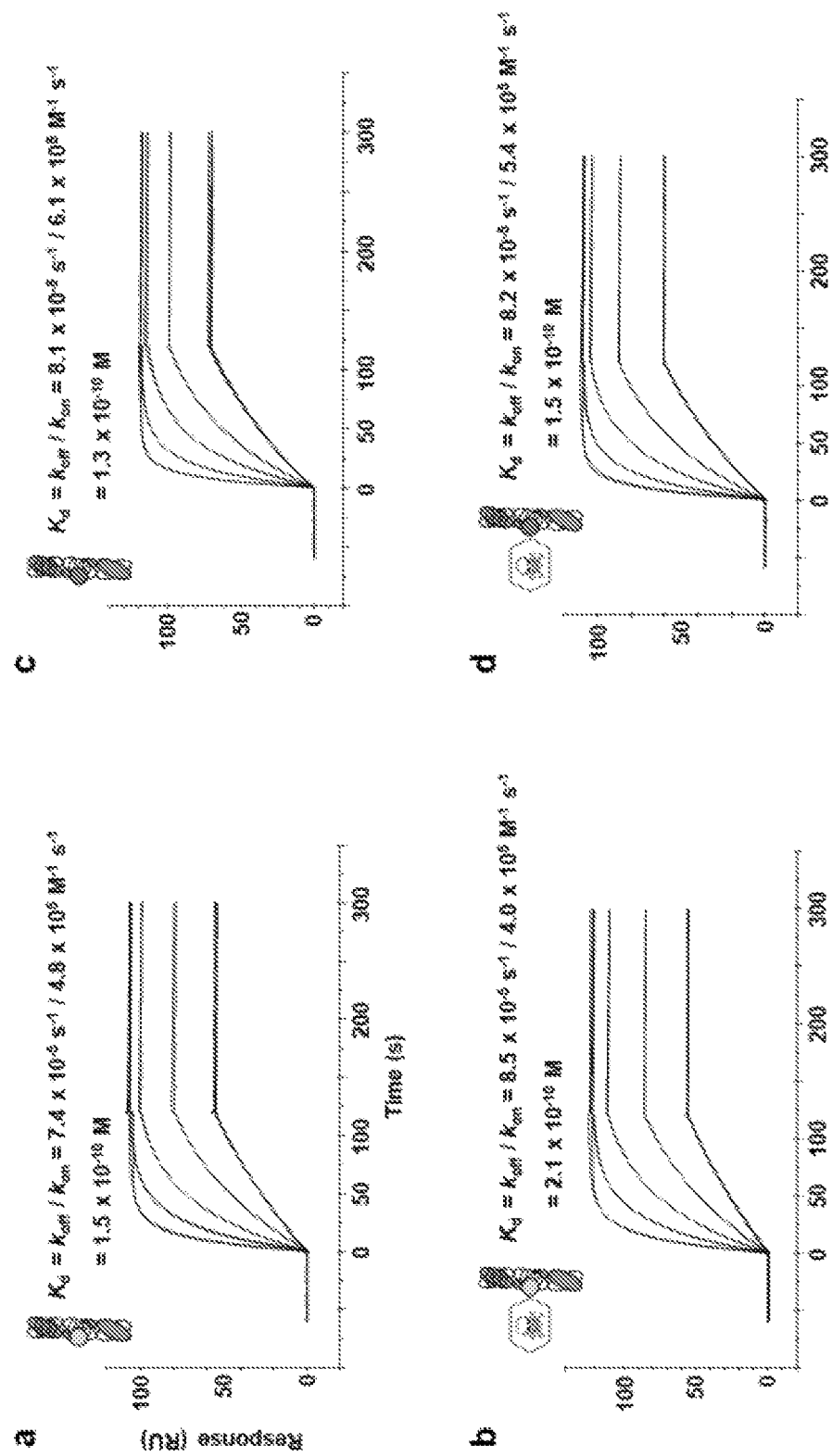
FIG. 9. Comparison of h38C2_Arg- and h38C2_Lys-based anti-HER2 DVD-Fab ADCs by SPR. Biacore X100 sensorgrams obtained for the binding of the indicated unconjugated (a, c) and conjugated (b, d) DVD-Fabs to HER2-Fc captured by an anti-human Fcγ mAb immobilized on a CM5 chip after instantaneous background depletion. The reactive Arg and Lys residue of h38C2 Arg (a, b) and h38C2_Lys DVD-Fabs (c, d) is drawn as light and dark gray circle, respectively. DVD-Fabs were injected at five different concentrations (12.5, 25, 50, 100, and 200 nM).

The ADC in DVD-Fab format revealed cytotoxicity toward HER2-positive human SK-BR-3 breast cancer cells at subnanomolar concentrations while being inactive toward HER2-negative human MDA-MB-231 breast cancer cells at 100 nM, the highest concentration tested (FIG. 8c). Importantly, the Arg99-based ADC ($IC_{50}$=0.85 nM) revealed similar potency and selectivity when compared to the Lys99-based ADC ($IC_{50}$=0.64 nM) assembled from parental h38C2 Lys DVD-Fab and compound 5. The ability of the Arg99-based ADC to eradicate target cells as efficiently as the Lys99-based ADC suggested that binding, internalization, endosomal trafficking, lysosomal degradation, and drug release proceed with similar efficiency or at least give the same net result. Comparing both unconjugated and MMAF-conjugated h38C2_Arg and h38C2 Lys DVD-Fab for binding to HER2 by surface plasmon resonance, revealed highly conserved kinetic and thermodynamic parameters (FIG. 9), confirming that neither Arg99Lys mutation nor drug conjugation to the inner Fv interferes with targeting mediated by the outer Fv.

Figure 10:
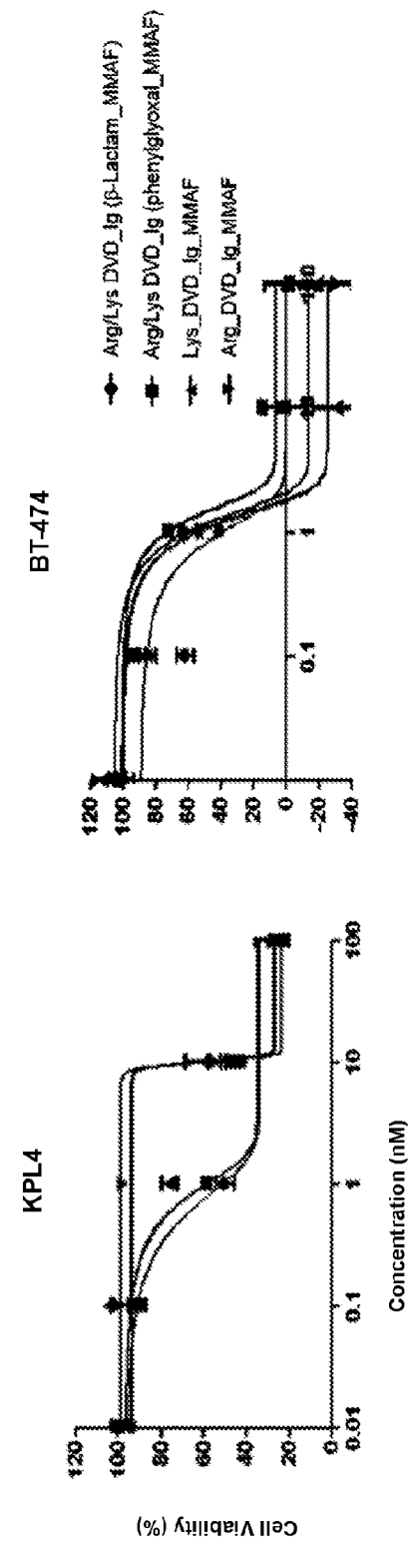
FIG. 10. Generation and characterization of homodimeric and heterodimeric DVD-IgG1s. (a) Analogous to the DVD-Fab, the homodimeric DVD-IgG1 (left) is composed of variable domains of trastuzumab (outer Fv) and parental h38C2 or h38C2 mutant Lys99Arg (inner Fv with light gray circle) and constant domains. Inner and outer variable domains of both light chain (white) and heavy chain fragment (gray) are connected by a short spacer (ASTKGP). The heterodimeric DVD-IgG1 (right) combines a parental h38C2 inner Fv in one arm with h38C2 mutant Lys99Arg in the other arm and utilizes knobs-into-holes mutations (▶) for heavy chain heterodimerization. Following purification from the supernatant of transiently transfected Expi293F cells by Protein A affinity chromatography, the h38C2_Arg-based DVD-IgG1 ("Arg/Arg") was indistinguishable from the previously described h38C2_Lys-based DVD-IgG1 ("Lys/Lys"), revealing the expected ~200-kDa band by nonreducing (NR) and the expected ~65-kDa and ~35-kDa bands by reducing (R) SDS-PAGE and Coomassie staining. The heterodimeric DVD-IgG1 ("Arg/Lys") revealed the same bands. (b) The catalytic activity of homodimeric Lys/Lys and heterodimeric Arg/Lys DVD-IgG1 at 1 µM was measured using the retro-aldol conversion of methadol to a detectable fluorescent aldehyde (RFU, relative fluorescent units) and acetone. Mean (±) SD values of triplicates were plotted. (c-d) Cytotoxicity of the two different homodimeric Lys/Lys and Arg/Arg and the heterodimeric Arg/Lys DVD-IgG1 after conjugation to β-lactam-hapten-MMAF (compound 5) or phenylglyoxal-MMAF (compound 4) following incubation with HER2+SK-BR-3, HER2+KPL4, HER2+BT-474, and HER2-MDA-MB-231 cells for 72 h at 37° C.
Figure 11:
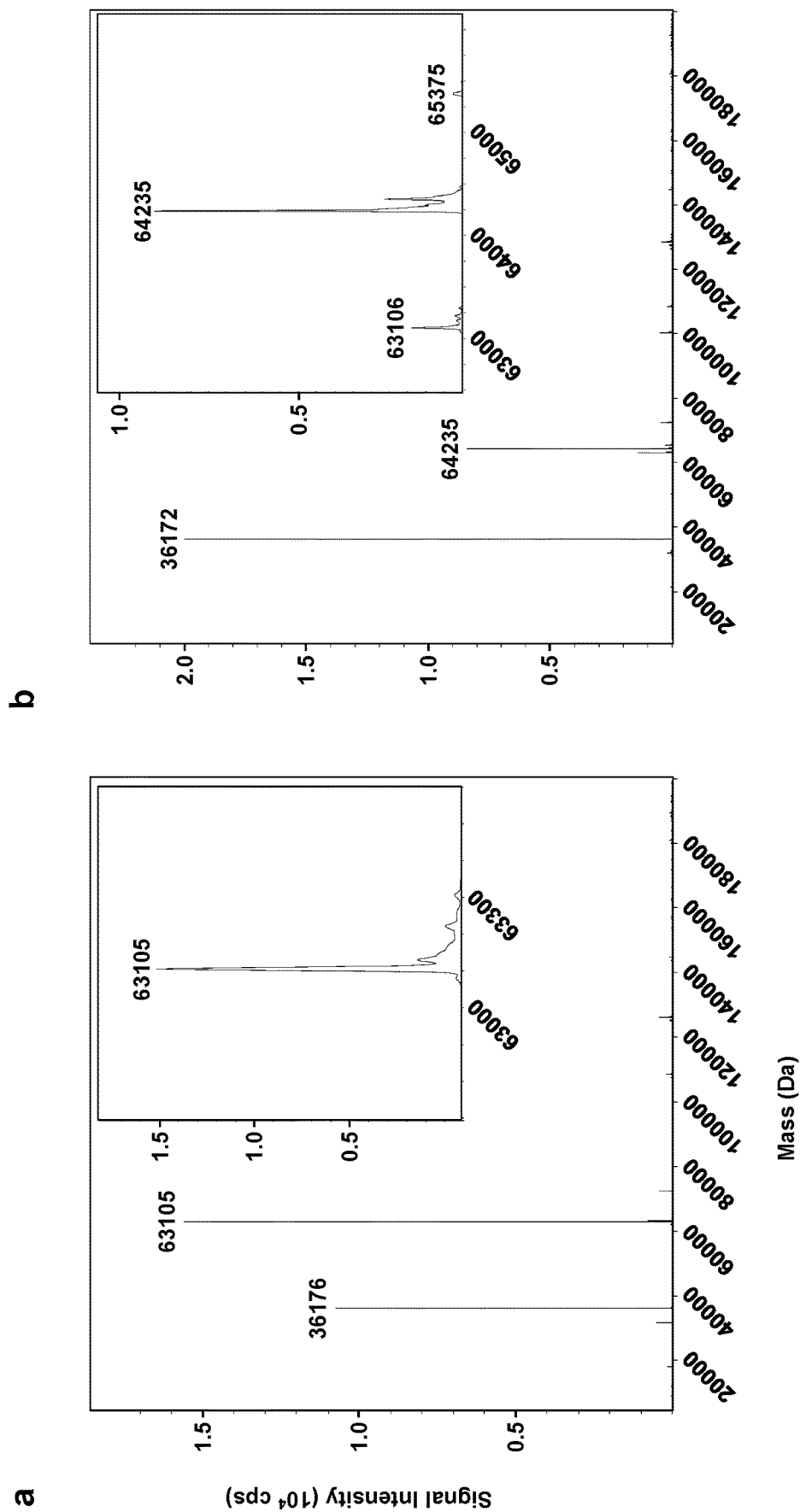
FIG. 11. Mass spectrometry of h38C2_Arg-based DVD-IgG1 before and after conjugation. (a) Analysis of the reduced and deglycosylated DVD-IgG1 with h38C2_Arg by ESI-TOF. The expected masses for light and heavy chains are 36161 Da and 63151, respectively. For (b), 5 equivalents of phenylglyoxal-MMAF (compound 4) were conjugated to the DVD-IgG1. The expected mass for the heavy chain with one conjugated compound is 64282 Da.

The potency of the MMAF-conjugated h38C2_Arg99 DVD-Fab prompted us to generate the corresponding ADC in DVD-IgG1 format (FIG. 10a). Analysis of the ADC by MS revealed two major peaks, one corresponding to the unconjugated light chain and the other corresponding to the heavy chain with a single MMAF payload (FIG. 11). Minor peaks corresponding to the unconjugated heavy chain (15% of the major peak of the heavy chain) and to the heavy chain with two MMAF payloads (0.5%) were also detected, suggesting an overall DAR of ~1.7. As expected, the Arg99-based ADC in DVD-IgG1 format revealed essentially the same potency and selectivity as the Lys99-based ADC in DVD-IgG1 format (FIG. 10c).

Example 4 Generation and Characterization of Heterodimeric DVD-IgG1 that Combine h38C2 Lys and h38C2_Arg We next set out to utilize the orthogonality of Arg:phenylglyoxal and Lys:β-lactam conjugation by combining h38C2_Arg and h38C2_Lys in one DVD-IgG1. Notably, this assembly involves two different heavy chains and two identical light chains, enabling the utilization of knobs-into-holes mutations for heavy chain heterodimerization (FIG. 10a) (See, e.g., Merchant et al., Nat Biotechnol 16, 677-681, 1998). The heterodimeric DVD-IgG1 was expressed and purified in comparable quality and quantity as the homodimeric Arg99-based DVD-IgG1 (FIG. 10a) and revealed the expected ~50% reduction in catalytic activity compared to the Lys99-based DVD-IgG1 (FIG. 10b). Conjugation of either phenylglyoxal or β-lactam hapten derivative of MMAF (compounds 4 and 5, respectively) to the heterodimeric DVD-IgG1 yielded DAR~1 ADCs with high potency and selectivity albeit slightly higher $IC_{50}$ values than the DAR~2 ADCs based on the corresponding homodimeric DVD-IgG1 (0.53 nM vs. 0.39 nM and 0.60 nM vs. 0.37 nM, respectively, with SK-BR-3 cells) (FIG. 10c).

Figure 12:
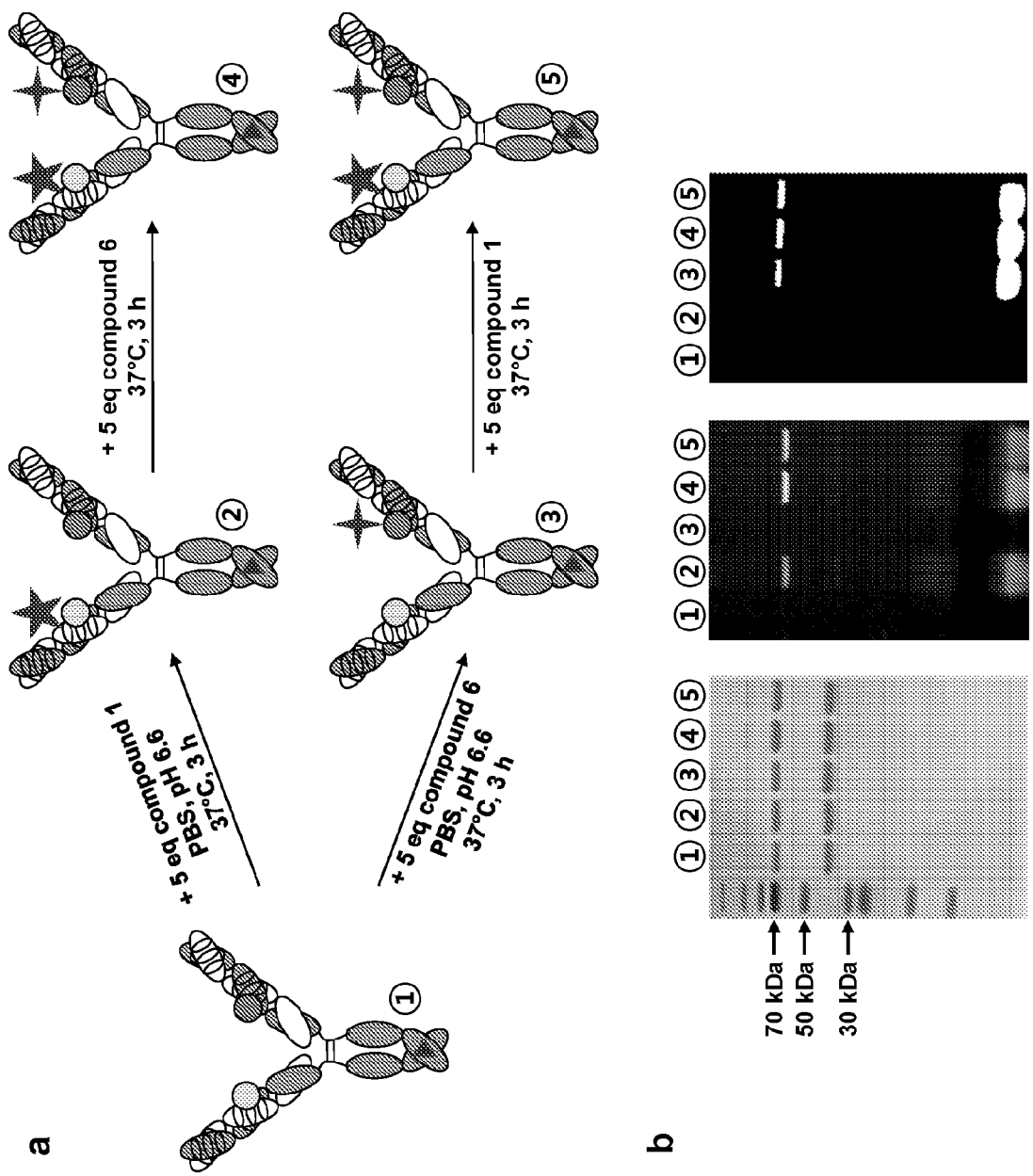
FIG. 12. One-pot assembly of heterodimeric DVD-IgG1 with two different payloads. (a) Scheme of orthogonal labeling of the heterodimeric DVD-IgG1 (dark gray circle, Arg; light gray circle, Lys; triangle, knobs-into-holes mutations) with phenylglyoxal-TAMRA (compound 1, ★) and β-lactam-hapten-Cy7 (compound 6, ✚). Sequential conjugation of the red and infrared fluorescent dyes at the indicated conditions was conducted without intermittent purification or buffer exchange steps. (b) Unconjugated heterodimeric DVD-IgG1 ① and conjugates ②, ③, ④ and ⑤ were analyzed by reducing SDS-PAGE followed by red (middle) and infrared (right) fluorescent imaging and Coomassie staining (left).
Figure 13:
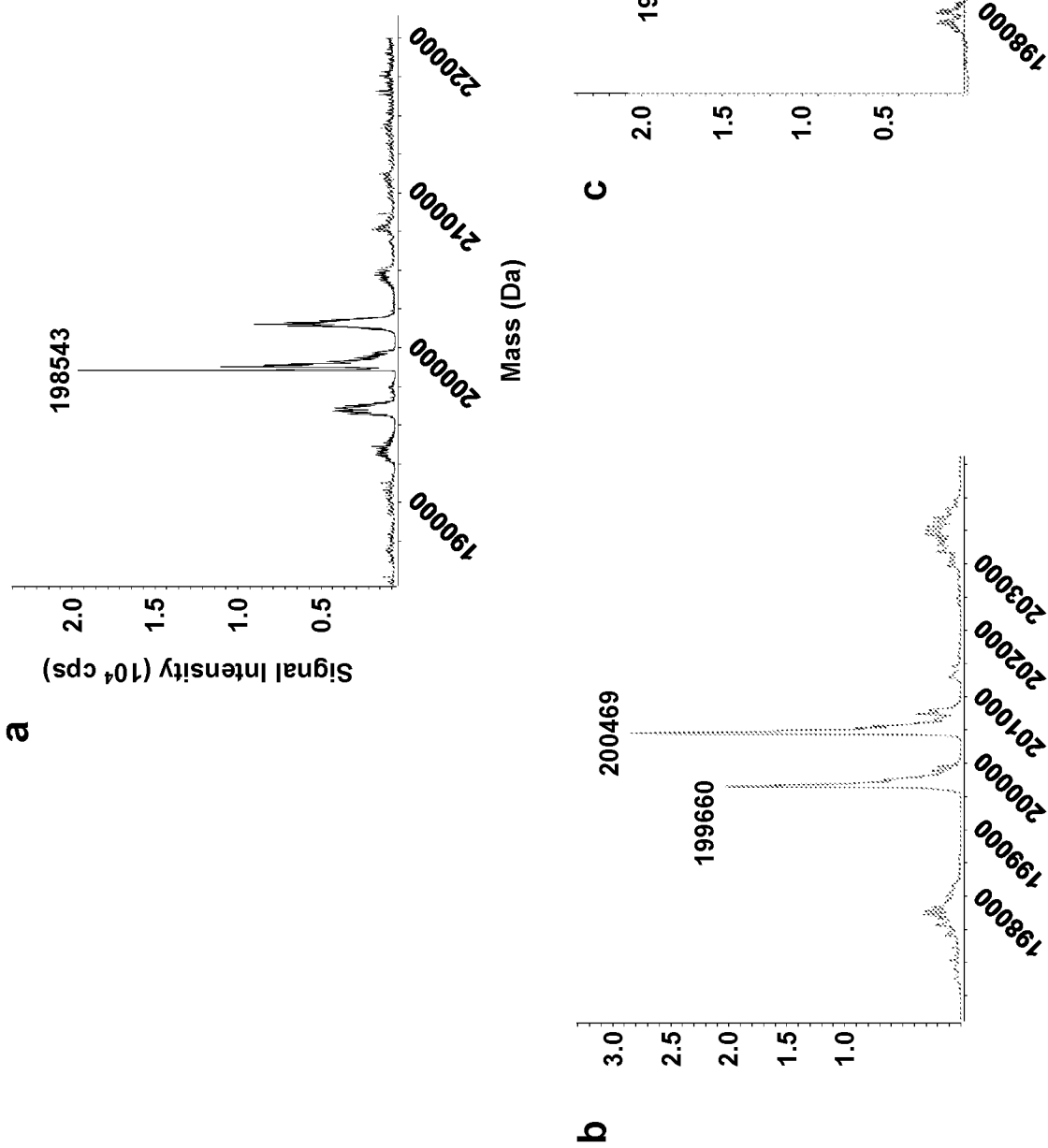
FIG. 13. Mass spectrometry of heterodimeric DVD-IgG1 before and after conjugation to two different payloads. (a) Analysis of the deglycosylated heterodimeric DVD-IgG1 by MALDI-TOF. The expected mass is 198546 Da. (b) MALDI-TOF analysis of the deglycosylated heterodimeric DVD-IgG1 after sequential one-pot conjugation of the phenylglyoxal derivative of TAMRA (compound 1) and the β-lactam hapten derivative of MMAF (compound 5). The expected mass for deglycosylated heterodimeric DVD-IgG1 with one TAMRA and one MMAF payload is 200408 Da. The expected mass for deglycosylated heterodimeric DVD-IgG1 with just the MMAF payload is 199605 Da. (c) Corresponding MALDI-TOF analysis after simultaneous one-pot conjugation.

To test whether the orthogonal conjugation chemistry of h38C2_Arg and h38C2_Lys permits one-pot labeling of the heterodimeric DVD-IgG1 with two different payloads, we combined the phenylglyoxal derivative of TAMRA (compound 1) with a β-lactam hapten derivative of the near infrared fluorescent dye Cy7 (compound 6; FIG. 5). The two dyes were sequentially conjugated to the heterodimeric DVD-IgG1 without intermittent purification or buffer exchange steps (FIG. 12a). Regardless of the order of conjugation, the one-pot reactions yielded dual labeled heterodimeric DVD-IgG1 of the same quality and quantity. Using reducing SDS-PAGE, both TAMRA and Cy7 fluorescence were found to be confined to the heavy chain as expected for site-specific conjugation to h38C2_Arg and h38C2_Lys, respectively (FIG. 12b). We next used the same one-pot assembly for sequential conjugation of the phenylglyoxal derivative of TAMRA (compound 1) and the β-lactam hapten derivative of MMAF (compound 5). MS confirmed the dual labeled heterodimeric DVD-IgG1 with a single TAMRA and a single MMAF payload as the main product although MMAF-labeled heterodimeric DVD-IgG1 without TAMRA payload was also prominent (FIGS. 13a and b). Notably, simultaneous rather than sequential conjugation of compound 1 and compound 5 delivered the dual labeled heterodimeric DVD-IgG1 with similar conjugation efficiency according to MS (FIG. 13c).

Figure 15:
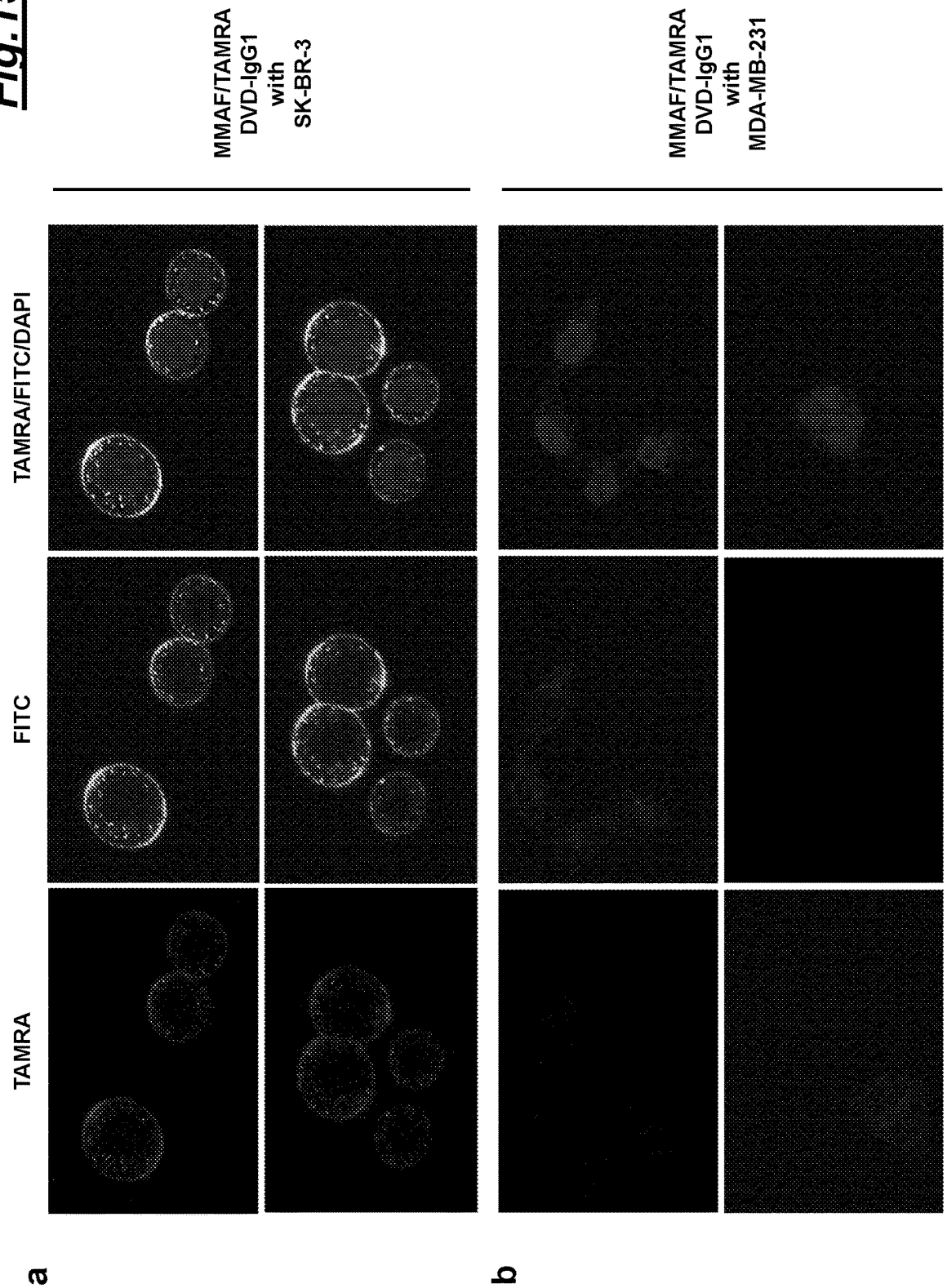
FIG. 15. Internalization and trafficking of heterodimeric DVD-IgG1 with two different payloads. HER2-positive SK-BR-3 cells (a) and HER2-negative MDA-MB-231 cells (b) were incubated with the MMAF (via Lys) and TAMRA (via Arg)-labeled HER2-targeting heterodimeric DVD-IgG1 for 4 h at 37° C. After the incubation, the cells were washed, fixed, blocked, permeabilized, incubated with FITC-conjugated goat anti-human IgG F(ab')2 polyclonal antibodies, washed, stained with DAPI, and washed again before their analysis by confocal fluorescence microscopy.

Dual labeling enables the generation of fluorescent ADCs that can be traced directly during internalization and trafficking. To investigate this utility, we incubated HER2-positive SK-BR-3 (FIG. 14a and FIG. 15a) and HER2-negative MDA-MB-231 cells (FIG. 14b and FIG. 15b) with the MMAF/TAMRA-labeled heterodimeric DVD-IgG1 for 4 h at 37° C. in the absence and presence of endocytosis inhibitor phenylarsine oxide (PAO) and subsequently analyzed the cells by confocal fluorescence microscopy. Endosomal TAMRA fluorescence was only observed for SK-BR-3 cells and in the absence of PAO, suggesting HER2-mediated internalization and trafficking. Simultaneous staining of the heterodimeric DVD-IgG1 carrier with FITC-conjugated goat anti-human IgG F(ab')$_2$ polyclonal antibodies revealed strict co-localization with TAMRA fluorescence, suggesting that the endosomes contained an intact fluorescent ADC. No TAMRA and FITC fluorescence was detected with an h38C2 Lys-based and compound 2-labeled homodimeric DVD-IgG1 in which the outer Fv derived from trastuzumab was replaced with an isotype control outer Fv.

Example 5 Materials and Methods

Cell lines: Breast cancer cell lines SK-BR-3 and MDA-MB-231 were purchased from ATCC and cultured in DMEM supplemented with 10% (v/v) heat inactivated FBS and 1× penicillin-streptomycin (containing 100 U/mL penicillin and 100 mg/mL streptomycin; all from Thermo Fisher). Expi293F cells were cultured in Expi293 expression medium supplemented with 1× penicillin-streptomycin (all from Thermo Fisher).

Cloning, Expression, and Purification of h38C2_Arg Fab, DVD-Fab, and DVD-IgG1:

Fab. Light chain ($V_K$—$C_K$; LC) and heavy chain fragment ($V_H$-$C_H1$; Fd) encoding sequences of h38C2 Fab (Rader et al., J Mol Biol 332, 889-899, 2003) with a Lys99Arg mutation in $V_H$ and an N-terminal human CD5 signal peptide (MPMGSLQPLATLYLLGMLVASVLA) encoding sequence were separately cloned via NheI/XhoI (New England Biolabs) into mammalian expression vector pCEP4. Purified (Qiagen) plasmids encoding LC and Fd were co-transfected into Expi293F cells, which had been grown in 300 mL Expi293 Expression Medium to a density of 3×10$^6$ cells/mL, using the ExpiFectamine 293 Transfection Kit (Thermo Fisher) following the manufacture's instruction. After continued culturing in 300 mL Expi293 Expression Medium at 37° C., 5% $CO_2$ for 5 days, the culture supernatant was collected and purified by affinity chromatography with a 1-mL HiTrap KappaSelect column in conjunction with an AKTA FPLC instrument (both from GE Healthcare). The yield of Fab was ~15 mg/L as determined by the Pierce BCA Protein Assay Kit (Thermo Fisher). The Fab was further purified by size-exclusion chromatography using a Superdex 200 10/300 GL column (GE Healthcare) connected to the AKTA FPLC instrument. Fab peak fractions were concentrated by an Amicon Ultra 0.5-mL Centrifugal Filter (MilliporeSigma) and brought into 0.1 M sodium acetate (pH 5.5).

DVD-Fab. The same LC and Fd expression cassettes as for the Fab extended by $V_K$ and $V_H$ outer domain encoding sequences, respectively, of trastuzumab spaced from the inner domains by ASTKGP (SEQ ID NO:3) encoding sequences were cloned to generate a HER2-targeting h38C2_Arg DVD-Fab, as described in Nanna et al., Nat Commun, 8:1112, 2017. Following expression in the Expi293F system described above, the culture supernatant was collected and purified by affinity chromatography with a 1-mL Protein A HP column (GE Healthcare) in conjunction with the ÄKTA FPLC instrument. The yield of DVD-Fab was ~18 mg/L as determined by the Pierce BCA Protein Assay Kit and its purity was confirmed by SDS-PAGE using a 10-well NUPAGE 4-12% Bis-Tris Protein Gel followed by staining with PageBlue Protein Staining Solution (all from Thermo Fisher). Using the same procedure, a DVD-Fab containing parental h38C2 Lys was cloned, expressed, and purified.

DVD-IgG1. Using the same inner (h38C2_Arg) and outer domain (anti-HER2) encoding sequences as for the DVD-Fab, a DVD-IgG1 was cloned into pCEP4 as described in Nanna et al., Nat Commun, 8:1112, 2017. A heterodimeric DVD-IgG1 that combined an h38C2_Arg heavy chain with a parental h38C2 Lys heavy chain was based on knobs-into-holes mutations in $C_H3$ (see, e.g., Merchant et al., Nat Biotechnol 16, 677-681, 1998; and Qi et al., Proc Natl Acad Sci USA 115, E5467-E5476, 2018). Expression, purification, and analysis of the homodimeric and heterodimeric DVD-IgG1s was identical to the DVD-Fab described above. The yields were ~19 mg/L.

Crystallization and structure determination of h38C2_Arg Fab: Crystals were obtained by vapor diffusion at room temperature (RT) from a precipitant condition containing 20% (w/v) PEG 3350, 40 mM ammonium sulfate, and 200 mM ammonium citrate (pH 4.8). A diffraction data set with Bragg spacings to 2.4 Å was collected on a Pilatus3 6 M detector at the 5.0.1 beamline at the Advanced Light Source synchrotron facility (Lawrence Berkeley National Laboratory). Molecular replacement solution was obtained using PDB ID 3F09 as a search model in PHASER. Crystallographic refinement was performed using a combination of PHENIX 1.12 and BUSTER 2.9. Manual rebuilding, model adjustment, and real space refinements were done using the graphics program COOT. Model figures were created using PYMOL (Schrödinger). The coordinates and structure factors for the final model were deposited in the PDB under ID 6DZR.

Catalytic activity assay: Catalytic activity was analyzed using methadol (List et al., Proc Natl Acad Sci USA 95, 15351-15355, 1998) and carried out exactly as described in Nanna et al., supra.

Synthesis of phenylglyoxal and β-lactam derivatives: The syntheses of compounds 1 (phenylglyoxal-TAMRA), 2 (β-lactam-hapten-TAMRA), 3 (β-lactam-hapten-azide), 4 (phenylglyoxal-MMAF), and 6 (β-lactam-hapten-Cy7) and their characterization by $^1$H-NMR, $^{13}$C-NMR, HRMS, and LC-MS is provided in Example 6 herein. The synthesis of compound 5 (β-lactam-hapten-MMAF) was described previously in Nanna et al., supra.

Antibody conjugation: DVD-Fab conjugation to phenylglyoxal and β-lactam-hapten derivatives. 10 μM h38C2_Arg and h38C2_Lys DVD-Fab were incubated with three different concentrations (10 μM, 50 μM, 100 μM) of phenylglyoxal-TAMRA (compound 1) in 50 mM HEPES, 50 mM NaHCO$_3$ (pH 6.0) for 3 h at 37° C. As a positive control, 10 μM of h38C2 Lys DVD-Fab was incubated with β-lactam-hapten-TAMRA (compound 2) in PBS (pH 7.4) for 3 h at RT in parallel. 7.5 μg of each conjugation mixture was loaded onto a 10-well NuPAGE 4-12% Bis-Tris Protein Gel. Fluorescent bands were visualized by blue light on an E-gel Imager (Thermo Fisher) and the gel was subsequently stained by PageBlue Protein Staining Solution. To test whether DVD-Fab conjugation to phenylglyoxal can be blocked with β-lactam-hapten derivatives, 10 μM h38C2_Arg and h38C2_Lys DVD-Fab were pre-incubated with 100 μM β-lactam-hapten-azide (compound 3) for 3 h at RT and then processed and analyzed as described above. To generate ADCs in DVD-Fab format, 10 μM h38C2_Arg DVD-Fab was incubated with 50 μM phenylglyoxal-MMAF (compound 4) in 50 mM HEPES, 50 mM NaHCO$_3$ (pH 6.0) for 3 h at 37° C. In parallel, 10 μM h38C2_Lys DVD-Fab was incubated with 50 μM β-lactam-hapten-MMAF (compound 5) at RT for 4 h. Following incubation, illustra NAP-5 Columns (GE Healthcare) were used to remove free compounds and the ADCs were concentrated with Amicon Ultra 0.5-mL Centrifugal Filters to 1 mg/mL in PBS (pH 7.4).

DVD-IgG1 conjugation to phenylglyoxal and β-lactam-hapten derivatives. To generate ADCs in DVD-IgG1 format, 10 μM homodimeric h38C2_Arg DVD-IgG1 or heterodimeric h38C2_Arg/h38C2_Lys DVD-IgG1 was incubated with 50 μM phenylglyoxal-MMAF (compound 4) in PBS (pH 6.6) for 3 h at 37° C. In parallel, 10 μM homodimeric h38C2_Lys DVD-IgG1 or heterodimeric h38C2_Arg/h38C2_Lys DVD-IgG1 was incubated with 50 μM β-lactam-hapten-MMAF (compound 5) at RT for 4 h. Following incubation, illustra NAP-5 Columns (GE Healthcare) were used to remove free compounds and the ADCs were concentrated with Amicon Ultra 0.5-mL Centrifugal Filters to 2 mg/mL in PBS (pH 7.4).

Sequential and simultaneous one-pot conjugation of heterodimeric DVD-IgG1 to phenylglyoxal and β-lactam-hapten derivatives. 10 µM heterodimeric h38C2_Arg/h38C2_Lys DVD-IgG1 in PBS (pH 6.6) was sequentially incubated with 50 µM phenylglyoxal-TAMRA (compound 1) for 3 h at 37° C. and then, without purification, with β-lactam-hapten-Cy7 (compound 6) for 3 h at 37° C. The reverse order (compound 6 first and compound 1 second) was carried out in parallel. 5 µg of each conjugation mixture was loaded onto a 10-well NuPAGE 4-12% Bis-Tris Protein Gel. TAMRA conjugation was visualized by blue light on an E-gel Imager and Cy7 conjugation using an Odyssey CLx Imaging System (LI-COR). The gel was subsequently stained by PageBlue Protein Staining Solution. Using the same sequential procedure, a heterodimeric h38C2_Arg/h38C2_Lys DVD-IgG1 conjugated to compound 1 and compound 5 was generated. For instantaneous conjugation, 10 µM heterodimeric h38C2_Arg/h38C2_Lys DVD-IgG1 in PBS (pH 6.6) was simultaneously incubated with 50 µM compound 1 and compound 6 for 3 h at 37° C.

Mass spectrometry: DVD-Fab. Following conjugation of 5 and 10 equivalents of phenylglyoxal-TAMRA (compound 1) or 5 equivalents of phenylglyoxal-MMAF (compound 4) to h38C2_Arg DVD-Fab as described above, illustra NAP-5 Columns were used to remove free compound and the conjugated DVD-Fab was concentrated with Amicon Ultra 0.5-mL Centrifugal Filters to 1 mg/mL in PBS (pH 7.4). Following dilution into water, data were obtained on an Agilent Electrospray Ionization Time of Flight (ESI-TOF) mass spectrometer. Deconvoluted masses were obtained using Agilent BioConfirm Software.

DVD-IgG1. Following conjugation of 5 equivalents of phenylglyoxal-MMAF (compound 4) to h38C2_Arg DVD-IgG1, removal of free compound, and concentration as described above, the conjugated DVD-IgG1 was reduced with 50 mM DTT in PBS for 10 min at RT and then enzymatically deglycosylated by PNGase F (New England Biolabs) overnight at 37° C. The enzyme was removed by a Protein G HP SpinTrap (GE Healthcare) according to the manufacturer's instructions. The conjugated DVD-IgG1 was concentrated with Amicon Ultra 0.5-mL Centrifugal Filters to 2 mg/mL in PBS (pH 7.4). Following dilution into water, ESI-TOF data were acquired as described above. Heterodimeric h38C2_Arg/h38C2_Lys DVD-IgG1 conjugated to phenylglyoxal-TAMRA (compound 1) and β-lactam-hapten-MMAF (compound 5) was deglycosylated without reduction and processed for ESI-TOF data acquisition as described above.

Human plasma stability assay: To assess its stability in human plasma, 1 mg/mL of h38C2_Arg based DVD-Fab conjugated to phenylglyoxal-TAMRA (compound 1) in PBS was mixed with an equal volume of human plasma (Sigma-Aldrich), and incubated at 37° C. After 0, 6, 12, 24, 48, 96, 122, 196, and 240 h, 2-µL aliquots were frozen and stored at −80° C. After aliquots from all time points had been collected, they were analyzed by SDS-PAGE under reducing conditions using a 10-well NuPAGE 4-12% Bis-Tris Protein Gel. Fluorescent bands were visualized by blue light on an E-gel Imager (Thermo Fisher) and the gel was subsequently stained by PageBlue Protein Staining Solution. The experiment was carried out three times independently. Band intensities at 0 and 240 h were quantified by NIH ImageJ software and plotted as mean±SD values.

Cytotoxicity assay: SK-BR-3 and MDA-MB-231 cells were plated in 96-well tissue culture plates at $5\times10^3$ and $3\times10^3$ cells per well. Ten-fold serially diluted ADCs and their corresponding unconjugated DVD-Fab (0.01-100 nM) or DVD-IgG1 (0.001-10 nM) were added to the cells and the plates were incubated at 37° C. in an atmosphere of 5% $CO_2$ for 72 h. Subsequently, cell viability was measured using CellTiter 96 Aqueous One Solution (Promega) following the manufacturer's instructions and plotted as a percentage of untreated cells. $IC_{50}$ values (mean±SD) were calculated by GraphPad Prism software.

Size-exclusion chromatography: Unconjugated and phenylglyoxal-MMAF (compound 4)-conjugated h38C2_Arg based DVD-Fab was analyzed by SEC using a Superdex 200 10/300 GL column (GE Healthcare) connected to an ÄKTA FPLC system. Samples (30 µg in 50 µL PBS) were loaded on the column using 50 mM sodium phosphate, 150 mM NaCl (pH 7.0) as mobile phase and a flow rate of 0.5 mL/min. The percentage of aggregates was determined by integration of peak areas at 280 nm. A Gel Filtration Calibration kit for high molecular weight range (GE Healthcare) was used as standard and included ferritin (F; 440 kDa), aldolase (A; 158 kDa), conalbumin (C; 75 kDa), and ovalbumin (O; 44 kDa).

Surface plasmon resonance: SPR for the measurement of kinetic and thermodynamic parameters of the binding of unconjugated and conjugated DVD-Fab to HER2 were performed on a Biacore X100 instrument using Biacore reagents and software (GE Healthcare). A mouse anti-human IgG $C_H2$ mAb was immobilized on a CM5 sensor chip using reagents and instructions supplied with the Human Antibody Capture Kit (GE Healthcare). Human HER2-Fc fusion protein (R & D Systems) was captured at a density not exceeding 300 RU. Each sensor chip included an empty flow cell for instantaneous background depletion. All binding assays used 1×HBS-EP+ running buffer (10 mM HEPES, 150 mM NaCl, 3 mM EDTA (pH 7.4), and 0.05% (v/v) Surfactant P20) and a flow rate of 30 µL/min. For affinity measurements, all DVD-Fab were injected at five different concentrations. At least two independent experiments for each sample were carried out. The sensor chips were regenerated with 3 M $MgCl_2$ from the Human Antibody Capture Kit without any loss of binding capacity. Calculation of association ($k_{on}$) and dissociation ($k_{off}$) rate constants was based on a 1:1 Langmuir binding model. The equilibrium dissociation constant ($K_D$) was calculated from $k_{off}/k_{on}$.

Confocal fluorescence microscopy: SK-BR-3 and MDA-MB-231 cells were seeded in 35-mm Nunc Glass Bottom Dishes (Thermo Fisher) at $5\times10^4$ cells per dish. TAMRA (compound 1)/MMAF (compound 5)-labeled heterodimeric h38C2_Arg/h38C2_Lys DVD-IgG1 was added to a final concentration of 5 µg/mL in the presence or absence of 10 µM PAO (Sigma-Aldrich). TAMRA (compound 2)-labeled homodimeric h38C2_Lys DVD-IgG1 in which the outer Fv derived from trastuzumab was replaced with the outer Fv of a humanized version of rabbit anti-human ROR2 mAb XBR2-401 (Peng et al., *J Mol Biol* 429, 2954-2973, 2017) was used as negative control. (SK-BR-3 and MDA-MB-231 cells do not express ROR2). After 4 h incubation, the cells were washed with cold PBS three times to stop internalization, and fixed with 4% (w/v) paraformaldehyde (Alfa Aesar) for 15 min at RT. Then, 0.2 M glycine-HCl (pH 2.0) was added for 5 min to remove extracellular bound antibodies. Samples were blocked with 2% (w/v) BSA in PBS for 1 h after permeabilization with 0.2% (v/v) Triton X-100 for 15 min at RT. After washing with cold PBS three times, the samples were incubated for 1 h with FITC-conjugated goat anti-human IgG F(ab')$_2$ polyclonal antibodies (Thermo Fisher) diluted in 2% (w/v) BSA in PBS. After washing with cold PBS three times, samples were stained with 4',6-diamidino-2-phenylindole (DAPI, Thermo Fisher) diluted in PBS for 10 min and washed again with cold PBS three times. Images were captured on a Zeiss LSM 880 confocal system at the Light Microscopy Facility of the Max Planck Florida Institute of Neuroscience (Jupiter, FL).

Example 6 Additional Technical Information for the Exemplified Embodiments

General Information: All non-aqueous reactions were performed in an oven-dried or a flame-dried glassware under argon atmosphere. Unless otherwise mentioned, all reagents were purchased from commercial suppliers and used without further purification. Dichloromethane, tetrahydrofuran and N,N-dimethylformamide were purified by passing through a solvent column of desiccant (activated A1-alumina). Methanol was purchased as a reagent grade solvent. Diisopropylethylamine and triethylamine were distilled from calcium hydride under argon atmosphere. All reactions were monitored by either thin-layer chromatography or analytical LCMS. Thin-layer chromatography was performed on Merck TLC silica gel 60 F254 glass plates pre-coated with 0.25 mm thickness. Visualization was done by UV light (254 nm), $KMnO_4$ stain, phosphomolybdic acid (PMA) stain, triphenylphosphine solution and/or ninhydrin stain. Purification by preparative thin-layer chromatography was performed on Analtech UNIPLATE silica gel GF UV 254 20×20 cm, 2000 micron thickness. Purification on silica gel column chromatography was performed on SiliFlash F60 (40-63 μm, 230-400 mesh). Preparative HPLC purification was performed on Shimadzu LC-8A preparative liquid chromatography with mobile phase A $H_2O$+0.1% TFA/mobile phase B 1:1 $CH_3OH$:$CH_3CN$ or mobile phase A $H_2O$/mobile phase B: $CH_3CN$. $^1$H-NMR spectra were recorded on a Bruker 400 MHz, 600 MHz, or 700 MHz spectrometer in appropriate deuterated solvents. $^{13}$C-NMR spectra were recorded at 100 MHz, 150 MHz or 175 MHz. Chemical shifts were reported in parts per million (ppm) on the S scale from residue solvent peaks. NMR descriptions: s, singlet; d, doublet; t, triplet; q, quartet; m, multiplet; br, broad. Coupling constants, J, are reported in Hertz (Hz). Infrared spectra (IR) were recorded on a PerkinElmer Spectrum One FT-IR spectrometer with universal ATR sampling accessory as thin films (neat). High-resolution mass spectra were obtained from a spectrometer (ESI) at the University of Illinois Urbana-Champaign Mass Spectrometry Laboratory. The purity of any materials using in biological experiments were determined by analytical LCMS to be >95%.

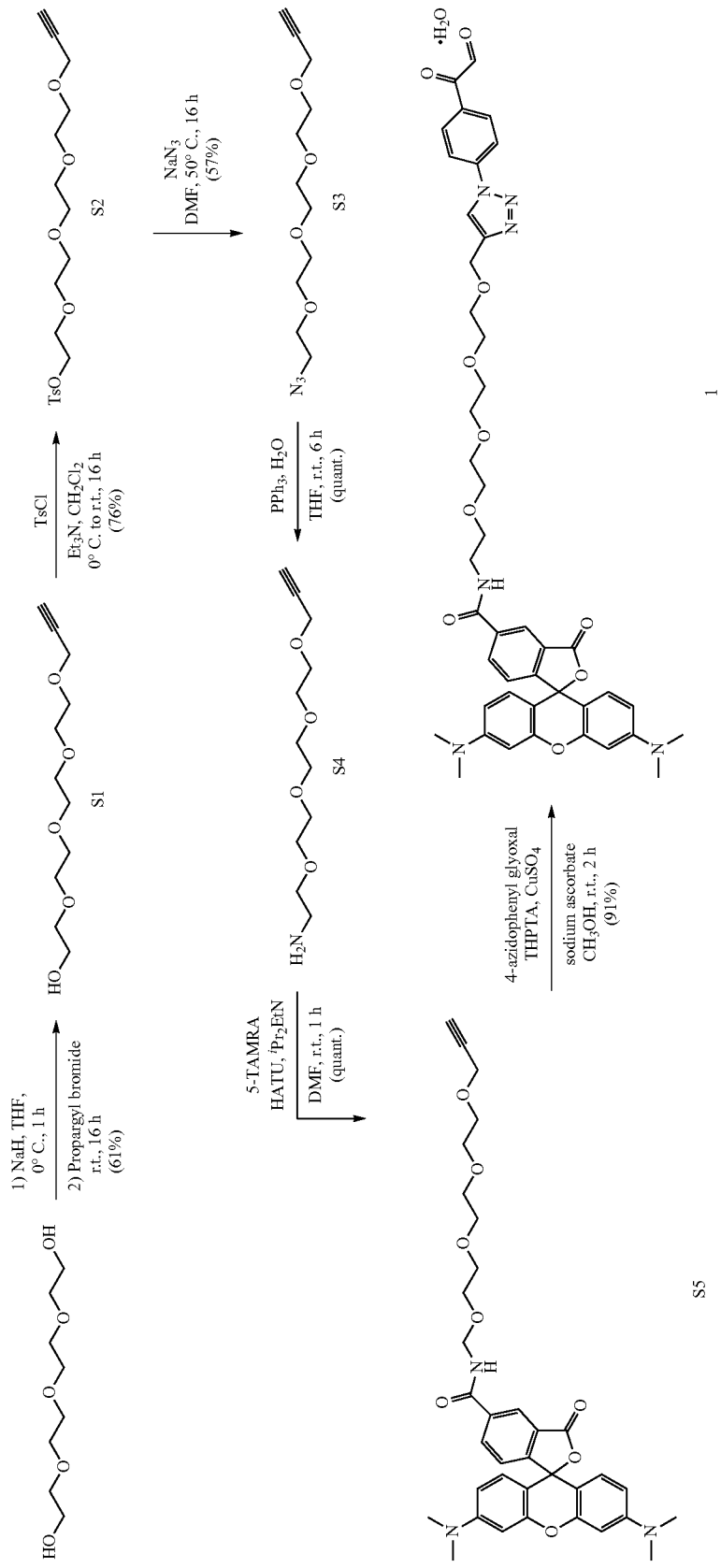

Synthesis of compound S1. A solution of tetraethylene glycol (6.0 ml, 34.8 mmol) in THF (17 ml) was cooled down to 0° C. and added with sodium hydride (0.903 g, 22.59 mmol). The reaction was stirred at 0° C. for 1 h. Propargyl bromide (1.5 ml, 16.83 mmol) was then added into the cooled solution. The reaction was the allowed to warm up to room temperature and stirred for 16 h. The reaction was quenched with ice-cold water. The mixture was extracted with $CH_2Cl_2$, washed with brine, dried over anhydrous $Na_2SO_4$, filtered and concentrated. The crude mixture was purified with silica gel column chromatography (visualized TLC with $KMnO_4$ stain). The product was obtained as clear colorless viscous liquid (2.37 g, 61%). $^1$H-NMR (400 MHz, Chloroform-d) δ 4.18 (d, J=2.4 Hz, 2H), 3.72-3.55 (m, 17H), 2.77 (s, 1H), 2.42 (t, J=2.4 Hz, 1H). IR (neat) 3448.93, 3249.92, 2920.77, 2856.78, 2113.97. HRMS calcd for $C_{11}H_{20}O_5Na$ [M+Na]$^+$255.1209 found 255.1207.

Synthesis of compound S2. S1 (0.8 g, 3.44 mmol) and triethylamine (1.440 ml, 10.33 mmol) were dissolved in $CH_2Cl_2$ (6 mL) and cooled down to 0° C. A solution of tosyl chloride (0.788 g, 4.13 mmol) in $CH_2Cl_2$ (3 mL) was then added to the cooled solution. The reaction was then allowed to warm up to room temperature and stirred for 16 h. The reaction was quenched with saturated aqueous $NH_4Cl$. The mixture was extracted with $CH_2Cl_2$, washed with 1 M HCl, water, and brine, respectively. The organic phase was then dried over anhydrous $Na_2SO_4$, filtered and concentrated to dryness. The crude mixture was purified with silica gel column chromatography. The product was obtained as clear colorless viscous liquid (1.01 g, 76%). $^1$H-NMR (400 MHz, Chloroform-d) δ 7.79 (d, J=8.3 Hz, 2H), 7.33 (dt, J=7.9, 0.7 Hz, 2H), 4.18 (d, J=2.4 Hz, 2H), 4.16-4.12 (m, 2H), 3.71-3.60 (m, 10H), 3.57 (s, 4H), 2.44 (s, 3H), 2.42 (t, J=2.4 Hz, 1H). HPLC-MS calcd for $C_{18}H_{27}O_7S$ [M+H]$^+$ 387.15 found 387.37.

Synthesis of compound S3. S2 (986 mg, 2.55 mmol) was dissolved in DMF (5 mL) and then added with sodium azide (415 mg, 6.38 mmol). The reaction suspension was stirred in a 50° C. oil bath for 16 h. DMF was then evaporated. The yellow residue was suspended in diethyl ether. Pale yellow precipitate was filtered off by a syringe packed with a plug of cotton wools. The obtained clear yellow solution was dried under reduced pressure. The residue was purified with silica gel column chromatography (50% EtOAc/hexanes to 100% EtOAc, visualized TLC with 10% $PPh_3$ solution followed by ninhydrin stain). The product was obtained as clear pale yellow viscous liquid (0.37 g, 57%). $^1$H-NMR (400 MHz, Chloroform-d) δ 4.20 (d, J=2.4 Hz, 2H), 3.74-3.61 (m, 14H), 3.42-3.34 (m, 2H), 2.43 (t, J=2.4 Hz, 1H). IR (neat) 3254.23, 2867.67, 2098.15.

Synthesis of compound S4. S3 (370 mg, 1.438 mmol) was dissolved THF (3.0 ml) and added with triphenyl phosphine (754 mg, 2.88 mmol) followed by water (0.026 ml, 1.438 mmol). The reaction was stirred at room temperature for 6 h. The reaction was then dried under vacuum. Viscous yellow residue was purified by silica gel column chromatography (2% to 10% $CH_3OH/CH_2Cl_2$ followed by 10% $CH_3OH/CH_2Cl_2$+1% $Et_3N$, visualized with ninhydrin or $KMnO_4$ stain). The product was obtained as pale yellow viscous liquid (0.33 g, 100%). $^1$H-NMR (400 MHz, Chloroform-d) δ 4.22 (d, J=2.4 Hz, 2H), 3.64 (s, 14H), 2.99 (d, J=5.3 Hz, 2H), 2.47 (t, J=2.4 Hz, 1H). IR (neat) 3363.42, 3244.98, 2868.66, 2111.92. HRMS calcd for $C_{11}H_{22}NO_4$ [M+H]$^+$ 232.1549 found 232.1557.

Synthesis of compound S5. 5-TAMRA (20.0 mg, 0.046 mmol) and HATU (17.67 mg, 0.046 mmol) were dissolved in DMF (250 μL). The mixture solution was added with DIPEA (40 μl, 0.229 mmol) and stirred at room temperature for 10 min. Then a solution of S4 (11.82 mg, 0.051 mmol) in DMF (150 μl) was added to the activated TAMRA solution. The reaction was stirred at room temperature for 1 h (LCMS of the reaction showed complete consumption of 5-TAMRA). The reaction was dried under vacuum and the remaining residue was purified by preparative thin-layer chromatography (5%, 7.5%, and 10% $CH_3OH/CH_2Cl_2$). The product band was scraped off and suspended in 10% $CH_3OH/CH_2Cl_2$. The silica gel suspension was passed through a short plug of silica gel, washed off by 10% $CH_3OH/CH_2Cl_2$+0.05% TFA. The filtrate was evaporated and then dried under high vacuum to yield dark purple viscous residue. The residue was dissolved in 10% $^iPrOH/CH_2Cl_2$ and washed with 1:1 mixture of water: saturated $NaHCO_3$. The aqueous layer was extracted with 10% $^iPrOH/CH_2Cl_2$ until the organic phase is no longer pink. The combined organic phase was washed with brine, and evaporated to dryness to yield the product as dark purple solid (30.6 mg, 102%). $^1$H-NMR (400 MHz, Methanol-$d_4$) δ 8.77 (d, J=1.8 Hz, 1H), 8.26 (dd, J=7.9, 1.8 Hz, 1H), 7.52 (d, J=7.9 Hz, 1H), 7.12 (d, J=9.5 Hz, 2H), 7.04 (dd, J=9.5, 2.4 Hz, 2H), 6.95 (d, J=2.4 Hz, 2H), 4.12 (d, J=2.4 Hz, 2H), 3.77-3.69 (m, 2H), 3.69-3.58 (m, 14H), 3.28 (s, 12H), 2.80 (t, J=2.4 Hz, 1H). $^{13}$C-NMR (101 MHz, Methanol-$d_4$) δ 168.24, 167.34, 160.66, 158.94, 138.11, 137.69, 132.82, 131.94, 131.38, 115.57, 114.72, 97.46, 80.58, 75.98, 71.60, 71.54, 71.49, 71.32, 70.46, 70.07, 59.01, 41.25, 40.95. HRMS calcd for $C_{36}H_{42}N_3O_8$ [M+H]$^+$ 644.2972 found 644.2977.

Synthesis of compound 1. To a solution of S5 (7.8 mg, 0.012 mmol) and hydrated 4-azidophenyl glyoxal (3.51 mg, 0.018 mmol) in $CH_3OH$ (544 μl) was added aqueous solution of 50 mM THPTA (60.6 μl, 3.03 μmol), 50 mM copper(II) sulfate (60.6 μl, 3.03 μmol), and 100 mM sodium ascorbate (6.06 μl, 6.06 μmol) at room temperature. The reaction was stirred at room temperature for 1 h and then evaporated under reduced pressure to remove methanol. The aqueous residue was stirred with 200 mg of Quadra pure TU resin (pre-swelled in THF for 30 min) for 3 h. The reaction was filtered through 0.2 μM PFTE filter and purified with preparative HPLC (254 nm). The fractions containing product were evaporated to remove acetonitrile. The remaining aqueous solution was lyophilized to give the product as a dark purple powder (7.3 mg, 72%). $^1$H-NMR (700 MHz, Methanol-$d_4$) δ 8.69 (d, J=1.9 Hz, 1H), 8.51 (s, 1H), 8.20 (d, J=8.8 Hz, 2H), 8.17 (dd, J=7.8, 1.8 Hz, 1H), 7.93 (d, J=8.8 Hz, 2H), 7.42 (d, J=7.8 Hz, 1H), 7.11 (dd, J=9.5, 3.3 Hz, 2H), 6.95 (ddd, J=9.5, 3.9, 2.5 Hz, 2H), 6.80 (dd, J=3.9, 2.5 Hz, 2H), 5.50 (s, 1H), 4.64 (s, 2H), 3.72 (dd, J=5.8, 4.7 Hz, 2H), 3.69-3.61 (m, 12H), 3.26 (d, J=1.2 Hz, 12H). $^{13}$C NMR (176 MHz, Methanol-$d_4$) δ 194.52, 168.55, 160.99, 158.82, 158.70, 147.33, 141.48, 137.68, 137.45, 134.79, 132.52, 132.09, 131.52, 131.29, 130.76, 123.04, 120.63, 120.39, 115.33, 115.31, 114.62, 97.35, 97.25, 71.61, 71.60, 71.51, 71.38, 71.01, 70.43, 65.00, 41.26, 40.88. HRMS calcd for $C_{44}H_{49}N_6O_{11}$ [M+H]$^+$ 837.3459 found 837.3440

Scheme 2. Synthesis of azide-β-lactam (2) and TAMRA-β-lactam (3)

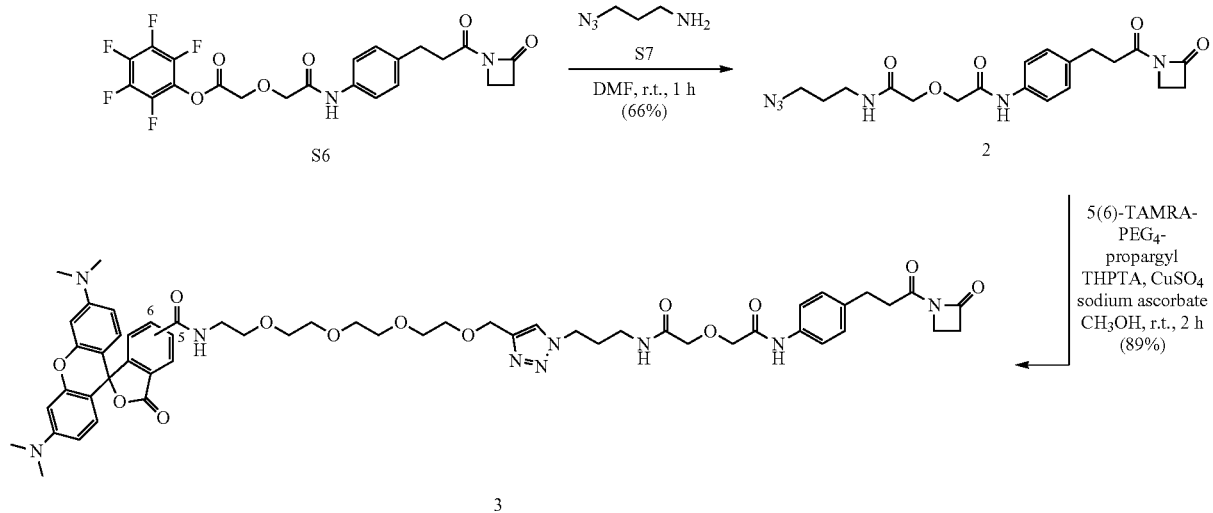

S6 was synthesized according to procedure reported by Magano J. et al. (Org. Process Res. Dev., 2014, 18:142-151). ¹H-NMR (400 MHz, Chloroform-d) δ 8.43 (s, 1H), 7.50-7.46 (m, 2H), 7.23-7.19 (m, 2H), 4.64 (s, 2H), 4.28 (s, 2H), 3.56 (t, J=5.5 Hz, 2H), 3.05-2.93 (m, 6H).

S7 was synthesized according to the procedure reported by Smith B. D. et al. (J. Org. Chem. 2008, 73, pp 6053-6058). 1H-NMR (400 MHz, Chloroform-d) δ 3.33 (t, J=6.7 Hz, 2H), 2.75 (t, J=6.8 Hz, 2H), 1.68 (p, J=6.8 Hz, 2H). IR (neat) 3371.92, 2936.85, 2869.87, 2089.28.

Synthesis of compound 2. S6 (15.0 mg, 0.030 mmol) in 200 μL anhydrous DMF was added a solution of S7 (6.00 mg, 0.060 mmol) in 120 μL anhydrous DMF. The reaction was stirred at room temperature for 1 h. The product was purified with silica gel column chromatography (8.2 mg, 66%). ¹H-NMR (400 MHz, Chloroform-d) δ 8.35 (s, 1H), 7.47 (d, J=8.5 Hz, 2H), 7.21 (d, J=8.5 Hz, 2H), 6.77 (s, 1H), 4.16 (s, 2H), 4.12 (s, 2H), 3.56 (t, J=5.3 Hz, 2H), 3.47-3.38 (m, 4H), 3.08-2.91 (m, 6H), 1.84 (p, J=6.6 Hz, 2H). ¹³C-NMR (101 MHz, CDCl3) δ 170.20, 168.69, 166.58, 165.14, 137.13, 135.20, 129.29, 120.44, 71.61, 71.40, 49.74, 38.15, 37.17, 36.65, 36.00, 29.54, 28.75. HRMS calcd for $C_{19}H_{26}N_6O_{54}Na$ [M+H]⁺ 417.1886 found 417.1883.

Synthesis of compound 3. To a solution of 2 (9.32 mg, 0.022 mmol) and 5(6)-TAMRA-PEG4-propargyl (7.2 mg, 0.011 mmol) in $CH_3OH$ (502 μl) was added 50 mM THPTA (55.9 μl, 2.80 μmol), 50 mM copper (II) sulfate (55.9 μl, 2.80 μmol), and 100 mM sodium ascorbate (55.9 μl, 2.80 μmol). The reaction was stirred at room temperature for 2 h. The reaction was filtered through 0.2 μM PFTE filter and purified with preparative HPLC (254 nm). The fractions containing product were combined and evaporated to remove acetonitrile. The remaining aqueous solution was lyophilized to give the product as a dark purple powder (12.8 mg, 89%, 2TFA salt). 5- and 6-isomer mixture ¹H-NMR (400 MHz, Methanol-d₄) δ 8.77 (d, J=1.8 Hz, 0.5H), 8.39 (d, J=8.2 Hz, 0.5H), 8.24 (ddd, J=21.7, 8.1, 1.8 Hz, 1H), 7.99 (s, 1H), 7.84 (d, J=1.8 Hz, 0.5H), 7.49 (dd, J=12.2, 8.3 Hz, 2.5H), 7.21-7.09 (m, 4H), 7.02 (dt, J=9.4, 2.7 Hz, 2H), 6.95 (d, J=2.4 Hz, 2H), 4.57 (d, J=7.9 Hz, 2H), 4.47-4.41 (m, 2H), 4.17 (d, J=3.2 Hz, 2H), 4.08 (d, J=3.9 Hz, 2H), 3.66 (m, 22H), 3.29 (s, 12H), 3.03 (t, J=5.3 Hz, 2H), 2.92 (m, 4H), 2.13 (m, 2H). HRMS calcd for $C_{55}H_{66}N_9O_{13}$ [M+H]⁺ 1060.4780 found 1060.4779.

Scheme 3. Synthesis of MMAF-TPG (4)

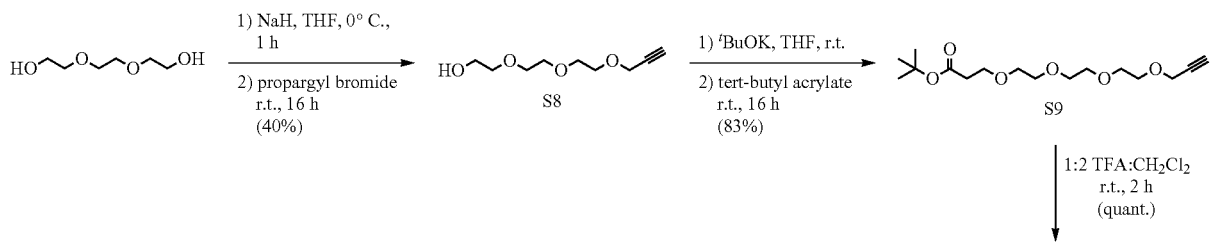

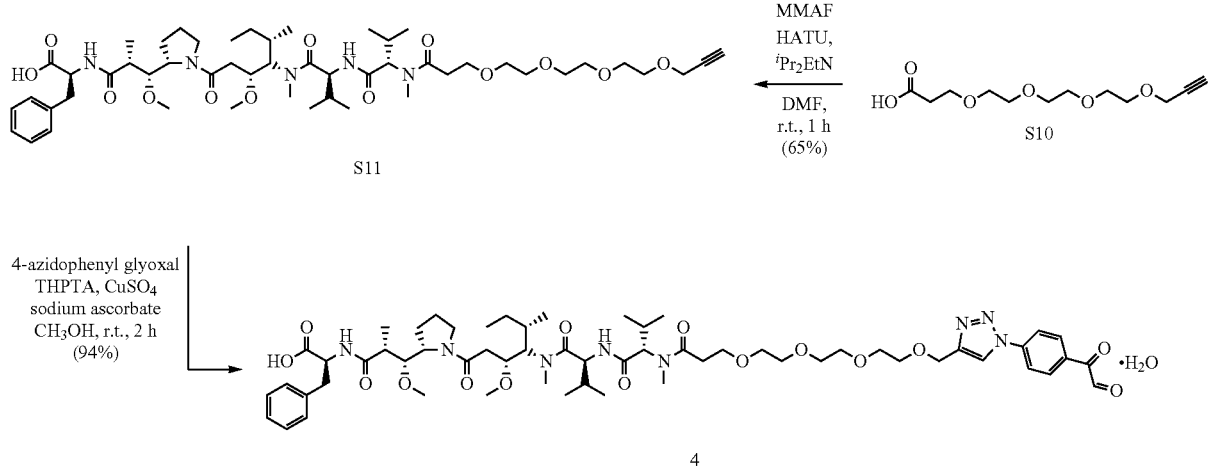

Synthesis of compound S8. A solution of triethylene glycol (6 ml, 44.9 mmol) in THF (22.45 ml) was cooled down to 0° C. and added with sodium hydride (1.167 g, 29.2 mmol). The reaction was stirred at 0° C. for 1 h. Propargyl bromide (1.5 ml, 16.83 mmol) was then added. The reaction was stirred at room temperature for 16 h. The reaction was quenched with ice-cold water, extracted with $CH_2Cl_2$, washed with brine, dried over anhydrous $Na_2SO_4$, filtered and concentrated down. The crude mixture was purified with silica gel column chromatography. The product was obtained as clear colorless viscous liquid (1.71 g, 40%). $^1$H-NMR (400 MHz, Chloroform-d) δ 4.19 (d, J=2.4 Hz, 2H), 3.75-3.63 (m, 10H), 3.62-3.56 (m, 2H), 2.49 (s, 1H), 2.43 (t, J=2.4 Hz, 1H). IR (neat) 3451.22, 3250.90, 2869.21, 2112.49. HRMS calcd for $C_9H_{16}O_4Na$ [M+Na]$^+$ 211.0946 found 211.0947.

Synthesis of compound S9. A solution of S8 (200 mg, 1.063 mmol) in THF (0.5 ml) was added potassium tert-butoxide (5.96 mg, 0.053 mmol). The reaction was then added dropwise with tert-butyl acrylate (177 mg, 1.381 mmol). The reaction was stirred at room temperature for 16 h. The reaction was neutralized with 1 M HCl then partitioned with $CH_2Cl_2$ and brine. The organic phase was extracted, dried over anhydrous $Na_2SO_4$, filtered and concentrated under reduced pressure. The crude mixture was purified with silica gel column chromatography. The product was obtained as clear colorless viscous liquid (0.28 g, 83%). $^1$H-NMR (400 MHz, Chloroform-d) δ 4.20 (d, J=2.4 Hz, 2H), 3.77-3.53 (m, 14H), 2.50 (t, J=6.6 Hz, 2H), 2.42 (t, J=2.4 Hz, 1H), 1.44 (s, 9H). IR (neat) 3258.87, 2976.71, 2869.31, 2114.65, 1727.05. HPLC-MS calcd for $C_{16}H_{29}NaO_6$ [M+H+Na]$^+$ 340.19, found 340.45.

Synthesis of compound 510. A solution of S9 (273.0 mg, 0.863 mmol) in $CH_2Cl_2$ (2.7 ml) was added with trifluoroacetic acid (1.4 ml, 18.17 mmol). The reaction was stirred at room temperature for 2 h. After TLC showed complete consumption of starting material, TFA was co-evaporated with toluene/$CH_2Cl_2$ 3 times. Slightly yellow clear viscous liquid product was dried under high vacuum and used without further purification. $^1$H-NMR (400 MHz, Chloroform-d) δ 4.21 (d, J=2.4 Hz, 2H), 3.77 (t, J=6.2 Hz, 2H), 3.73-3.58 (m, 12H), 2.64 (t, J=6.1 Hz, 2H), 2.43 (t, J=2.4 Hz, 1H). IR (neat) ~3500-2500 (very broad), 3257.04, 2876.00, 2115.78, 1716.74. HRMS calcd for $C_{12}H_{20}O_6Na$ [M+Na]$^+$ 283.1158 found 283.1164.

Synthesis of compound S11. S10 (6.15 mg, 0.024 mmol), HATU (8.09 mg, 0.021 mmol) were dissolved with DMF (100 μl). The solution was then added with DIPEA (10.32 μl, 0.059 mmol). The mixture was stirred at room temperature for 10 min. A solution of MMAF TFA salt (10 mg, 0.012 mmol, Levena Biopharma) in DMF (100 μl) was then added to the solution of activated acid. The reaction was stirred at room temperature for 1 h. The reaction was filtered through 0.2 μM PFTE and purified with preparative HPLC (210 nm). Fractions containing product were evaporated and lyophilized to give the product as white solid. $^1$H-NMR (400 MHz, Chloroform-d) δ 8.33 (d, J=8.3 Hz, 0.38H), 8.16 (dq, J=18.3, 9.7, 9.1 Hz, 0.47H), 7.90 (d, J=8.3 Hz, 0.27H), 7.83 (d, J=8.6 Hz, 0.36H), 7.33-7.13 (m, 5.00H), 4.78-4.53 (m, 2.8H), 4.19 (t, J=1.9 Hz, 2.09H), 4.17-3.89 (m, 1.88H), 3.88-3.74 (m, 2.77H), 3.73-3.57 (m, 13.84H), 3.46-3.33 (m, 5.94H), 3.26-3.05 (m, 5.96H), 3.01-2.62 (m, 5.53H), 2.56-2.40 (m, 2.04H), 2.39-2.19 (m, 2.25H), 2.18-1.95 (m, 1.86H), 1.95-1.69 (m, 3.11H), 1.58 (ddt, J=31.6, 13.1, 7.1 Hz, 1.09H), 1.49-1.35 (m, 1.66H), 1.34-1.25 (m, 1.11H), 1.20 (d, J=6.6 Hz, 1.47H), 1.15 (dd, J=6.5, 3.3 Hz, 1.81H), 1.12-0.75 (m, 20.88H). HRMS calcd for $C_{51}H_{84}N_5O_{13}$ [M+H]$^+$ 974.6065 found 974.6036.

Synthesis of compound 4. S11 (7.5 mg, 7.70 μmol) was mixed with a solution of hydrated 4-azidophenyl glyoxal (2.231 mg, 0.012 mmol) in $CH_3OH$ (345 μl). Then aqueous solution of 50 mM THPTA (38.5 μl, 1.925 μmol), 50 mM copper (II) sulfate (38.5 μl, 1.925 μmol), and 100 mM sodium ascorbate (38.5 μl, 3.85 μmol) were added. LCMS of crude reaction showed complete consumption of alkyne starting material at 2 h. The reaction was evaporated to remove $CH_3OH$. Aqueous residue was diluted with water and passed through a plug of basic activated lumina and through 0.2 μM PFTE filter, purified with preparative HPLC. (monitored at 210 nm) to give product as off-white powder (8.5 mg, 94%). $^1$H-NMR (600 MHz, DMSO-$d_6$) δ 9.52 (s, 0.04H), 8.93 (s, 0.86H), 8.54 (dd, J=9.0, 5.5 Hz, 0.51H), 8.35 (dd, J=8.7, 2.0 Hz, 0.35H), 8.27 (d, J=8.8 Hz, 1.62H), 8.14 (dd, J=14.7, 8.1 Hz, 0.59H), 8.08 (d, J=8.9 Hz, 1.67H), 7.95 (s, 0.08H), 7.92-7.84 (m, 0.09H), 7.76 (d, J=8.3 Hz, 0.24H), 7.66 (d, J=8.5 Hz, 0.25H), 7.27-7.11 (m, 5.00H), 7.10 (s, 0.07H), 7.02 (s, 0.07H), 5.68 (s, 0.74H), 4.64 (s, 2H), 4.73-4.36 (m, 4H), 3.64-3.60 (m, 5.05H), 3.56 (t, J=6.0, 3.7 Hz, 2.88H), 3.53-3.41 (m, 10.81H), 3.32-3.12 (m, 8.80H), 3.12-2.99 (m, 2.95H), 2.95 (d, J=6.1 Hz, 1.41H), 2.92 (d, J=9.0 Hz, 1.37H), 2.88 (s, 0.34H), 2.85-2.70 (m, 3.73H), 2.67-2.52 (m, 1.61H), 2.45-2.28 (m, 1.71H), 2.26-1.84 (m, 4.56H), 1.84-1.57 (m, 3.21H), 1.48-1.17 (m, 2.79H), 1.05 (d, J=6.7 Hz, 1.05H), 1.01 (d, J=6.7 Hz, 1.06), 0.97-0.61 (m, 20.04H). $^{13}$C-NMR (151 MHz, DMSO) δ 195.61, 189.15, 187.05, 173.90, 173.86, 173.82, 173.71, 173.60, 173.47, 173.00, 172.93, 171.66, 171.62, 171.12, 171.09, 170.15, 170.07, 170.03, 169.44, 169.29, 169.16, 162.79, 159.02, 158.78, 158.54, 158.30, 145.95, 140.03, 138.19, 137.94, 133.64, 131.79, 131.77, 131.53, 129.59, 129.41, 129.38, 129.17, 129.10, 128.59, 128.57, 128.49, 126.75, 126.68, 122.89, 122.81, 120.25, 120.00, 119.98, 90.21, 90.20, 85.82, 81.84, 67.51, 67.25, 64.69, 63.85, 63.80, 61.49, 61.41, 61.25, 61.14, 60.66, 58.98, 58.65, 57.59, 57.54, 56.24, 55.57, 54.62, 54.55, 54.44, 53.47, 53.20, 52.36, 47.71, 47.56, 46.72, 46.61, 43.87, 43.55, 43.37, 36.82, 33.91, 33.62, 33.59, 32.08, 32.05, 31.74, 31.24, 31.08, 30.67, 30.64, 30.44, 30.38, 28.92, 28.88, 27.90, 26.86, 26.75, 26.18, 25.75, 25.71, 25.66, 25.04, 24.73, 23.57, 19.64, 19.60, 19.37, 19.23, 19.20, 19.11, 18.98, 18.92, 18.86, 18.72, 18.64, 16.10, 16.04, 15.87, 15.83, 15.65, 15.56, 15.49, 15.32, 10.87, 10.68. HRMS calcd for $C_{59}H_{91}N_8O_{16}$ [M+H]$^+$ 1167.6553 found 1167.6531

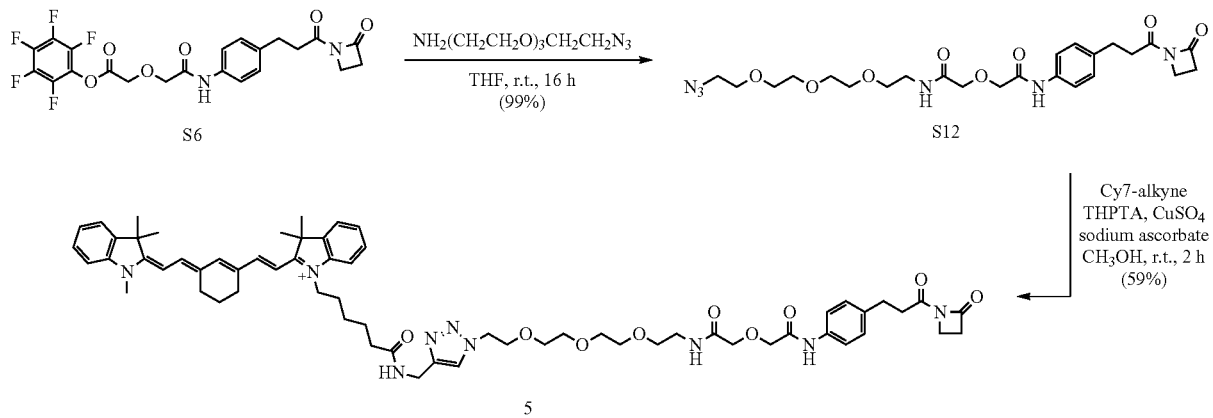

Scheme 4. Synthesis of Cy7-β-lactam (3)

Synthesis of compound S12. S6 (50.0 mg, 0.100 mmol) was dissolved in 200 μL THF. A solution of 2-(2-(2-(2-azidoethoxy)ethoxy)ethoxy)ethan-1-amine (36.0 mg, 0.165 mmol) in 200 μL THF was then added to the reaction vial. The reaction was stirred at room temperature for 16 h. The reaction was concentrated under reduced pressure and purified by silica gel column chromatography (1% CH$_3$OH/CH$_2$Cl$_2$ to 10% CH$_3$OH/CH$_2$Cl$_2$) to give the desired product as clear colorless viscous liquid (53.0 mg, 99%). $^1$H NMR (400 MHz, DMSO-d$_6$) δ 9.95 (s, 1H), 8.14 (t, J=5.7 Hz, 1H), 7.53 (d, J=8.5 Hz, 1H), 7.18 (d, J=8.5 Hz, 2H), 4.13 (s, 2H), 4.04 (s, 2H), 3.62-3.55 (m, 3H), 3.52 (s, 8H), 3.46 (td, J=5.6, 3.7 Hz, 4H), 3.38 (dd, J=5.6, 4.3 Hz, 2H), 3.33-3.25 (m, 2H), 3.04 (t, J=5.3 Hz, 2H), 2.85 (d, J=43.2 Hz, 4H). $^{13}$C NMR (101 MHz, DMSO) δ 169.39, 169.00, 167.59, 165.75, 136.31, 135.93, 128.49, 119.99, 70.66, 70.51, 69.78, 69.74, 69.67, 69.56, 69.23, 68.88, 49.97. HRMS calcd for $C_{24}H_{35}N_6O_8$ [M+H]$^+$ 535.2516 found 535.2523.

Synthesis of compound 3. A solution of Cyanine 7-alkyne (2.0 mg, 3.21 μmol, Lumiprobe Corporation) and compound 3 (2.062 mg, 3.86 μmol) in CH$_3$OH (144 μl) was treated with aqueous solution 50 mM THPTA (16.07 μl, 0.803 μmol), 50 mM copper (II) sulfate (16.07 μl, 0.803 μmol) and 100 mM sodium ascorbate (16.07 μl, 1.607 μmol). The reaction was stirred at room temperature for 2 h. The crude reaction was filtered through 0.2 μM PFTE filter and purified with preparative HPLC. The fraction containing product was evaporated to dryness to yield the product as blue-green film coating the bottom of the vial (2.54 mg, 59%, 2TFA salt). $^1$H NMR (400 MHz, DMSO-d$_6$) δ 9.96 (s, 1H), 8.28 (t, J=5.7 Hz, 1H), 8.14 (t, J=5.8 Hz, 1H), 7.85 (s, 1H), 7.73-7.63 (m, 3H), 7.57 (dd, J=7.6, 3.5 Hz, 2H), 7.56-7.49 (m, 2H), 7.44-7.29 (m, 4H), 7.27-7.13 (m, 4H), 6.14 (dd, J=14.2, 5.0 Hz, 2H), 4.47 (t, J=5.2 Hz, 4H), 4.25 (d, J=5.6 Hz, 4H), 4.12 (s, 2H), 4.03 (s, 2H), 3.77 (t, J=5.2 Hz, 2H), 3.61 (s, 3H), 3.46 (d, J=28.7 Hz, 12H), 3.28 (q, J=5.9 Hz, 2H), 3.03 (t, J=5.3 Hz, 2H), 2.91-2.77 (m, 4H), 2.14-2.05 (m, 2H), 1.88-1.50 (m, 20H), 1.42-1.30 (m, 2H). $^{13}$C NMR (101 MHz, DMSO) δ 172.12, 171.66, 170.49, 169.58, 169.23, 167.77, 165.95, 158.56, 158.36, 158.16, 157.97, 147.99, 147.46, 144.88, 143.01, 142.34, 140.97, 140.93, 136.36, 136.14, 134.99, 132.08, 131.91, 130.34, 128.64, 124.70, 124.48, 123.21, 122.47, 122.37, 120.17, 117.23, 115.54, 110.97, 110.86, 100.28, 99.64, 70.72, 70.57, 69.72, 69.65, 69.63, 68.95, 68.85, 49.42, 48.70, 48.65, 43.25, 38.33, 37.55, 36.56, 35.68, 35.05, 34.18, 31.18, 28.87, 27.31, 27.13, 26.59, 25.91, 24.96, 23.47, 21.20. HRMS calcd for $C_{64}H_{82}N_9O_9$ [M]$^+$1120.6236 found 1120.6211.

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. An antibody compound, comprising a variant of catalytic antibody 38C2 (38C2_Arg), or antigen binding fragment thereof, that contains a substitution of arginine for the reactive lysine residue (Lys99) in the hydrophobic cleft.

2. The antibody compound of claim 1, wherein the catalytic antibody is humanized 38C2 (h38C2).

3. The antibody compound of claim 1, wherein the 38C2_Arg or antigen binding fragment thereof comprises heavy chain and light chain variable domain sequences respectively shown in SEQ ID NOs:1 and 2.

4. The antibody compound of claim 1, which is a dual variable domain (DVD) compound or an antigen-binding fragment thereof comprising (i) the 38C2_Arg or antigen binding fragment thereof, and (ii) a second antibody variable domain recognizing a target of interest.

5. The antibody compound of claim 4, wherein 38C2_Arg is positioned closer to the C-terminus in the antibody compound than the second variable domain.

6. The antibody compound of claim 4, which is a homodimeric molecule comprising Lys99Arg substitution in both antibody arms.

7. The antibody compound of claim 4, which is a heterodimeric molecule comprising Lys99Arg substitution in only one antibody arm.

8. The antibody compound of claim 4, wherein the dual variable domain compound is a bispecific immunoglobulin molecule.

9. The antibody compound of claim 4, comprising an antigen-binding fragment of a dual variable domain (DVD) compound that is a Fab, Fab', F(ab')$_2$, Fv or scFv.

10. The antibody compound of claim 9, comprising a Fab.

11. The antibody compound of claim 4, comprising a chimeric immunoglobulin sequence or a humanized immunoglobulin sequence.

12. The antibody compound of claim 4, where the target of interest is a tumor cell surface antigen.

13. The antibody compound of claim 12, wherein the tumor cell surface antigen is HER2, FOLR1, FCMR, CD138, CD79B, PSMA, BCMA, CD38, SLAMF7, Siglec-6, CD70, ROR1 or ROR2.

14. An antibody drug conjugate (ADC) comprising at least one drug moiety that is conjugated to an antibody compound via a reactive arginine residue in the antibody compound, wherein the antibody compound comprises a variant of catalytic antibody 38C2 (38C2_Arg), or antigen binding fragment thereof, that contains a substitution of arginine for the reactive lysine residue in the hydrophobic cleft.

15. The antibody drug conjugate of claim 14, wherein the antibody compound is a dual variable domain (DVD) compound or an antigen-binding fragment thereof comprising (i) the 38C2_Arg or antigen binding fragment thereof, and (ii) a second antibody variable domain recognizing a target of interest.

16. The antibody drug conjugate of claim 15, wherein the 38C2_Arg or antigen binding fragment thereof comprises heavy chain and light chain variable domain sequences respectively shown in SEQ ID NOs:1 and 2, and the target of interest is HER2.

17. The antibody drug conjugate of claim 16, wherein the antibody compound is a dual variable domain (DVD)-Fab comprising heavy chain and light chain sequences shown in SEQ ID NOs:5 and 7, respectively.

18. The antibody drug conjugate of claim 16, wherein the antibody compound is a dual variable domain (DVD)-IgG1 comprising heavy chain and light chain sequences shown in SEQ ID NOs:6 and 7, respectively.

19. A pharmaceutical composition, comprising an effective amount of the antibody drug conjugate of claim 15 and optionally a pharmaceutically acceptable carrier.

20. A method for treating cancer in a subject, comprising administering to the subject in need of treatment the pharmaceutical composition of claim 19.

21. The antibody drug conjugate of claim 14, wherein the catalytic antibody is humanized 38C2 (h38C2).

22. The antibody drug conjugate of claim 14, wherein the drug moiety is conjugated to the antibody compound via a linker moiety.

23. The antibody drug conjugate of claim 22:
wherein the drug moiety is derivatized with the linker moiety prior to conjugation with the antibody compound; or
wherein the linker moiety is a cleavable linker; or
wherein the linker moiety comprises phenylglyoxal (PGO), glyoxal (GO), or methylglyoxal (MGO).

24. The antibody drug conjugate of claim 15, wherein the DVD compound or an antigen-binding fragment thereof is:
a homodimeric molecule comprising Lys99Arg substitution in both antibody arms; or
a heterodimeric molecule comprising Lys99Arg substitution in only one antibody arm.

25. The antibody drug conjugate of claim 15, wherein the antibody compound comprises an antigen-binding fragment of a dual variable domain (DVD) compound that is a Fab, Fab', F(ab')$_2$, Fv or scFv.

26. The antibody drug conjugate of claim 25, wherein the antibody compound comprises a Fab.

27. The antibody drug conjugate of claim 15, where the target of interest is a tumor cell surface antigen.

28. The antibody drug conjugate of claim 27, wherein the tumor cell surface antigen is HER2, FOLR1, FCMR, CD138, CD79B, PSMA, BCMA, CD38, SLAMF7, Siglec-6, CD70, ROR1 or ROR2.

29. The antibody drug conjugate of claim 14, wherein the drug moiety is a cytotoxic agent or a siRNA.

30. The antibody drug conjugate of claim 29, wherein the cytotoxic agent is selected from a toxin, a chemotherapeutic agent, a photoabsorber, an antibiotic, a radioactive isotope, a chelated radioactive isotope and a nucleolytic enzyme.

31. The antibody drug conjugate of claim 14, wherein the drug moiety is an auristatin, a dolastatin, a cemadotin, a camptothecin, an amanitin, a maytansinoid, a pyrrolobenzodiazepine, an indolinobenzodiazepine, a duocarmycin, an enediyne, a doxorubicin or a polymerized drug.

32. The antibody drug conjugate of claim 14, wherein the drug moiety is monomethyl auristatin F (MMAF).

33. The antibody drug conjugate of claim 18, wherein the dual variable domain (DVD)-IgG1 is:
a homodimeric molecule comprising Lys99Arg substitution in both antibody arms; or
a heterodimeric molecule comprising Lys99Arg substitution in only one antibody arm.

34. The antibody drug conjugate of claim 33, wherein two different drug moieties are conjugated to the two antibody arms of the heterodimeric dual variable domain (DVD)-IgG1 molecule.

* * * * *

SEQUENCE LISTING

```
<160> NUMBER OF SEQ ID NOS: 8

<210> SEQ ID NO 1
<211> LENGTH: 118
<212> TYPE: PRT
<213> ORGANISM: Artificial sequence
<220> FEATURE:
<223> OTHER INFORMATION: Synthetic sequence

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Arg Thr Tyr Phe Tyr Ser Phe Ser Tyr Trp Gly Gln Gly Thr
            100                 105                 110

Leu Val Thr Val Ser Ser
        115

<210> SEQ ID NO 2
<211> LENGTH: 112
<212> TYPE: PRT
<213> ORGANISM: Artificial sequence
<220> FEATURE:
<223> OTHER INFORMATION: Synthetic sequence

<400> SEQUENCE: 2

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110
```

<210> SEQ ID NO 3
<211> LENGTH: 6
<212> TYPE: PRT
<213> ORGANISM: Artificial sequence
<220> FEATURE:
<223> OTHER INFORMATION: Synthetic sequence

<400> SEQUENCE: 3

Ala Ser Thr Lys Gly Pro
1               5

<210> SEQ ID NO 4
<211> LENGTH: 12
<212> TYPE: PRT
<213> ORGANISM: Artificial sequence
<220> FEATURE:
<223> OTHER INFORMATION: Synthetic sequence

<400> SEQUENCE: 4

Thr Val Ala Ala Pro Ser Val Phe Ile Phe Pro Pro
1               5                   10

<210> SEQ ID NO 5
<211> LENGTH: 347
<212> TYPE: PRT
<213> ORGANISM: Artificial sequence
<220> FEATURE:
<223> OTHER INFORMATION: Synthetic sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Asn Tyr Trp Met
145                 150                 155                 160

Ser Trp Val Arg Gln Ser Pro Glu Lys Gly Leu Glu Trp Val Ser Glu
                165                 170                 175

Ile Arg Leu Arg Ser Asp Asn Tyr Ala Thr His Tyr Ala Glu Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Gly Ile Tyr Tyr Cys
    210                 215                 220

Arg Thr Tyr Phe Tyr Ser Phe Ser Tyr Trp Gly Gln Gly Thr Leu Val
225                 230                 235                 240

```
Thr Val Ser Ser Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
            275                 280                 285

Ala Leu Thr Ser Gly Val His Thr Phe Pro Ala Val Leu Gln Ser Ser
        290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Arg Val Glu Pro Lys Ser Cys
            340                 345
```

<210> SEQ ID NO 6
<211> LENGTH: 574
<212> TYPE: PRT
<213> ORGANISM: Artificial sequence
<220> FEATURE:
<223> OTHER INFORMATION: Synthetic sequence

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Asn Tyr Trp Met
145                 150                 155                 160

Ser Trp Val Arg Gln Ser Pro Glu Lys Gly Leu Glu Trp Val Ser Glu
                165                 170                 175

Ile Arg Leu Arg Ser Asp Asn Tyr Ala Thr His Tyr Ala Glu Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Gly Ile Tyr Tyr Cys
    210                 215                 220

Arg Thr Tyr Phe Tyr Ser Phe Ser Tyr Trp Gly Gln Gly Thr Leu Val
225                 230                 235                 240

Thr Val Ser Ser Ala Ser Thr Lys Gly Pro Ser Val Phe Pro Leu Ala
                245                 250                 255
```

```
Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Arg Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Ala
                565                 570

<210> SEQ ID NO 7
<211> LENGTH: 332
<212> TYPE: PRT
<213> ORGANISM: Artificial sequence
<220> FEATURE:
<223> OTHER INFORMATION: Synthetic sequence

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Ala Ser Thr Lys Gly
                100                 105                 110
Pro Glu Leu Gln Met Thr Gln Ser Pro Ser Ser Leu Ser Ala Ser Val
            115                 120                 125
Gly Asp Arg Val Thr Ile Thr Cys Arg Ser Ser Gln Ser Leu Leu His
            130                 135                 140
Thr Tyr Gly Ser Pro Tyr Leu Asn Trp Tyr Leu Gln Lys Pro Gly Gln
145                 150                 155                 160
Ser Pro Lys Leu Leu Ile Tyr Lys Val Ser Asn Arg Phe Ser Gly Val
                165                 170                 175
Pro Ser Arg Phe Ser Gly Ser Gly Ser Gly Thr Asp Phe Thr Leu Thr
                180                 185                 190
Ile Ser Ser Leu Gln Pro Glu Asp Phe Ala Val Tyr Phe Cys Ser Gln
            195                 200                 205
Gly Thr His Leu Pro Tyr Thr Phe Gly Gly Gly Thr Lys Val Glu Ile
            210                 215                 220
Lys Arg Thr Val Ala Ala Pro Ser Val Phe Ile Phe Pro Pro Ser Asp
225                 230                 235                 240
Glu Gln Leu Lys Ser Gly Thr Ala Ser Val Val Cys Leu Leu Asn Asn
                245                 250                 255
Phe Tyr Pro Arg Glu Ala Lys Val Gln Trp Lys Val Asp Asn Ala Leu
                260                 265                 270
Gln Ser Gly Asn Ser Gln Glu Ser Val Thr Glu Gln Asp Ser Lys Asp
            275                 280                 285
Ser Thr Tyr Ser Leu Ser Ser Thr Leu Thr Leu Ser Lys Ala Asp Tyr
            290                 295                 300
Glu Lys His Lys Val Tyr Ala Cys Glu Val Thr His Gln Gly Leu Ser
305                 310                 315                 320
Ser Pro Val Thr Lys Ser Phe Asn Arg Gly Glu Cys
                325                 330

<210> SEQ ID NO 8
<211> LENGTH: 19
<212> TYPE: PRT
<213> ORGANISM: Artificial sequence
<220> FEATURE:
<223> OTHER INFORMATION: Synthetic sequence

<400> SEQUENCE: 8

Met Asp Trp Thr Trp Arg Ile Leu Phe Leu Val Ala Ala Ala Thr Gly
1               5                   10                  15

Ala His Ser
```